US007947684B2

(12) United States Patent  (10) Patent No.: US 7,947,684 B2
Pauls et al.  (45) Date of Patent: May 24, 2011

(54) 1-AROYL-PIPERIDINYL BENZAMIDINES

(75) Inventors: Heinz Pauls, Flemington, NJ (US); Yong Gong, Bridgewater, NJ (US); Julian Levell, Summit, NJ (US); Peter Astles, Kent (GB); Paul R. Eastwood, Essex (GB)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1643 days.

(21) Appl. No.: 10/616,141

(22) Filed: Jul. 8, 2003

(65) Prior Publication Data

US 2004/0220171 A1  Nov. 4, 2004

Related U.S. Application Data

(63) Continuation of application No. 09/841,417, filed on Apr. 24, 2001, now abandoned.

(60) Provisional application No. 60/200,066, filed on Apr. 27, 2000.

(30) Foreign Application Priority Data

Jul. 27, 2000 (GB) .................................. 0018306.1

(51) Int. Cl.
*C07D 295/00* (2006.01)
*C07D 241/02* (2006.01)
*A61K 31/497* (2006.01)
*A61K 31/445* (2006.01)

(52) U.S. Cl. ..................... 514/252.1; 514/315; 544/336; 546/184

(58) Field of Classification Search .................. 514/252, 514/1, 252.1, 315; 544/336; 546/184
See application file for complete search history.

(56) References Cited

U.S. PATENT DOCUMENTS

| 5,364,862 | A | | 11/1994 | Spada et al. | |
|---|---|---|---|---|---|
| 5,442,064 | A | * | 8/1995 | Pieper et al. | 544/360 |
| 5,736,554 | A | | 4/1998 | Spada et al. | |
| 6,004,981 | A | | 12/1999 | Buckman et al. | |
| 6,022,969 | A | | 2/2000 | Rice et al. | |

OTHER PUBLICATIONS

Beil, W., et al., Phenotypic and Functional Characterization of Mast Cells Derived from Renal Tumor Tissues, Experimental Hematology vol. 26, 1998, pp. 158-169.
Bischoff, S C., et al., Quantitative Assessment of Intestinal Eosinophils and Mast Cells in Inflammatory Bowel Disease, Histopathology 1996, vol. 28, pp. 1-13.
Broersma, et al., The Effect Of Thrombin Inhibition In a Rat Arterial Thrombosis Model, Thrombosis Research 64; 405-412, 1991.
Buckley, M., et al., Mast Cell Subpopulations in the Synovial Tissue of Patients with Osteoarthritis: Selective Increase in Numbers of Tryptase-positive, Chymase-negative Mast Cells, Journal of Pathology, vol. 186, 1998, pp. 67-74.

Cairns, et al., Mast Cell Tryptase Stimulates the Synthesis of Type I Collagenin Himan Lung Fibroblasts, J. Clin. Invest., vol. 99, No. 6, Mar. 1997, pp. 1313-1321.
Caughey, G., et al., Substance P and Vasoactive Intestinal Peptide Degradation by Mast Cell Tryptase and Chymase, The Journal of Pharmacology and Experimental Therapeutics, (1988), vol. 244, No. 1, pp. 133-137.
Franconi, G., et al. et al., Mast Cell Tryptase and Chymase Reverse Airway Smooth Muscle Relaxation Induced by Vasoactive Intestinal Peptide in the Ferret, The Journal of Pharmacology and Experimental Therapeutics, (1989), vol. 248, No. 3, pp. 947-951.
Hasebe, et al., Photochemical generation of aliphatic radicals from benzophenone oxime esters: simple synthesis of alkylbenzenes and alkylpyridines, CAS Abstr. 106:119639-1987:119639, Hasebe et al, Tetr. Lett 27/28,3239-42(1986).
Higuchi, T, et al., Pro-drugs as Novel Drug Delivery Systems, ACS Symposium Series, vol. 14.
Holst, et al., Antithrombotic Effect of Recombinant Truncated Tissue Factor Pathway Inhibitor (TFPI 1-161) in Experimental Venous Thrombosis—A Comparison with Low Molecular Weight Heparin, Thrombosis and Haemostasis, 71 (2) 214-219 (1994).
Irani, et al., Human Conjunctival Mast Cells: Distribution of MCT and MCTC in Vernal Conjunctivitis and Giant Papillary Conjunctivitis, Journal of Allergy and Clinical Immunology, vol. 86, No. 1 pp. 34-40.
Jarvikallio, A, et al., Quantitative Analysis of Tryptase- and Chymase-containing Mast Cells in Atopic Dermatitis and Nummular Eczema, British Journal of Dermatology 1997, vol. 136, pp. 871-877.
Jeziorska, M, et al., Mast Cell Distribution, Activation, and Phenotype in Atherosclerotic Lesions of Human Carotid Arteries, Journal of Pathology, vol. 182, 1997, pp. 115-122.
Komoto, et a., Preparation of .alpha.-[(N-benzoylpiperidinyl) phenoxy] isobutyrates and analogs as hypolipemics, CAS Abstr. 122:81127-1995:58673, Komoto et al, CA 2110095/6/1994.
Kurz, et al., Rat Model Of Arterial Thrombosis Induced by Ferric Chloride, Thrombosis Research 60; 269-280, 1990.
McEuen, et al., Guinea Pig Lung Tryptase, Biochemical Pharmacology, vol. 52, pp. 331-340, 1996.
Naukkarinen, A, et al., Immunohistochemical Analysis of Sensory Nerves and Neuropeptides, and Their Contacts with Mast Cells in Developing and Mature Psoriatic Lesions, Archives of Dermatological Research vol. 285, 1993 pp. 341-346.

(Continued)

*Primary Examiner* — Paul V. Ward
(74) *Attorney, Agent, or Firm* — James W. Bolcsak

(57) ABSTRACT

This invention relates to compounds of formula

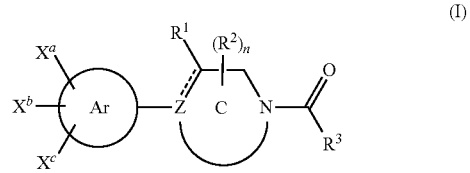

(I)

which inhibit Factor Xa or tryptase, to pharmaceutical compositions containing the compounds, and to the use of the compounds for the treatment of patients suffering from conditions which can be ameliorated by the administration of an inhibitor of Factor Xa or tryptase.

12 Claims, No Drawings

OTHER PUBLICATIONS

Roche, E., et al., Bioreversible Carriers in Drug Design Theory and Application, American Pharmaceutical Association and Pergamon Press, 1987.

Ruoss, Stephen J, et al., Mast Cell Tryptase is a Mitogen for Cultured Fibroblasts, J. Clin. Invest., vol. 88, Aug. 1991, pp. 493-499.

Schwartz, L., et al., The a Form of Human Tryptase Is the Predominant Type Present in Blood at Baseline in Normal Subjects and Is Elevated in Those with Systemic Mastocytosis, The Journal of Clinical Investigation, vol. 96, Dec. 1995, pp. 2702-2710.

Sekizawa, K., et al., Mast Cell Tryptase Causes Airway Smooth Muscle Hyperresponsiveness in Dogs, J. Clin. Invest., vol. 83, Jan. 1989, pp. 175-179.

Steinhoff, M., et al., Agonists of Proteinase-activated Receptor 2 Induce Inflammation by a Neurogenic Mechanism, Nature Medicine, vol. 6, No. 2, Feb. 2000, pp. 151-158.

Tam, et al., Degradation of Airway Neuropeptides by Human Lung Tryptase, Am. J. Respir. Cell Mol. Biol. vol. 3, 1990, pp. 27-32.

Tetlow, L., et al., Distribution, Activation and Tryptase/Chymase Phenotype of Mast Cells in the Rheumatoid Lesion, Annals of the Rheumatic Diseases 1995; vol. 54, pp. 549-555.

Wilson, S J., et al., Inflammatory Mediators in Naturally Occurring Rhinitis, Clinical and Experimental Allergy, 1998, vol. 28, pp. 220-227.

Zhang, M., et al., Mast Cell Tryptase and Asthma, Mediators of Inflammation, vol. 6, 1997, pp. 311-317.

* cited by examiner

1-AROYL-PIPERIDINYL BENZAMIDINES

DOMESTIC PRIORITY CLAIM

This application claims the benefit under 35 U.S.C. §119(e) of U.S. Provisional Application No. 60/200,066 filed on Apr. 27, 2000, which is hereby incorporated by reference in its entirety.

FIELD OF THE INVENTION

The compounds of formula I exhibit useful pharmacological activity and accordingly are incorporated into pharmaceutical compositions and used in the treatment of patients suffering from certain medical disorders. More especially, the compounds of formula I exhibit Factor Xa inhibitory activity and tryptase inhibitory activity. The present invention is directed to compounds of formula I, compositions containing compounds of formula I, and their use for treating a patient suffering from, or subject to, conditions which can be ameliorated by the administration of an inhibitor of Factor Xa or an inhibitor of tryptase.

Factor Xa is the penultimate enzyme in the coagulation cascade. Both free factor Xa and factor Xa assembled in the prothrombinase complex (Factor Xa, Factor Va, calcium and phospholipid) are inhibited by compounds of formula I. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

Tryptase is stored in mast cell secretory granules and is the major secretory protease of human mast cells. Tryptase has been implicated in a variety of biological processes, including degradation of vasodilating and bronchorelaxing neuropeptides (Caughey, et al., J. Pharmacol. Exp. Ther. 244:133-137 (1988); Franconi, et al., J. Pharmacol. Exp. Ther. 248:947-951 (1988); and Tam, et al., Am. J. Respir. Cell Mol. Biol. 3:27-32 (1990)) and modulation of bronchial responsiveness to histamine (see Sekizawa, et al., J. Clin. Invest. 83:175-179 (1989)). As a result, tryptase inhibitors may be useful as anti-inflammatory agents (K Rice, P. A. Sprengler, Current Opinion in Drug Discovery and Development (1999) 2(5): 463-474) particularly in the treatment of chronic asthma (M. Q. Zhang, H. Timmerman, Mediators Inflamm (1997) 112: 311-317) and may also be useful in treating or preventing allergic rhinitis (S. J. Wilson et al, Clin. Exp. Allergy (1998) 28:220-227), inflammatory bowel disease (S. C. Bischoff et al, Histopathology (1996) 28:1-13), psoriasis (A. Naukkarinen et al, Arch. Dermatol. Res. (1993) 285:341-346), conjunctivitis (A. A. Irani et al, J. Allergy Clin. Immunol. (1990) 86:34-40), atopic dermatitis (A. Jarvikallio et al, Br. J. Dermatol. (1997) 136:871-877), rheumatoid arthritis (L. C Tetlow et al, Ann. Rheum. Dis. (1998) 54:549-555), osteoarthritis (M. G. Buckley et al, J. Pathol. (1998) 186:67-74), gouty arthritis, rheumatoid spondylitis, and diseases of joint cartilage destruction.

In addition, tryptase has been shown to be a potent mitogen for fibroblasts, suggesting its involvement in the pulmonary fibrosis in asthma and interstitial lung diseases (Ruoss et al., J. Clin. Invest. 88:493-499 (1991)). Therefore, tryptase inhibitors may be useful in treating or preventing fibrotic conditions (J. A. Cairns, A. F. Walls, J. Clin. Invest. (1997) 99:1313-1321) for example, fibrosis, sceleroderma, pulmonary fibrosis, liver cirrhosis, myocardial fibrosis, neurofibromas and hypertrophic scars.

Additionally, tryptase inhibitors may be useful in treating or preventing myocardial infarction, stroke, angina and other consequences of atherosclerotic plaque rupture (M. Jeziorska et al, J. Pathol. (1997) 182:115-122). Tryptase has also been discovered to activate prostromelysin which in turn activates collagenase, thereby initiating the destruction of cartilage and periodontal connective tissue, respectively. Therefore, tryptase inhibitors could be useful in the treatment or prevention of arthritis, periodontal disease, diabetic retinopathy, and tumor growth (W. J. Beil et al, Exp. Hematol. (1198) 26:158-169). Also, tryptase inhibitors may be useful in the treatment of anaphylaxis (L. B. Schwarz et al, J. Clin. Invest. (1995) 96:2702-2710), multiple sclerosis (M. Steinhoff et al, Nat. Med. (N. Y.) (2000) 6(2):151-158), peptic ulcers and syncytial viral infections.

Mast cell mediated inflammatory conditions, in particular asthma, are a growing public health concern. Asthma is frequently characterized by progressive development of hyper-responsiveness of the trachea and bronchi to both immunospecific allergens and generalized chemical or physical stimuli, which lead to the onset of chronic inflammation. Leukocytes containing IgE receptors, notably mast cells and basophils, are present in the epithelium and underlying smooth muscle tissues of bronchi. These leukocytes initially become activated by binding of specific inhaled antigens to the IgE receptors and then release a number of chemical mediators. For example, degranulation of mast cells leads to the release of proteoglycans, peroxidase, arylsulfatase B, tryptase and chymase, which results in bronchiole constriction.

SUMMARY OF THE INVENTION

This invention is directed to a compound of formula I:

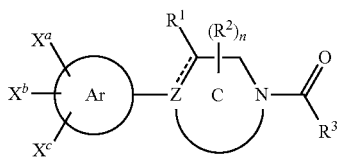

wherein:

Z is a carbon or nitrogen atom;

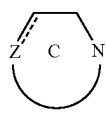

is a 4 to 7-membered azaheterocyclyl or a 4 to 7-membered azaheterocyclenyl group;

===== is a single or double bond, provided that when Z is a nitrogen atom then ===== is a single bond;

is an aryl group, a monocyclic heteroaryl group, or a bicyclic azaheteroaryl group which includes a first proximal ring that is attached to the

moiety and a ring distal to said first ring, said distal ring including at least one nitrogen atom;

$R^1$ is hydrogen, —$CH_2OR^{12}$, —$CH_2SR^{12}$, —$CO_2R^{13}$, —$C(O)R^{13}$, or —$CONR^{13}R^{13}$;

$R^2$ is hydrogen, alkyl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, $Y^1Y^2N$—, $Y^1Y^2N$-alkyl-, $Y^1Y^2NCO$— or $Y^1Y^2NSO_2$—;

$R^3$ is cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl;

Xa, Xb, Xc are independently selected from hydrogen, $R^4R^5N$—, (hydroxy)HN—, (alkoxy)HN—, $R^6O$—, $R^4R^5NCO$—, $R^4R^5NSO_2$—, $R^6CO$—, halo, cyano, nitro, $R^7(O)C(CH_2)_q$—, and

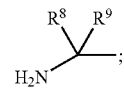

and when

is a bicyclic heteroaryl group, then Xc is a substituent that is at the alpha position with respect to a nitrogen atom of said distal ring of

and Xc is selected from the group consisting of H, hydroxy and $H_2N$—, (optionally substituted lower alkyl)HN (hydroxy)HN—, and (alkoxy)HN—;

$R^4$ and $R^5$ are independently H or optionally substituted lower alkyl, or one of $R^4$ and $R^5$ is H and the other of $R^4$ and $R^5$ is $R^7(O)CCH_2$— or lower acyl;

$R^6$ is H, optionally substituted lower alkyl, lower acyl or $R^7(O)CCH_2$—;

$R^7$ is H, optionally substituted lower alkyl, alkoxy or hydroxy;

$R^8$ and $R^9$ taken together are =$NR^{10}$;

$R^{10}$ is hydrogen, $R^{11}O_2C$—, $R^{11}O$—, HO—, cyano, $R^{11}CO$—, HCO—, lower alkyl, nitro, or $Y^{1a}Y^{2a}N$—;

$R^{11}$ is alkyl, aralkyl, or heteroaralkyl;

$R^{12}$ is hydrogen, lower alkyl, aryl(lower alkyl), heteroaryl (lower alkyl), lower acyl, aroyl, or heteraroyl;

$R^{13}$ is hydrogen or lower alkyl;

$Y^1$ and $Y^2$ are independently hydrogen, alkyl, aryl, and aralkyl, or where the substituent is $Y^1Y^2N$— or $Y^1Y^2N$-alkyl- then one of $Y^1$ and $Y^2$ is acyl or aroyl and the other of $Y^1$ and $Y^2$ is hydrogen, alkyl, aryl, or aralkyl;

$Y^{1a}$ and $Y^{2a}$ are independently hydrogen or alkyl;

n is 1, 2, 3, or 4; or a pharmaceutically acceptable salt thereof, an N-oxide thereof, a hydrate thereof or a solvate thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Effective amount" is meant to describe an amount of compound of the present invention effective in inhibiting Factor Xa or tryptase and thus producing the desired therapeutic effect.

"Alkyl" means an aliphatic hydrocarbon group which may be straight or branched having about 1 to about 15 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 6 carbon atoms in the chain which may be straight or branched. The alkyl group may be substituted by one or more halo, cycloalkyl or cycloalkenyl. Representative alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 6 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo. Representative alkenyl groups include ethenyl, propenyl, n-butenyl, i-butenyl, 3-methylbut-2-enyl, n-pentenyl, heptenyl, octenyl and decenyl.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. Representative alkynyl groups include ethynyl, propynyl, n-butynyl, 2-butynyl, 3-methylbutynyl, n-pentynyl, heptynyl, octynyl and decynyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like.

"Cycloalkenyl" means a non-aromatic mono- or multicyclic ring system of about 3 to about 10 carbon atoms, preferably of about 5 to about 10 carbon atoms which contains at least one carbon-carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Heterocyclenyl" means a non-aromatic monocyclic or multicyclic ring system of about 3 to about ring atoms, preferably about 5 to about 10 ring atoms, in which one or more of the atoms in the ring system is/are element(s) other than carbon, for example nitrogen, oxygen or sulfur atom, and which contains at least one carbon-carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom respectively is present as a ring atom. The heterocyclenyl is optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocylyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Aryl" means an aromatic monocyclic or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl and naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide, 1,4-benzodioxane, indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon atom.

"Fused heterocyclylaryl" means a radical derived from a fused arylheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. Representative fused cycloalkenylheteroaryl are as described herein for fused heteroaylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of about 5 to about 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon atom.

"Fused heterocyclenylheteroaryl" means a radical derived from a fused heteroarylheterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to about 6 ring atoms and the heterocyclyl consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol[3,4-b]quinolin-2-yl, 1,2,3,4-tetrahydrobenz [b][1,7] naphthyridin-2-yl, 1,2,3,4-tetrahydrobenz [b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2yl, 5,6,7,8-tetrahydro[1,7]napthyridinyl, 1,2,3,4-tetrahydro[2,7]naphthyridyl, 2,3-dihydro[1,4]dioxino[2,3-b]pyridyl, 2,3-dihydro[1,4]dioxino[2,3-b]pyridyl, 3,4-dihydro-2H-1-oxa [4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]naphthyridinyl, 1,2,3,4-tetrahydro[1,6]napthyridinyl, 1,2,3,4-tetrahydro[1,7]napthyridinyl, 1,2,3,4-tetrahydro[1,8]naphthyridinyl, 1,2,3,4-tetrahydro[2,6]napthyridinyl, and the like, in which the bond to the parent moiety is through a non-aromatic carbon atom.

"Fused heterocyclylheteroaryl" means a radical derived from a fused heteroarylheterocyclyl as defined herein, by removal of a hydrogen atom from the heteroaryl portion. Representative fused heterocyclylheteroaryl are as described herein for fused heteraryheterocyclyl, except that the bond to the parent moiety is through an aromatic carbon atom.

"Aralkyl" means an aryl-alkyl-group in which the aryl and alkyl are as previously described. Preferred aralkyls contain a lower alkyl moiety. Representative aralkyl groups include benzyl, 2-phenethyl and naphthlenemethyl.

"Aralkenyl" means an aryl-alkenyl-group in which the aryl and alkenyl are as previously described. Preferred aralkenyls contain a lower alkenyl moiety. Representative aralkenyl groups include 2-phenethenyl and 2-naphthylethenyl.

"Aralkynyl" means an aryl-alkynyl-group in which the aryl and alkynyl are as previously described. Preferred aralkynyls contain a lower alkynyl moiety. Representative aralkynyl groups include phenacetylenyl and naphthylacetylenyl.

"Heteroaralkyl" means an heteroaryl-alkyl-group in which the heteroaryl and alkyl are as previously described. Preferred heteroaralkyls contain a lower alkyl moiety. Representative aralkyl groups include pyridylmethyl, 2-(furan-3-yl)ethyl and quinolin-3-ylmethyl.

"Heteroaralkenyl" means an heteroaryl-alkenyl-group in which the heteroaryl and alkenyl are as previously described. Preferred heteroaralkenyls contain a lower alkenyl moiety. Representative heteroaralkenyl groups include 2-(pyrid-3-yl) ethenyl and 2-(quinolin-3-yl)ethenyl.

"Heteroaralkynyl" means an heteroaryl-alkynyl-group in which the heteroaryl and alkynyl are as previously described. Preferred heteroaralkynyls contain a lower alkynyl moiety. Representative heteroaralkynyl groups include pyrid-3-ylacetylenyl and quinolin-3-ylacetylenyl.

"Hydroxyalkyl" means a HO-alkyl-group in which alkyl is as previously defined. Preferred hydroxyalkyls contain lower alkyl. Representative hydroxyalkyl groups include hydroxymethyl and 2-hydroxyethyl.

"Acyl" means an H—CO— or alkyl-CO— group in which the alkyl group is as previously described. Preferred acyls contain a lower alkyl. Representative acyl groups include formyl, acetyl, propanoyl, 2-methylpropanoyl, butanoyl and palmitoyl.

"Aroyl" means an aryl-CO— group in which the aryl group is as previously described. Representative groups include benzoyl and 1- and 2-naphthoyl.

"Heteroaroyl" means a heteroaryl-CO— group in which the heteroaryl group is as previously described. Representative groups include nicotinoyl and pyrrol-2-ylcarbonyl and 1- and 2-naphthoyl.

"Alkoxy" means an alkyl-O— group in which the alkyl group is as previously described. Representative alkoxy groups include methoxy, ethoxy, n-propoxy, i-propoxy, n-butoxy and heptoxy.

"Aryloxy" means an aryl-O— group in which the aryl group is as previously described. Representative aryloxy groups include phenoxy and naphthoxy.

"Aralkyloxy" means an aralkyl-O— group in which the aralkyl groups is as previously described. Representative aralkyloxy groups include benzyloxy and 1- or 2-naphthalenemethoxy.

"Alkylthio" means an alkyl-S— group in which the alkyl group is as previously described. Representative alkylthio groups include methylthio, ethylthio, i-propylthio and heptylthio.

"Arylthio" means an aryl-S— group in which the aryl group is as previously described. Representative arylthio groups include phenylthio and naphthylthio.

"Aralkylthio" means an aralkyl-S— group in which the aralkyl group is as previously described. A representative aralkylthio group is benzylthio.

"$Y^1Y^2N$—" means a substituted or unsubstituted amino group, wherein $Y^1$ and $y^2$ are independently hydrogen, alkyl, aryl, or aralkyl, or one of $Y^1$ and $Y^2$ is acyl or aroyl and the other of $Y^1$ and $Y^2$ is hydrogen, alkyl, aryl, and aralkyl. Representative groups include amino ($H_2N-$), methylamino, ethylmethylamino, dimethylamino and diethylamino.

"Alkoxycarbonyl" means an alkyl-O—CO— group. Representative alkoxycarbonyl groups include methoxy- and ethoxycarbonyl.

"Aryloxycarbonyl" means an aryl-O—CO— group. Representative aryloxycarbonyl groups include phenoxy- and naphthoxycarbonyl.

"Aralkoxycarbonyl" means an aralkyl-O—CO— group. A representative aralkoxycarbonyl group is benzyloxycarbonyl.

"$Y^1Y^2NCO-$" means a substituted or unsubstituted carbamoyl group, wherein $Y^1$ and $Y^2$ are independently hydrogen, alkyl, aryl, or aralkyl. Representative groups are carbamoyl ($H_2NCO-$) and dimethylaminocarbamoyl ($Me_2NCO-$).

"$Y^1Y^2NSO_2-$" means a substituted or unsubstituted sulfamoyl group, wherein $Y^1$ and $Y^2$ are independently hydrogen, alkyl, aryl, or aralkyl. Representative groups are sulfamoyl ($H_2NSO_2-$) and dimethylsulfamoyl ($Me_2NSO_2-$).

"Alkylsulfonyl" means an alkyl-$SO_2-$ group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2-$ group.

"Arylsulfinyl" means an aryl-SO— group.

"Halo" means fluoro, chloro, bromo, or iodo. Preferred are fluoro, chloro or bromo, and more preferred are fluoro or chloro.

"Ring system substituent" means a substituent attached which optionally replaces hydrogen on an aromatic or non-aromatic ring system. Ring system substituents are selected from the group consisting of aryl, heteroaryl, aralkyl, aralkenyl, aralkynyl, heteroaralkyl, heteroaralkenyl, heteroaralkynyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, $Y^1Y^2N-$, $Y^1Y^2N$-alkyl-, $Y^1Y^2NCO-$ or $Y^1Y^2NSO_2-$, wherein $Y^1$ and $Y^2$ are independently hydrogen, alkyl, aryl, aralkyl, or $Y^1Y^2N$-alkyl-; or where the substituent is $Y^1Y^2N-$ or $Y^1Y^2N$-alkyl- then one of $Y^1$ and $Y^2$ is acyl or aroyl and the other of $Y^1$ and $Y^2$ is hydrogen, alkyl, aryl, or aralkyl. When a ring system is saturated or partially saturated, the "ring system substituent" further comprises methylene ($H_2C=$), oxo (O=) and thioxo (S=).

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Prodrug" means a form of the compound of formula I suitable for administration to a patient without undue toxicity, irritation, allergic response, and the like, and effective for their intended use, including ketal, ester and zwitterionic forms. A prodrug is transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

Preferred Embodiments

A preferred embodiment of the invention is a method for treating a patient suffering from a disease state capable of being modulated by inhibiting tryptase activity comprising administering to said patient a pharmaceutically effective amount of a compound of formula I.

Another preferred embodiment of the invention is a method for preventing and treating an inflammatory diseases associated with tryptase activity comprising administering to said patient a pharmaceutically effective amount of a compound of formula I.

Another preferred embodiment of the invention is a method for preventing and treating late phase bronchoconstriction associated with chronic asthma comprising administering to said patient a pharmaceutically effective amount of a compound of formula I.

Another preferred embodiment of the invention is a method for treating a patient suffering from a disease state capable of being modulated by inhibiting tryptase activity comprising administering to said patient a pharmaceutically effective amount of a compound of formula I, wherein said disease state is selected from the group consisting of immunomediated inflammatory disorders associated with tryptase activity, such as rheumatoid arthritis, osteoarthritis, gouty arthritis, rheumatoid spondylitis, diseases of joint cartilage destruction, ocular conjunctivitis, vernal conjunctivis, inflammatory bowel disease, asthma, allergic rhinitis, and interstitial lung diseases.

Another preferred embodiment of the invention is a method for treating a patient suffering from a disease state capable of being modulated by inhibiting tryptase activity comprising administering to said patient a pharmaceutically effective amount of a compound of formula I, wherein said disease state is selected from the group consisting of fibrosis, sceleroderma, pulmonary fibrosis, liver cirrhosis, myocardial fibrosis, neurofibromas, hypertrophic scars, and various dermatological conditions, for example, atopic dermatitis and psoriasis.

Another preferred embodiment of the invention is a method for treating a patient suffering from a disease state capable of being modulated by inhibiting tryptase activity comprising administering to said patient a pharmaceutically effective amount of a compound of formula I, wherein said disease state is selected from the group consisting of myocardial infarction, stroke, angina and other consequences of atherosclerotic plaque rupture; as well as periodontal disease, diabetic retinopathy, tumor growth, anaphylaxis, multiple sclerosis, peptic ulcers, and syncytial viral infections.

Another preferred embodiment of the invention is a method of inhibiting tryptase activity comprising contacting a tryptase inhibitory amount of a compound of formula I with a composition containing tryptase.

Another preferred embodiment of the invention is a pharmaceutical composition comprising a pharmaceutically acceptable amount of the compound of formula I and a pharmaceutically acceptable carrier.

Another preferred embodiment of the invention is a method of treating a patient suffering from a disease state capable of being modulated by inhibiting tryptase activity comprising administering to a patient, in need thereof, a compound of formula I or a pharmaceutically acceptable salt thereof, and optionally at least one compound selected from the group consisting of a β-adrenergic agonist compound, an anti-inflammatory corticosteroid compound, an anticholinergics compound, and an anti-inflammatory compound, or a pharmaceutically acceptable salt thereof, wherein said β-adrenergic agonist compound is selected from the group consisting of albuterol, terbutaline, formoterol, fenoterol, and prenaline; said anti-inflammatory corticosteroid compound is selected from the group consisting of beclomethasone, triamcinolone, flurisolide, and dexamethasone; said anticholinergics compound is ipratropium bromide; and said anti-inflammatory compound is selected from the group consiting of sodium cromoglycate and nedocromil sodium.

Another further preferred embodiment of the invention is a pharmaceutical composition comprising a compound of formula I, and one or more of the following: a β-adrenergic agonist compound, an anti-inflammatory corticosteroid compound, an anticholinergics compound, or an anti-inflammatory compound, and a pharmaceutically acceptable carrier.

Another further preferred embodiment of the invention is an aerosol composition for treating a patient suffering from a disease state capable of being modulated by inhibiting tryptase activity comprising a compound of formula I and an aerosolized pharmaceutically acceptable carrier or solution or dry powder.

Another further preferred embodiment of the invention is a pharmaceutical kit for treating or preventing a a disease state capable of being modulated by inhibiting tryptase activity, said kit comprising a plurality of separate containers, wherein at least one of said containers contains a compound of formula I and at least another of said containers contains one or more compounds selected from the group consisting of a β-adrenergic agonist compound, an anti-inflammatory corticosteroid compound, an anticholinergics compound, and an anti-inflammatory compound, and said containers optionally contain a pharmaceutical carrier.

Another preferred embodiment of the invention is a method for treating a patient suffering from a disease state capable of being modulated by inhibiting production of Factor Xa comprising administering to said patient a pharmaceutically effective amount of a compound of formula I.

Another preferred embodiment of the invention is a method of inhibiting factor Xa comprising contacting a Factor Xa inhibitory amount of a compound of formula I with a composition containing Factor Xa.

Another preferred embodiment of the invention is a method of inhibiting the formation of thrombin comprising contacting Factor Xa inhibitory amount of a compound of formula I with a composition containing Factor Xa.

Another preferred embodiment of the invention is a method for treating a patient suffering from a physiological condition capable of being modulated by inhibiting production of Factor Xa comprising administering to said patient a pharmaceutically effective amount of a compound of formula I, wherein the physiological condition is selected from the group consisting of venous vasculature, arterial vasculature, abnormal thrombus formation, acute myocardial infarction, unstable angina, thromboembolism, acute vessel closure associated with thrombolytic therapy, percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee and hip surgery, a risk of pulmonary thromboembolism, or disseminated systemic intravascular coagulopathy occurring in vascular systems during septic shock, certain viral infections and cancer.

Another further preferred embodiment of the invention is a pharmaceutical composition comprising a compound of formula I, and one or more of the following: a cardioprotective agent, a direct thrombin inhibitor, an anticoagulant, an antiplatelet agent or fibrinolytic agent, selected from: anti-coagulants such as warfarin, heparin or low molecular weight heparin; synthetic pentasaccharides; anti-platelet agents such as aspirin, piroxicam or ticlopidine; direct thrombin inhibitors (e.g. boroarginine derivatives, hirudin or argatroban (Novastan®)); fibrinogen receptor antagonists; statins/fibrates; or fibrinolytic agents (thrombolytic agents) such as tissue plasminogen activator, anistreplase (Eminase®), urokinase or streptokinase, Factor Xa inhibitors or Factor VIIa inhibitors; and a pharmaceutically acceptable carrier.

Another further preferred embodiment of the invention is a pharmaceutical kit for treating or preventing a disease state capable of being modulated by inhibiting Factor Xa activity, said kit comprising a plurality of separate containers, wherein at least one of said containers contains a compound of formula I and at least another of said containers contains one or more compounds selected from the group consisting of a cardioprotective agent, a direct thrombin inhibitor, an anticoagulant, anantiplatelet or fibrinolytic agent, and said containers optionally contain a pharmaceutical carrier.

A preferred compound aspect of the invention is the compound of formula I wherein ===== is a single bond.

A preferred compound aspect of the invention is the compound of formula I wherein =====is a double bond.

A preferred compound aspect of the invention is the compound of formula I wherein $X^a$ and $X^b$ are hydrogen and $X^c$ is selected from the group consisting of, $R^4R^5N—$, (hydroxy)HN—, (alkoxy)HN—, $R^6O—$, $R^4R^5NCO—$, $R^4R^5NSO_2—$, $R^6CO—$, halo, cyano, nitro $R^7(O)C(CH_2)_q—$, and

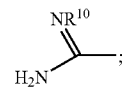

more preferably, $X^c$ is

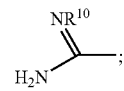

and $R^{10}$ is hydrogen, $R^{11}O—$, or HO—.

A further preferred compound aspect of the invention is the compound of formula I wherein
Z is a carbon atom;

is a 6-membered azaheterocyclyl or a 6-membered azaheterocyclenyl group; and $R^1$ and $R^2$ are hydrogen.

A further preferred compound aspect of the invention is the compound of formula I wherein Z is a nitrogen atom;

is a 6-membered azaheterocyclyl or a 6-membered azaheterocyclenyl group; ===== is a single bond; and $R^1$ and $R^2$ are hydrogen.

A further preferred compound aspect of the invention is the compound of formula I wherein Z is a nitrogen atom;

is a 6-membered azaheterocyclyl or a 6-membered azaheterocyclenyl group; ===== is a single bond; and $R^1$ is selected from the group consisting of hydrogen —$CH_2OR^{12}$, —$CH_2SR^{12}$, —$CO_2R^{13}$, —$C(O)R^{13}$ and —$CONR^{13}R^{13}$.

A further preferred compound aspect of the invention is the compound of formula I wherein Z is a carbon atom;

is a 6-membered azaheterocyclyl or a 6-membered azaheterocyclenyl group; and $R^1$ is selected from the group consisting of hydrogen —$CH_2OR^{12}$, —$CH_2SR^{12}$, —$CO_2R^{13}$, —$C(O)R^{13}$ and —$CONR^{13}R^{13}$.

A further preferred compound aspect of the invention is the compound of formula I wherein Z is a carbon atom;

is a 6-membered azaheterocyclenyl group; ===== is a double bond; and $R^1$ and $R^2$ are hydrogen.

A preferred compound aspect of the invention is a compound of formula I wherein $R^3$ is aryl, heteroaryl or heterocyclyl; more preferably, $R^3$ is substituted phenyl.

A further preferred compound aspect of the invention is a compound of formula I wherein $R^3$ is optionally substituted (phenyl substituted aralkyl), optionally substituted (heteroaryl substituted aralkyl), optionally substituted (phenyl substituted heteroaralkyl) or optionally substituted (heteroaryl substituted heteroaralkyl), (wherein the term "optionally substituted" before the term in the parenthesis, denote that the phenyl, heteroaryl, aralkyl, or heteroaralkyl portions thereof could be further substituted as noted per their definitions).

A further preferred compound aspect of the invention is a compound of formula I wherein $R^3$ is optionally substituted (phenyl substituted aralkenyl), optionally substituted (heteroaryl substituted aralkenyl), optionally substituted (phenyl substituted heteroaralkenyl) or optionally substituted (heteroaryl substituted heteroaralkenyl), (wherein the term "optionally substituted" before the term in the parenthesis, denote that the phenyl, heteroaryl, aralkenyl or heteroaralkenyl portions thereof could be further substituted as noted per their definitions).

A further preferred compound aspect of the invention is a compound of formula I wherein $R^3$ is optionally substituted (phenyl substituted aralkynl), optionally substituted (heteroaryl substituted aralkynl), optionally substituted (phenyl substituted heteroaralkynl) or optionally substituted (heteroaryl substituted heteroaralkynl), (wherein the term "optionally substituted" before the term in the parenthesis, denote that the phenyl, heteroaryl, aralkynl, heteroaralkynl portions thereof could be further substituted as noted per their definitions).

A more preferred compound aspect of the invention is a compound of formula I wherein $R^3$ is optionally substituted (phenyl substituted phenyl), optionally substituted (heteroaryl substituted phenyl), optionally substituted (phenyl substituted heteroaryl) or optionally substituted (heteroaryl substituted heteroaryl), (wherein the term "optionally substituted" before the term in the parenthesis, denote that the phenyl or heteroaryl portions thereof could be further substituted as noted per their definitions).

A preferred compound aspect of the invention is the compound of formula I wherein $R^1$ is hydrogen, —$CO_2R^{12}$, —$C(O)R^{12}$, —$CH_2OR^{13}$ or —$CH_2SR^{13}$; more preferred is hydrogen, —$CO_2R^{12}$, —$CH_2OR^{13}$ or —$CH_2SR^{13}$; yet more preferred is hydrogen, —$CO_2R^{12}$ or —$CH_2OR^{13}$ and $R^{12}$ and $R^{13}$ are hydrogen or lower alkyl.

Another preferred compound aspect of the invention is the compound of formula I wherein $X^c$ is a

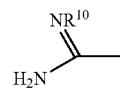

moiety and

is an aryl group, a monocyclic heteroaryl group; more preferably, $X^c$ is

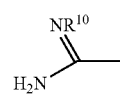

and is in the meta position with respect to the position of attachment of the

moiety to the

moiety.

Another preferred compound aspect of the invention is the compound of formula I wherein

is aryl or a monocyclic heteroaryl group; and $X^c$ is selected from the group consisting of, $R^4R^5N—$, (hydroxy)HN—, (alkoxy)HN—, $R^6O—$, $R^4R^5NCO—$, $R^4R^5NSO_2—$, $R^6CO—$, halo, cyano, nitro $R^7(O)C(CH_2)_q—$, and

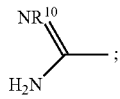

more preferably $X^c$ is

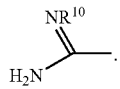

Another preferred compound aspect of the invention is the compound of formula I wherein

is a bicyclic azaheteroaryl group which includes a first proximal ring that is attached to the

moiety and a ring distal to said first ring; $X^c$ is $R^4R^5N—$, (hydroxy)HN—, or (alkoxy)HN—, and $X^c$ is in the alpha position to a nitrogen atom in said distal ring; for example,

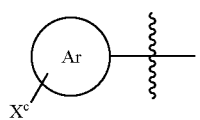

may be represented by a formula selected from the group consting of

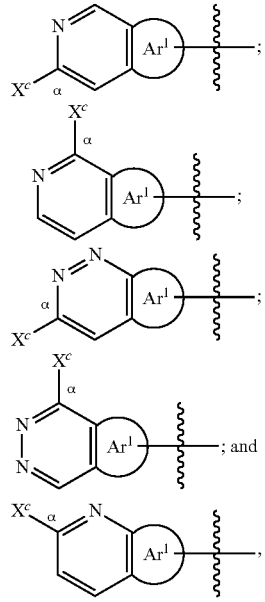

wherein $Ar^1$ is the proximal ring portion of the bicyclic heteroaryl group.

Species according to the invention are selected from the following:
3-{1-[4-(6-Oxo-1,6-dihydropyridine-3-yl)-benzoyl]-1,2,3,6-tetrahydropyridin-4 yl}benzamidine;
3-{1-[4-(1-Oxypyridin-2-yl)-benzoyl]-1,2,3,6-tetrahydropyridin-4 yl}benzamidine;
3-{1-[4-(1-Oxypyridin-4-yl)-benzoyl]-1,2,3,6-tetrahydropyridin-4-yl}benzamidine;
3-{1-[4-(6-Oxo-1,6-dihydropyridine-3-yl)-benzoyl]-piperidin-4-yl}benzamidine;
3-{1-[4-(1-Oxypyridin-4-yl)-benzoyl]-piperidin-4-yl}benzamidine;
3-{1-[4-(1-Oxypyridin-2-yl)-benzoyl]-piperidin-4-yl}benzamidine;
3-[1-(4-Pyridine-2-yl-benzoyl)-1,2,3,6-tetrahydropyridin-4-yl]benzamidine;
3-[1-(4-Pyridin-3-yl-benzoyl)-1,2,3,6-tetrahydropyridin-4-yl]benzamidine;
3-[1-(4-Pyridin-4-yl-benzoyl)-1,2,3,6-tetrahydropyridin-4-yl]benzamidine;
3-{1-[4-(5-Bromofuran-2-yl)-benzoyl]-1,2,3,6-tetrahydropyridin-4-yl}benzamidine;
3-{1-[4-(5-Chlorothiophen-2-yl)-benzoyl]-1,2,3,6-tetrahydropyridin-4-yl}benzamidine;
3-{1-(4-Thiophen-2-yl-benzoyl)-1,2,3,6-tetrahydropyridin-4-yl}benzamidine;
3-{1-[3-(5-Chlorothiophen-2-yl)-acryloyl)-1,2,3,6-tetrahydropyridin-4-yl}benzamidine;
3-[1-(4-{2-[(2-Dimethylaminoethyl)methylamino]pyrimidin-4-yl}benzoyl)-1,2,3,6-tetrahydropyridin-4-yl}benzamidine;
3-(1-{4-[2-(2-Dimethylaminoethyl)-6-oxo-1,6-dihydropyridin-3-yl]benzoyl}-1,2,3,6-tetrahydropyridin-4-yl)benzamidine;
3-[1-(4-Pyrimidin-2-ylbenzoyl)-1,2,3,6-tetrahydropyridin-4-yl]-benzamidine;
3-[1-(4-Pyrazin-2-ylbenzoyl)-1,2,3,6-tetrahydropyridin-4-yl]-benzamidine;

3-[1-(4'-Sulfamoylbiphenyl-4-carbonyl)-1,2,3,6-tetrahydro-pyridin-4-yl]-benzamidine;
3-[1-(3'-Sulfamoylbiphenyl-4-carbonyl)-1,2,3,6-tetrahydro-pyridin-4-yl]-benzamidine;
3-{1-[4-(6-Methoxypyridazin-3-yl)benzoyl]-1,2,3,6-tetrahydropyridin-4-yl]-benzamidine;
3-{1-[4-(6-Oxo-1,6dihydropyridazin-3-yl)benzoyl]-1,2,3,6-tetrahydropyridin-4-yl]-benzamidine;
3-{1-[4-(2-Aminopyrimidin-5-yl)benzoyl]-1,2,3,6-tetrahydropyridin-4-yl]-benzamidine;
3-{1-[4-(6-Methoxypyridin-3-yl)benzoyl]-1,2,3,6-tetrahydropyridin-4-yl]-benzamidine;
3-[1-(4-(Pyrimidin-5-ylbenzoyl)-1,2,3,6-tetrahydropyridin-4-yl]-benzamidine;
3-[1-(4-Pyridin-2-ylbenzoyl)-piperidin-4-yl]benzamidine;
3-[1-(4-Pyridin-3-ylbenzoyl)-piperidin-4-yl]benzamidine;
3-[1-(4-Pyridin-4-ylbenzoyl)-piperidin-4-yl]benzamidine;
3-{1-[4-(6-Methoxypyridin-3-yl)benzoyl]-piperidin-4-yl}benzamidine;
3-{1-[4-(6-Methoxypyridazin-3-yl)benzoyl]-piperidin-4-yl}benzamidine;
3-{1-[4-(6-Oxo-1,6-dihydropyridazin-3-yl)benzoyl]-piperidin-4-yl}benzamidine;
5-{4-[4-(1-Aminoisoquinolin-7-yl)piperidine-1-carbonyl]phenyl}-1H-pyridin-2-one;
5-[4-(1-Aminoisoquinolin-7-yl)piperidine-1-carbonyl]-1'H-[2,3']bipyridinyl-6'-one;
[4-(1-Aminoisoquinolin-7-yl)piperidin-1-yl][2-fluoro-4-(6-methoxypyridin-3-yl)phenyl]methanone;
[4-(1-Aminoisoquinolin-7-yl)piperidin-1-yl](2-fluoro-4-pyridin-3-ylphenyl)methanone;
4'-[4-(1-Aminoisoquinolin-7-yl)piperidine-1-carbonyl]biphenyl-3-carboxylic acid amide;
[4-(1-Aminoisoquinolin-7-yl)piperidin-1-yl][5-(6-methoxypyridin-3-yl)thiophen-2-yl]]methanone;
5-{4-[4-(1-Aminoisoquinolin-7-yl)piperidine-1-carbonyl]-3-fluorophenyl}-1H-pyridin-2-one;
5-{5-[4-(1-Aminoisoquinolin-7-yl)piperidine-1-carbonyl]thiophen-2-yl}-1H-pyridin-2-one;
5-{4-[4-(1-Aminoisoquinolin-7-yl)-3,6-dihydro-2H-pyridine-1-carbonyl]phenyl}-1H-pyridin-2-one;
[4-(1-Aminoisoquinolin-7-yl)-3,6-dihydro-2H-pyridin-1-yl](4-pyridin-4-ylphenyl)methanone;
[4-(1-Aminoisoquinolin-7-yl)piperidin-1-yl][4-(6-methoxypyridin-3-yl)phenyl]methanone;
[4-(1-Aminoisoquinolin-7-yl)piperidin-1-yl](4-pyridin-3-ylphenyl)methanone;
[4-(1-Aminoisoquinolin-7-yl)piperidin-1-yl](6'-methoxy-[2,3']bipyridin-5-yl)methanone;
5-{4-[4-(4-Amino-1H-pyrrolo[3,2-c]pyridin-2-yl)piperidine-1-carbonyl]phenyl}-1H-pyridin-2-one;
5-[4-(4-Amino-1H-pyrrolo[3,2-c]pyridin-2-yl)piperidine-1-carbonyl]-1'H-[2,3']bipyridinyl-6'-one;
3-[1-(5-Phenylethyl-pyridine-3-carbonyl)-piperidin-4-yl]-benzamidine;
3-[1-(5-Phenylethynyl-pyridine-3-carbonyl)-1,2,3,6-tetrahydropyridin-4-yl]-benzamidine;
3-[1-(5-Phenylethynyl-pyridine-3-carbonyl)-piperidin-4-yl]-benzamidine; and
3-[4-(5-Phenylethyl-pyridine-3-carbonyl)-piperazin-1-yl]-benzamidine.

It is to be understood that this invention covers all appropriate combinations of the particular and preferred groupings referred to herein.

Compounds of Formula I, wherein Z is a carbon atom, may be prepared by the application or adaptation of known methods, by which is meant methods used heretofore or described in the literature, or by methods according to this invention herein.

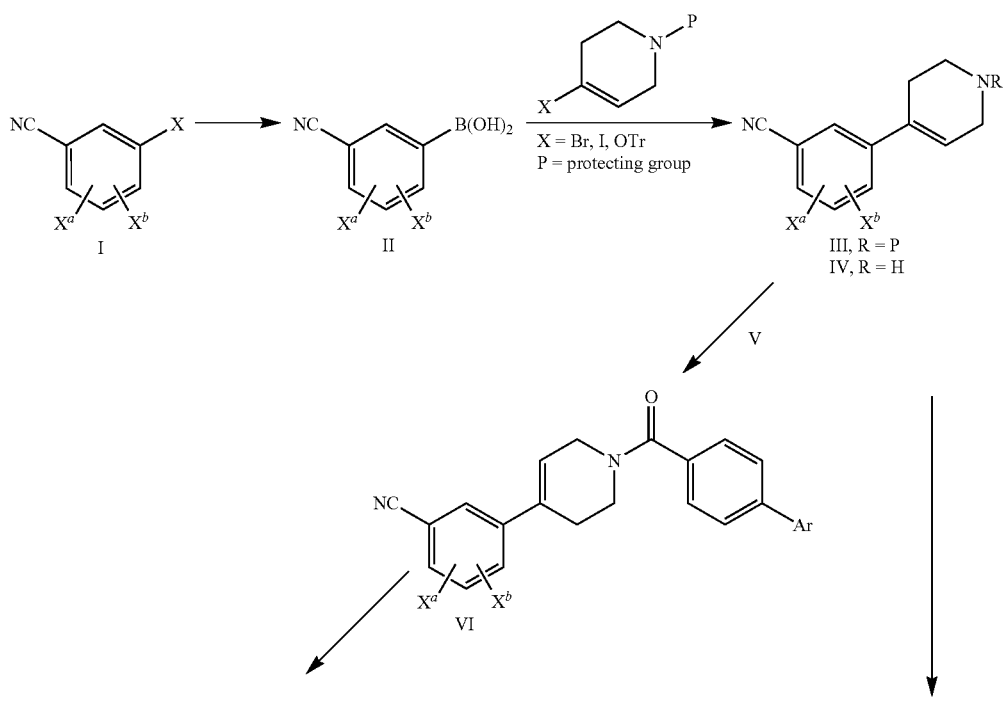

Scheme 1

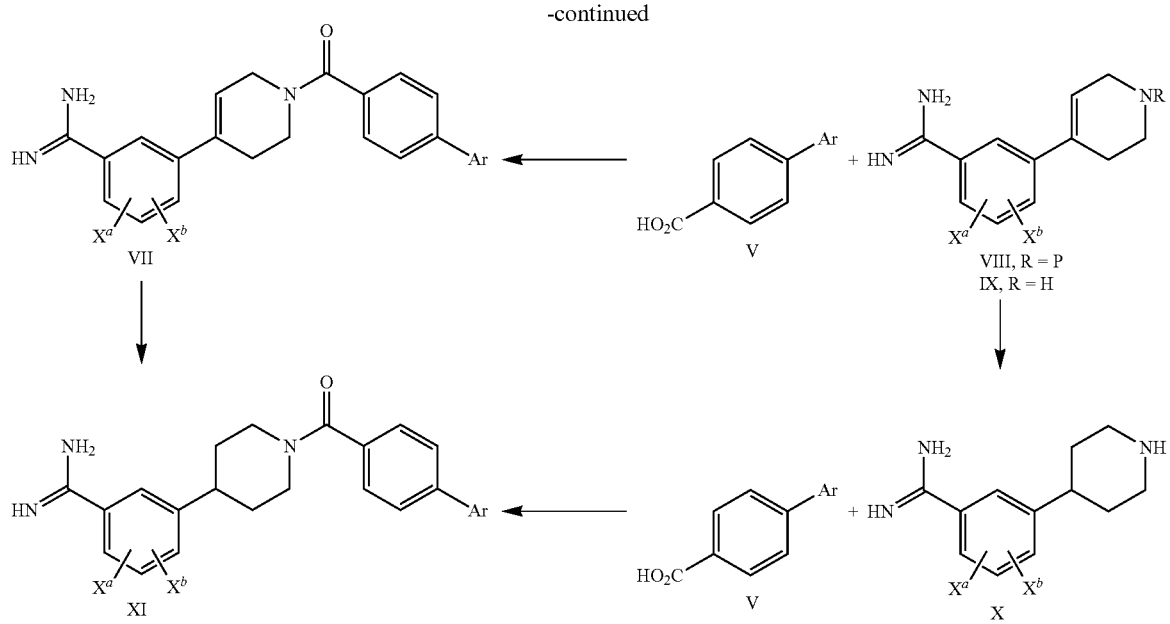

As illustrated in Scheme 1, an optionally substituted halobenzonitrile I is treated with an alkyl lithium in an aprotic solvent at low temperature followed by a trialkylborate to give compound II. A suitably activated coupling partner, such as protected 4-trifluoromethyl-sulfonyloxy-1,2,3,6-tetrahydropyridine, prepared by published methods, and compound II are dissolved in a polar solvent such as acetonitrile and treated with an aqueous base such as sodium carbonate and a palladium catalyst such as palladium tetrakistriphenylphosphine at elevated temperature (80-100° C.) for about 0.5 to 2 hours. The protected 1,2,3,6-tetrahydropyridinyl benzonitrile III so obtained can be processed in a number of ways to obtain compounds of the current invention.

The nitrogen protecting group of compound III (i. e. P) can be removed as appropriate to obtain compound IV; for example if the nitrogen protecting group is a BOC group, III is treated with a mineral acid such as HCl in ethyl acetate to obtain IV as the HCl salt. This material can be reacted with an aryl carboxylic acid such as V in the presence of base and a suitable coupling reagent such as TBTU to obtain Compound VI. Compound VI may then be converted to the benzamidine VII by treatment with Pinner conditions (HCl/ROH, wherein ROH can be methanol or ethanol) followed by ammonolysis in protic solvents such as methanol at ambient temperature to 65° C.

Alternatively compound III wherein P is a BOC group can be treated under Pinner conditions followed by ammonolysis to yield compound IX directly. When P is an acid stable protecting group the protecting group may be removed in a separate step immediately following preparation of amidine VIII using methods described above. In either case compound IX is treated with enough base to generate the free amine and aryl carboxylic acid V and a coupling reagent such as TBTU to give compounds VII.

Compounds of the invention such as XI can be obtained from the previously described intermediates IX by reduction of the double bond by any one of several reducing reagents such as palladium on carbon under a hydrogen gas atmosphere. Subsequent coupling with aryl carboxylic acid V as described above yields compounds XI. Alternatively compound VII may be reduced as a final step to give compound XI. It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

In addition, as illustrated in Scheme 2, an optionally substituted-3-(4-bromophenyl)acrylic acid XII is converted to a suitably activated acid anhydride intermediate, and treated with sodium azide to give compound XIII. This material undergoes a thermally induced Curtius rearrangement, and base catalyzed cyclization to give isoquinolone XIV. Conversion of XIV to the chloride XV, and subsequent lithiation and treatment with trialkyl borate gives compound XVI. A suitably activated coupling partner, such as protected 4-trifluorosulfonyloxy-1,2,3,6-tetrahydropyridine XVII and compound XVI are subjected to standard Suzuki coupling conditions to give the key intermediate XVIII. Compound XVIII can either be deprotected to give compound XIX, or can be subjected to ammonolysis conditions to give compound XXI. Compound XIX can be reacted with an appropriate carboxylic acid derivative, pre-activated with a suitable coupling agent such as TBTU, to give compound XX. Ammonolysis of XX gives one potential final product—compound XXIV. Compound XXIV can be carefully reduced with selective reduction conditions, such as H$_2$/palladium on carbon, to give final product XXV. Compound XXI (previously obtained from XVIII) can be deprotected to give compound XXII. Compound XXII can either be reduced as described above to give compound XXIII; or alternatively, coupled with the appropriate carboxylic acid to give final product XXIV. Compound XXIII can be coupled with the appropriate carboxylic acid (again, as previously described) to give final product XXV.

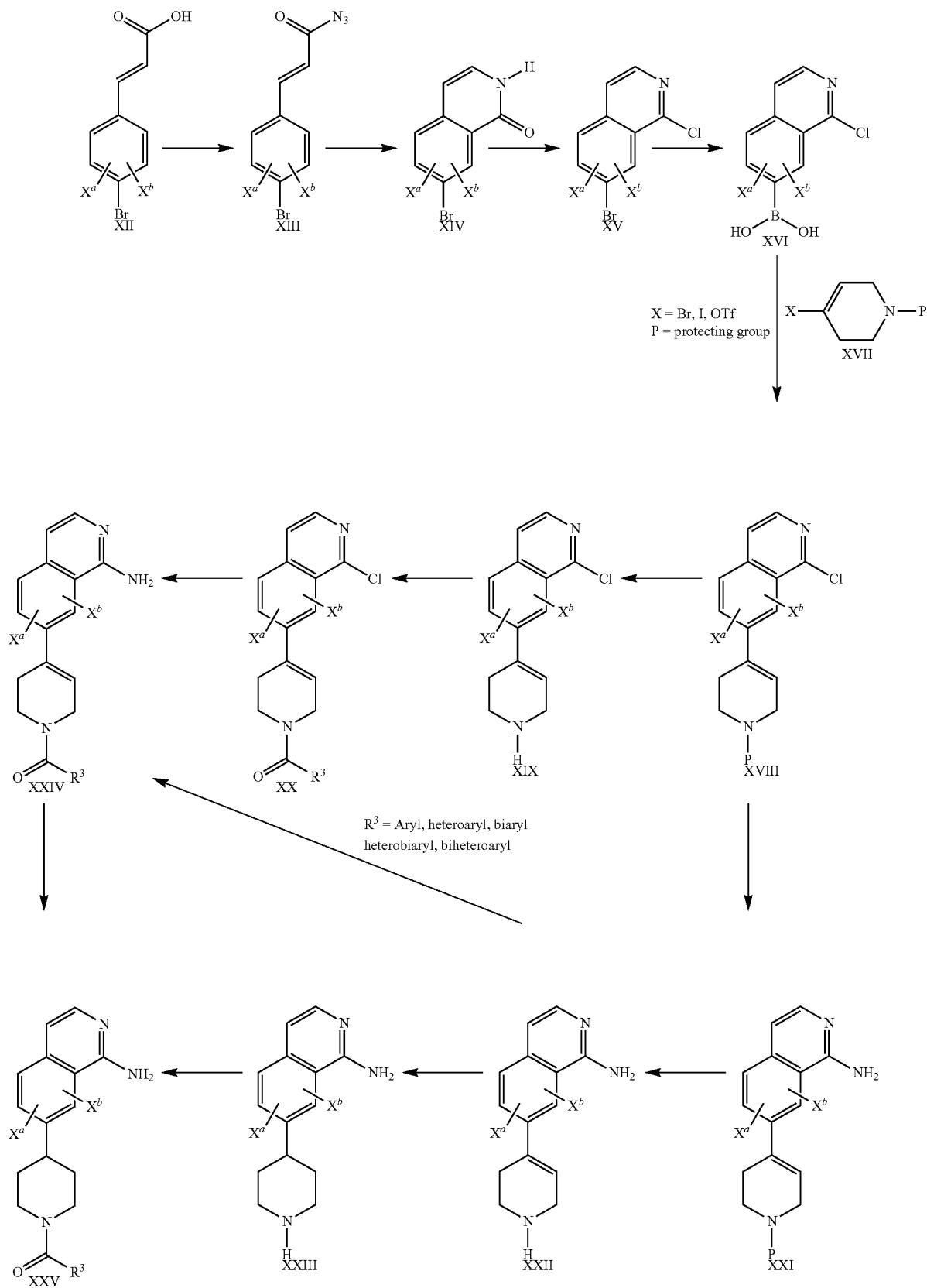

Compounds of Formula I, wherein Z is a nitrogen atom, can be prepared by the application or adaptation of known methods, by which is meant methods used heretofore or described in the literature, or by methods according to this invention herein.

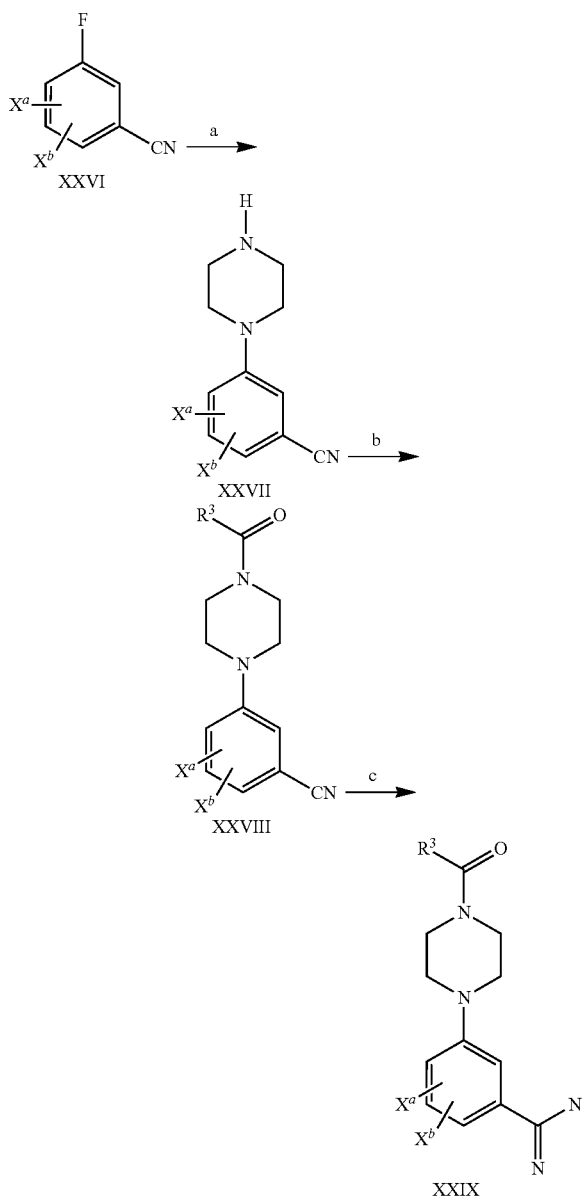

$X^a$, $X^b$=ring system substituent; $R^3$=aryl, heteroaryl, alkyl, cycloalkyl, heterocyclyl. Reagents: a) piperazine, DMSO, 100° C.; b) $R^3CO_2H$, O-(7-Azabenzotriazol-1-yl)-N,N,N,N-tetramethyluronium hexafluorophosphate (HATU), Diisopropylethylamine (DIPEA), DMF; c) HCl(g), MeOH then $NH_3$(g), MeOH.

Scheme 3

As illustrated in Scheme 3 above, an appropriately substituted fluorobenzonitrile compound of formula XXVI can be treated with an optionally substituted piperazine compound, in dimethylsulphoxide (20 ml) and heated at 100° C. for 48 hours under an atmosphere of nitrogen, to afford a piperazine intermediate compound of formula XXVII. The piperazine intermediate compound of formula XXVII can then be isolated using known purification techniques, for example, flash chromatography.

The isolated piperazine intermediate compound of formula XXVII is then reacted with a suitable carboxylic acid compound of formula $R^3COOH$ in anhydrous dimethylformamide, in the presence of HATU and diisopropylethylamine, at ambient temperature for 18 hours, to afford the desired amide intermediate compound of formula XXVIII.

A methanolic solution of an amide intermediate compound of formula XXVIII is cooled to 0° C. and saturated with hydrogen chloride gas. The reaction vessel is sealed and allowed to stand at 0° C. for 18 hours. The reaction mixture is concentrated to dryness under vacuum, redissolved in methanol (20 ml) and cooled to 0° C. The solution is saturated with ammonia gas and the vessel sealed before being allowed to stand at 0° C. for 48 hours. The reaction mixture is then concentrated to dryness under vacuum and the desired compound XXIX is isolated by known purification techniques.

The compounds of the present invention are useful in the form of the free base or acid or in the form of a pharmaceutically acceptable salt thereof. All forms are within the scope of the invention.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-B-hydroxynaphthoates, gentisates, mesylates, isethionates and di-p-toluoyltartrates-methanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The base addition salts of the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quarternarization results in the nitrogen moiety becoming positively charged and having a negative counter ion associated therewith.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The starting materials and intermediates are prepared by the application or adaptation of known methods, for example methods as described in the Reference Examples or their obvious chemical equivalents, or by methods according to this invention.

The present invention is further exemplified but not limited by the following illustrative examples which illustrate the preparation of the compounds according to the invention.

In the nuclear magnetic resonance spectra (NMR) the chemical shifts are expressed in ppm relative to tetramethylsilane. Abbreviations have the following significance: s=singlet; d=doublet; t=triplet; m=multiplet; dd=doublet of doublets; ddd=doublet of doublets of doublets; dt=doublet of triplets, b=broad.

EXAMPLE 1

3-{1-[4-(6-Oxo-1,6-dihydropyridine-3-yl)-benzoyl]-1,2,3,6-tetrahydropyridin-4 yl}benzamidine trifluoroacetate

A. 3-Cyanophenyl boronic acid

3-Bromobenzonitrile (3.6 g, 20 mmol) in anhydrous THF (100 ml) is treated with triisopropyl borate (13 ml, 56 mmol) followed by 1.6 M butyllithium in hexane (14 ml, 22 mmol) over 15 min. at −78° C. The reaction is stirred at −78° C. for 45 min . then warmed to room temperature over 60 min. The reaction mixture is poured into 40 ml 2 N HCl and the precipitated solid is collected . The filter cake is washed with water (3×) and methylene chloride (3×) to yield 3-cyanophenyl boronic acid (2.3 g, 15.6 mmol). $^1$H NMR (CDCl$_3$, 300 MHz) δ 8.4 (br, 2H), 8.13 (s, 1H), 8.07 (d, 1H), 7.85 (d, 1H), 7.55 (t, 1H). EI MS M$^+$ 147.

B. 3-(1,2,3,6-Tetrahydropyridine-4-yl)benzonitrile

3-Cyanophenyl boronic acid (3.0 g, 20.4 mmol) and 4-(trifluoromethanesulfonyloxy)-3,6-dihydro-2H-pyridine-1-carboxylic acid tert-butyl ester (7.0 g, 21.1 mmol) are dissolved in acetonitrile (100 ml) and 0.4 M aqueous sodium carbonate (100 ml). The solution is degassed and treated with palladium tetrakistriphenylphosphine (1.2 g, 1.04 mmol) at 90° C. for 1 hour. The reaction is cooled, filtered and the filtrate is concentrated to an oil. The oil is extracted with methylene chloride (3×) and the solvent is removed under vacuum. The residue is chromatographed (15% ethyl acetate/hexane) to give the title compound as a white solid (6.0 g, 21.1 mmol). This material is treated with methylene chloride (100 ml) and 40% TFA/methylene chloride (100 ml) at ambient temperature for 2 h. The solvents are removed under vacuum and the residue is chromatographed (NH$_4$OH/MeOH/CH$_2$Cl$_2$, 1:5:94) to give title compound as a brown solid contaminated with inorganic salts (4.6 g).$^1$H NMR (CDCl$_3$, 300 MHz) δ7.87 (s, 1H), 7.80 (d, 1H), 7.70 (d, 1H), 7.58 (t, 1H), 6,28 (m, 1H), 3.90 (m, 2H), 3.49 (t, 2H), 2.83 (m, 2H). EI MS M$^+$ 184.

C. 3-{1-[4-(6-Methoxypyridin-3-yl)-benzoyl]-1,2,3, 6-tetrahydropyridin-4 yl}benzonitrile 6-Methoxypyridin-3-ylbenzoic acid (0.7 g, 2.6 mmol) is treated with triethyl amine (0.7 ml, 5 mmol) and TBTU (0.95 g, 3.0 mmol) in DMF (5 ml). 3-(1,2,3,6-Tetrahydropyridin-4-yl)benzonitrile (0.9 g), prepared as above, is added to this suspension and the reaction mixture is heated to 35° C. with stirring for 1.5 h. Solvent is removed, the residue is dissolved in ethyl acetate, and the solution is washed with 1N HCl (2×5 ml). The precipitated solid, 3-{1-[4-(6-methoxypyridin-3-yl)-benzoyl]-1,2,3,6-tetrahydropyridin-4 yl}benzonitrile, is collected (0.60 g); a second crop (0.15 g) is obtained by saturating the organic layer with HCl. $^1$H NMR (DMSO) δ 8.53 (s, 1H), 8.10 (d, 1H), 7.90 (s, 1H), 7.75 (m, 4H), 4.30 (m, 3H), 6.95 (d, 1H), 6.3 (br, 1H), 4.2 (br, 2H), 3.87 (s, 3H), 3.5 (br, 2H), 2.6 (br, 2H). Ion spray MS M$^+$+1: 396.

D. 3-{1-[4-(6-Oxo-1,6-dihydropyridin-3-yl)-benzoyl]-1,2,3,6-tetrahydropyridin-4 yl}benzonitrile The combined solids from Part C (0.75 g, 1.7 mmol) are treated with pyridine hydrochloride (2.0 g, 17 mmol) and heated to 160° C. for 15 min. The reaction mixture is cooled and treated with ice water; the resulting white solid is collected and washed repeatedly with water and ethyl acetate. Vacuum drying yields the title compound as an offwhite solid (0.55 g, 1.4 mmol). Ion spray MS M$^+$+1: 382.

E. 3-{1-[4-(6-Oxo-1,6-dihydropyridine-3-yl)-benzoyl]-1,2,3,6-tetrahydropyridin-4 yl}benzamidine trifluoroacetate.

3-{1-[4-(6-Oxo-1,6-dihydropyridin-3-yl)-benzoyl]-1,2,3, 6-tetrahydropyridin-4 yl}benzonitrile from repeat runs (1.5 g, 3.9 mmol) is dissolved in methanol (200 ml), cooled in an ice bath and saturated with HCl gas. The reaction vessel is sealed and the solution is stirred overnight at ambient temperature. The solvents are removed under vacuum and the residue is re-dissolved in methanol. The solution is saturated with ammonia; the reaction vessel is sealed and stirred at ambient temperature overnight. The volatiles are removed and the residue is treated with 0.1% aqueous TFA/acetonitrile/methanol. The precipitated solid is removed and the filtrate is subjected to reverse phase HPLC purification. Lyophilization of the fractions containing product yield the title compound as an amorphous solid (0.35 g, 0.68 mmol). $^1$H NMR (DMSO) δ 11.9 (br, 1H), 9.30 (s, 2H), 9.12 (s, 2H), 7.8 (m, 4H), 7.7 (m, 4H), 7.47 (d, 2H), 6.42 (d, 1H), 6.3 (br, 1H), 4.2 (br, 2H), 3.7 (br, 2H), 2.6 (br, 2H). Ion spray MS M$^+$+1: 399.

EXAMPLE 2

3-{1-[4-(1-Oxypyridin-2-yl)-benzoyl]-1,2,3,6-tetrahydropyridin-4 yl }benzamidine trifluoroacetate 3-(1,2,3,6-Tetrahydropyridin-4-yl)benzamidine dihydrochloride (0.028 g, 0.10 mmol) is added to a solution of 4-(1-oxypyridin-2-yl)-benzoic acid (0.027 g, 0.10 mmol), triethyl amine (0.045 ml, 0.33 mmol) and TBTU (0.035 g, 0.11 mmol) in DMF (1 ml). The reaction mixture is stirred at ambient temperature for 2 h and the solvent is removed with a stream of nitrogen. The residue is purified by reverse phase HPLC to give the title compound as an amorphous solid (0.023 g, 0.037 mmol). $^1$H NMR (DMSO) δ 9.30 (s, 2H), 9.0 (s, 2H), 8.36 (m, 1H), 7.93 (d, 2H), 7.8 (m, 2H), 7.68 (m, 2H), 7.6 (m, 2H), 7.42 (m, 2H), 6.3 (br, 1H), 4.2 (br, 2H), 3.7 (br, 2H), 2.6 (br, 2H). Ion spray MS M$^+$+1: 399.

EXAMPLE 3

3-{1-[4-(1-Oxypyridin-4-yl)-benzoyl]-1,2,3,6-tetrahydropyridin-4-yl}benzamidine trifluoroacetate The title compound (0.013 g, 0.021 mmol) is prepared as described in Example 2 using 4-(1-Oxy-pyridin-4-yl)-benzoic acid (0.027 g, 0.10 mmol). $^1$H NMR (DMSO) δ 9.32 (s, 2H), 8.98 (s, 2H), 8.39 (d, 2H), 7.5-7.9 (m, 10H), 6.3 (br, 1H), 4.2 (br, 2H), 3.7 (br, 2H), 2.6 (br, 2H). Ion spray MS M$^+$+1: 399.

EXAMPLE 4

3-{1-[4-(6-Oxo-1,6-dihydropyridin-3-yl)-benzoyl]-piperidin-4-yl }benzamidine trifluoroacetate

A. 4-(3-Cyanophenyl)-3,6-dihydro-2H-pyridin-1-carboxylic acid tert-butyl ester 3-Cyanophenyl boronic acid (1.8 g, 12.2 mmol) and 4-(trifluoromethanesulfonyloxy)-3,6-dihydro-2H-pyridine-1-carboxylic acid tert-butyl ester (5.0 g, 15.2 mmol;) are dissolved in acetonitrile (60 ml) and 0.4 M aqueous sodium carbonate (60 ml). The solution is degassed and treated with palladium tetrakistriphenyl phosphine (0.81 g, 0.7 mmol) at 90° C. for 1 hour. The reaction is cooled, filtered warmed and the filtrate is concentrated to an oil. The oil is extracted with methylene chloride (3×) and the solvent is removed under vacuum. The residue is chromatographed (15% ethyl acetate/hexane) to give the title compound as a white solid (2.7 g, 9.5 mmol). $^1$H NMR (CDCl$_3$, 300 MHz) δ 7.63 (s, 1H), 7.55 (m, 2H), 7.44 (t, 1H), 6.10 (br, 1H), 4.09 (m, 2H), 3.63 (t, 2H), 2.50 (br, 2H). EI MS M$^+$+1: 285.

B. 3-(1,2,3,6-Tetrahydropyridin-4-yl)benzamidine dihydrochloride.

4-(3-Cyanophenyl)-3,6-dihydro-2H-pyridine-1-carboxylic acid tert-butyl ester (3.4 g, 12.0 mmol) is dissolved in anhydrous methanol (300 ml), cooled in an ice bath and saturated with a stream of HCl gas. The reaction vessel is sealed and the solution is stirred overnight at ambient temperature. The solvent is removed and the residue is re-dissolved in methanol (300 ml). The resulting solution is saturated with ammonia gas, the vessel is sealed and stirred overnight at room temperature. The solvent is removed in vacuo and the residue is dissolved in dilute aqueous HCl and purified by reverse phase HPLC (acetonitile/H$_2$O, 2:98). Fractions containing product are lyophilized to yield the title compound as a white solid (1.7 g, 6.2 mmol). $^1$H NMR (DMS) δ 9.48 (s, 2H), 9.38 (s, 2H), 9.15 (s, 2H), 7.90 (s, 1H), 7.80 (d, 1H), 7.73 (d, 1H), 7.58 (t, 1H), 6.39 (s, 1H), 3.76 (br, 2H), 3.3 (br, 2H), 1.9 (m, 4H). EI MS M$^+$: 201.

C. 3-Piperidin-4-ylbenzamidine dihydrochloride.

3-(1,2,3,6-Tetrahydropyridin-4-yl)benzamidine dihydrochloride (1.0 g, 5.0 mmol) is dissolved in methanol (50 ml) treated with 5% Pd on carbon and stirred overnight under an atmosphere of hydrogen gas. The reaction mixture is filtered; the filtrate is concentrated to give 3-piperidin-4ylbenzamidine dihydrochloride as a white foam (1.30 g, 4.7 mmol). $^1$H NMR (DMSO) δ 9.40 (s, 2H), 9.2 (br, 4H), 7.67 (br, 2H), 7.56 (br, 2H), 3.4 (br, 2H), 3.0 (m, 3H), 2.7 (br, 4H). Ion spray MS M$^+$+1: 204.

D. 3-{1-[4-(6-Oxo-1,6-dihydropyridine-3-yl)-benzoyl]-piperidin-4-yl}benzamidine trifluoroacetate 1-[4-(6-Oxo-1,6-dihydropyridin-3-yl)-benzoic acid (0.86 g, 4.0 mmol) is suspended in DMF (8 ml), treated with TBTU (1.4 g, 4.4 mmol), triethylamine (1.7 ml, 12 mmol) and 3-piperidinylbenzamidine dihydrochloride (1.1 g, 4.0 mmol). The reaction mixture is heated to 35° C. for 2 h. The solvent is removed and the residue is subjected to reverse phase HPLC purification to yield the title compound as an amorphous solid (1.3 g, 2.5 mmol). $^1$H NMR (DMSO) δ 11.8 (br, 1H), 9.30 (s, 2H), 9.12 (s, 2H), 7.9-7.4(m, 10H), 6.47 (d, 1H), 4.6 (br, 1H), 3.7 (br, 1H), 3.2 (br, 1H), 2.9 (m, 2H), 1.75 (m, 4H). Ion spray MS M$^+$+1: 401.

EXAMPLE 5

3-{1-[4-(1-Oxypyridin-4-yl)-benzoyl]-piperidin-4-yl}benzamidine ditrifluoroacetate 3-Piperidin-4-ylbenzamidine dihydrochloride (0.028 g, 0.10 mmol) is added to a solution of 4-(1-oxypyridin-4-yl)benzoic acid (0.027 g, 0.10 mmol), triethyl amine (0.045 ml, 0.33 mmol) and TBTU (0.035 g, 0.11 mmol) in DMF (1 ml). The reaction mixture is stirred at ambient temperature for 2 h and the solvent is removed with a stream of nitrogen. The residue is purified by reverse phase HPLC to give the title compound as an amorphous solid (0.012 g, 0.019 mmol). $^1$H NMR (DMSO) δ 9.27 (s, 2H), 8.95 (s, 2H), 8.27 (d, 2H), 7.88-7.50 (m, 10H), 4.6 (br, 1H), 3.7 (br, 1H), 3.2 (br, 1H), 2.9 (m, 2H), 1.75 (m, 4H). Ion spray MS M$^+$+1: 401.

EXAMPLE 6

3-{1-[4-(1-Oxypyridin-2-yl)-benzoyl]-piperidin-4-yl}benzamidine ditrifluoroacetate The title compound (0.028 g, 0.045 mmol) is prepared as described in example 5 using 4-(1-oxypyridin-2-yl)-benzoic acid (0.027 g, 0.10 mmol). $^1$H NMR (DMSO) δ 9.27 (s, 2H), 8.95 (s, 2H), 8.35 (m, 1H), 7.88 (d, 2H), 7.70-7.40 (m, 9H), 4.6 (br, 1H), 3.7 (br, 1H), 3.2 (br, 1H), 2.9 (m, 2H), 1.75 (m, 4H). Ion spray MS M$^+$+1: 401.

EXAMPLE 7

3-[1-(4-Pyridin-2-yl-benzoyl)-1,2,3,6-tetrahydropyridin-4-yl]benzamidine trifluoroacetate 4-Pyridin-2-yl-benzoic acid (0.012 g, 0.05 mmol) is treated in succession with a freshly prepared solution of 0.25 M TBTU in DMF (0.20 ml, 0.10 mmol), triethyl amine (0.015 ml, 0.10 mmol), and a slurry of 3-(1,2,3,6-tetrahydropyridin-4-yl)benzamidine dihydrochloride (0.011 g, 0.04 mmol) and triethylamine (0.015 ml, 0.10 mmol) in DMF (0.2 ml). The reaction mixture is stirred at 35° C. for 1.5 h and the solvent is removed with a stream of nitrogen. The residue is purified by reverse phase HPLC to give the title compound as an amorphous solid (0.007 g, 0.012 mmol). $^1$H NMR (DMSO) δ 9.30 (s, 2H), 8.90 (s, 2H), 8.70 (d, 1H), 8.13 (d, 2H), 8.02 (d, 1H), 7.95-7.53 (m, 9H), 7.42 (m, 1H), 6.3 (br, 1H), 4.2 (br, 2H), 3.7 (br, 2H), 2.6 (br, 2H). Ion spray MS M$^+$+1: 383.

In a like manner, by the method described in EXAMPLE 7, the compounds of EXAMPLES 8 to 23 are prepared:

EXAMPLE 8

3-[1-(4-Pyridin-3-yl-benzoyl)-1,2,3,6-tetrahydropyridin-4-yl]benzamidine ditrifluoroacetate.

The title compound is prepared from 3-(1,2,3,6-tetrahydropyridin-4-yl)benzamidine dihydrochloride and 4-pyridin-3-yl-benzoic acid. $^1$H NMR (DMSO) δ 9.30 (s, 2H), 8.90 (d, 3H), 8.52 (d, 1H), 8.18 (d, 1H), 7.85-7.52 (m, 9H), 6.3 (br, 1H), 4.2 (br, 2H), 3.7 (br, 2H), 2.6 (br, 2H). Ion spray MS M$^+$+1: 383.

EXAMPLE 9

3-[1-(4-Pyridin-4-yl-benzoyl)-1,2,3,6-tetrahydropyridin-4-yl]benzamidine ditrifluoroacetate The title compound is prepared from 3-(1,2,3,6-tetrahydropyridin-4-yl)benzamidine dihydrochloride and 4-pyridin-4-yl-benzoic acid. $^1$H NMR (DMSO) δ 9.30 (s, 2H), 8.90 (s, 2H), 8.70 (d, 2H), 7.95-7.53 (m, 1H), 6.3 (br, 1H), 4.2 (br, 2H), 3.7 (br, 2H), 2.6 (br, 2H). Ion spray MS M$^+$+1: 383.

EXAMPLE 10

3-{1-[4-(5-Bromofuran-2-yl)-benzoyl]-1,2,3,6-tetrahydropyridin-4-yl}benzamidine trifluoroacetate The title compound is prepared from 3-(1,2,3,6-tetrahydropyridin-4-yl)benzamidine dihydrochloride and 4-(5-bromofuran-2-yl)-benzoic acid. $^1$H NMR (DMSO) δ 9.30 (s, 2H), 8.90 (s, 2H), 7.85-7.48 (m, 8H), 7.13 (d, 1H), 6.74 (d, 1H), 6.3 (br, 1H), 4.2 (br, 2H), 2.6 (br, 2H). Ion spray MS M$^+$+1: 450,452.

EXAMPLE 11

3-{1-[4-(5-Chlorothiophen-2-yl)-benzoyl]-1,2,3,6-tetrahydropyridin-4-yl}benzamidine trifluoroacetate The title compound is prepared from 3-(1,2,3,6-tetrahydropyridin-4-yl)benzamidine dihydrochloride and 4-(5-chlorothiophen-2-yl)-benzoic acid. $^1$H NMR (DMSO) δ 9.30 (s, 2H), 8.98 (s, 2H), 7.82-7.48 (m, 9H), 7.22 (d, 1H), 6.3 (br, 1H), 4.2 (br, 2H), 3.7 (br, 2H), 2.6 (br, 2H). Ion spray MS M$^+$+1: 422,423.

EXAMPLE 12

3-{1-(4-Thiophen-2-yl-benzoyl)-1,2,3,6-tetrahydropyridin-4-yl}benzamidine trifluoroacetate The title compound is prepared from 3-(1,2,3,6-tetrahydropyridin-4-yl)benzamidine dihydrochloride and 4-thiophen-2-yl-benzoic acid. $^1$H NMR (DMSO) δ 9.30 (s, 2H), 8.98 (s, 2H), 7.82-7.60 (m, 8H), 7.48 (d, 2H), 7.20 (t, 1H), 6.3 (br, 1H), 4.2 (br, 2H), 3.7 (br, 2H), 2.6 (br, 2H). Ion spray MS M$^+$+1: 388.

EXAMPLE 13

3-{1-[3-(5-Chlorothiophen-2-yl)-acryloyl]-1,2,3,6-tetrahydropyridin-4-yl}benzamidine trifluoroacetate The title compound is prepared from 3-(1,2,3,6-tetrahydropyridin-4-yl)benzamidine dihydrochloride and 3-(5-chlorothiophen-2-yl)-acrylic acid. ¹H NMR (DMSO) δ 9.30 (s, 2H), 9.0 (s, 2H), 7.87-7.54 (m, 5H), 7.37 (d, 1H), 7.13 (d, 1H), 6.95 (m, 1H), 6.37 (br, 1H), 4.38 (br, 1H), 4.25 (br, 1H), 3.86 (br, 1H), 3.76 (br, 1H), 2.6 (br, 2H). Ion spray MS M⁺+1: 372,374.

EXAMPLE 14

3-[1-(4-{2-[(2-Dimethylaminoethyl)methylamino]pyrimidin-4-yl}benzoyl)-1,2,3,6-tetrahydropyridin-4-yl}benzamidine ditrifluoroacetate The title compound is prepared from 3-(1,2,3,6-tetrahydropyridin-4-yl)benzamidine dihydrochloride and 4-{2-[(2-Dimethylaminoethyl)methylamino]pyrimidin-4-yl}benzoic acid. ¹H NMR (DMSO) δ 9.30 (br, 3H), 9.02 (s, 2H), 8.49 (d, 1H), 8.24 (d, 2H), 8.05 (d, 1H), 7.90-7.70 (m, 3H), 7.56 (d, 2H), 7.30 (d, 1H), 6.3 (br, 1H), 4.2 (br, 2H), 4.05 (m, 2H), 3.7 (br,2H), 3.38 (m, 4H), 3.20 (s, 3H), 2.90 (s, 6H), 2.6 (br, 2H). Ion spray MS M⁺+1: 484.

EXAMPLE 15

3-(1-{4-[2-(2-Dimethylaminoethyl)-6-oxo-1,6-dihydropyridin-3-yl]benzoyl}-1,2,3,6-tetrahydropyridin-4-yl)benzamidine ditrifluoroacetate The title compound is prepared from 3-(1,2,3,6-tetrahydropyridin-4-yl)benzamidine dihydrochloride and 4-[2-(2-dimethylaminoethyl)-6-oxo-1,6-dihydropyridin-3-yl]benzoic acid. ¹H NMR (DMSO) δ 9.49 (br, 1H), 9.30 (br, 2H), 9.0 (s, 2H), 8.20 (d, 1H), 7.90 (dd, 1H), 7.80-7.50 (m, 8H), 6.55 (d, 1H), 6.3 (br, 1H), 4.30 (m, 2H), 4.2 (br, 2H), 3.7 (br, 2H), 2.86 (s, 6H), 2.6 (br, 2H). Ion spray MS M⁺+1: 470.

EXAMPLE 16

3-[1-(4-Pyrimidin-2-ylbenzoyl)-1,2,3,6-tetrahydropyridin-4-yl]-benzamidine ditrifluoroacetate The title compound is prepared from 3-(1,2,3,6-tetrahydropyridin-4-yl)benzamidine dihydrochloride and 4-(pyrimidin-2-yl)benzoic acid. ¹H NMR (DMSO) δ 9.30 (s, 2H), 8.95 (m, 4H), 8.49 (d, 2H), 7.87-7.53 (m, 6H), 7.50 (t, 1H), 6.3 (br, 1H), 4.2 (br, 2H), 3.7 (br, 2H), 3.6 (br, 2H). Ion spray MS M⁺+1: 384.

EXAMPLE 17

3-[1-(4-Pyrazin-2-ylbenzoyl)-1,2,3,6-tetrahydropyridin-4-yl]-benzamidine ditrifluoroacetate The title compound is prepared from 3-(1,2,3,6-tetrahydropyridin-4-yl)benzamidine dihydrochloride and 4-(pyrazin-2-yl)benzoic acid. ¹H NMR (DMSO) δ 9.30 (s, 3H), 8.98 (s, 2H), 8.75 (d, 1H), 8.62 (d, 1H), 8.24 (d, 2H), 8.49 (d, 2H), 7.82-7.55 (m, 4H), 6.3 (br, 1H), 4.2 (br, 2H), 3.7 (br, 2H), 2.6 (br, 2H). Ion spray MS M⁺+1: 384.

EXAMPLE 18

3-[1-(4'-Sulfamoylbiphenyl-4-carbonyl)-1,2,3,6-tetrahydropyridin-4-yl]-benzamidine trifluoroacetate The title compound is prepared from 3-(1,2,3,6-tetrahydropyridin-4-yl)benzamidine dihydrochloride and 4'-sulfamoylbiphenyl-4-carbonic acid. ¹H NMR (DMSO) δ 9.30 (s, 2H), 8.88 (s, 2H), 7.87-7.52 (m, 12H), 7.40 (s, 2H), 6.3 (br, 1H), 4.2 (br, 2H), 3.7 (br, 2H), 2.6 (br, 2H). Ion spray MS M⁺+1: 461.

EXAMPLE 19

3-[1-(3'-Sulfamoylbiphenyl-4-carbonyl)-1,2,3,6-tetrahydropyridin-4-yl]-benzamidine trifluoroacetate The title compound is prepared from 3-(1,2,3,6-tetrahydropyridin-4-yl)benzamidine dihydrochloride and 3'-sulfamoylbiphenyl-4-carbonic acid. ¹H NMR (DMSO) δ 9.30 (s, 2H), 8.88 (s, 2H), 8.12 (s, 1H), 7.93-7.52 (m, 11H), 7.40 (s, 2H), 6.3 (br, 1H), 4.2 (br, 2H), 3.7 (br, 2H), 2.6 (br, 2H). Ion spray MS M⁺+1: 461.

EXAMPLE 20

3-{1-[4-(6-Methoxypyridazin-3-yl)benzoyl]-1,2,3,6-tetrahydropyridin-4-yl]-benzamidine trifluoroacetate The title compound is prepared from 3-(1,2,3,6-tetrahydropyridin-4-yl)benzamidine dihydrochloride and 4-(6-methoxypyridazin-3-yl)benzoic acid. ¹H NMR (DMSO) δ 9.30 (s, 2H), 8.90 (s, 2H), 8.22 (d, 1H), 8.17 (d, 2H), 7.85-7.52 (m, 6H), 7.32 (d, 1H), 6.3 (br, 1H), 4.2 (br, 2H), 4.07 (s, 3H), 3.7 (br, 2H), 2.6 (br, 2H). Ion spray MS M⁺+1: 414.

EXAMPLE 21

3-{1-[4-(6-Oxo-1,6 dihydropyridazin-3-yl)benzoyl]-1,2,3,6-tetrahydropyridin-4-yl]-benzamidine trifluoroacetate The title compound is prepared from 3-(1,2,3,6-tetrahydropyridin-4-yl)benzamidine dihydrochloride and 4-(6-oxo-1,6-dihydropyridazin-3-yl)benzoic acid. ¹H NMR (DMSO) δ 13.3 (br, 1H), 9.30 (s, 2H), 8.88 (s, 2H), 8.04 (s, 1H), 7.95-7.52 (m, 8H), 7.00 (d, 1H), 6.3 (br, 1H), 4.2 (br, 2H), 3.7 (br, 2H), 2.6 (br, 2H). Ion spray MS M⁺+1: 400.

EXAMPLE 22

3-{1-[4-(2-Aminopyrimidin-5-yl)benzoyl]-1,2,3,6-tetrahydropyridin-4-yl]-benzamidine trifluoroacetate The title compound is prepared from 3-(1,2,3,6-tetrahydropyridin-4-yl)benzamidine dihydrochloride and 4-(2-aminopyrimidin-5-yl)benzoic acid. ¹H NMR (DMSO) δ 9.30 (s, 2H), 8.90 (s, 2H), 8.60 (s, 2H), 7.85-7.50 (m, 8H), 6.85 (br, 2H), 6.3 (br, 1H), 4.2 (br, 2H), 3.7 (br, 2H), 2.6 (br, 2H). Ion spray MS M⁺+1: 399.

EXAMPLE 23

3-{1-[4-(6-Methoxypyridin-3-yl)benzoyl]-1,2,3,6-tetrahydropyridin-4-yl]-benzamidine trifluoroacetate The title compound is prepared from 3-(1,2,3,6-tetrahydropyridin-4-yl)benzamidine dihydrochloride and 4-(6-methoxypyridin-3-yl)benzoic acid. ¹H NMR (DMSO) δ 9.30 (s, 2H), 8.90 (s, 2H), 8.53 (d, 1H), 8.05 (dd, 1H), 7.82-7.52

(m, 8H), 6.90 (d, 1H), 6.3 (br, 1H), 4.2 (br, 2H), 3.88 (s, 3H), 3.7 (br, 2H), 2.6 (br, 2H). Ion spray MS M$^+$+1: 413.

EXAMPLE 24

3-[1-(4-(Pyrimidin-5-ylbenzoyl)-1,2,3,6-tetrahydro-pyridin-4-yl]-benzamidine trifluoroacetate 4-Pyrimidin-5-ylbenzoic acid (0.012 g, 0.08 mmol) is treated with triethyl amine (0.030 ml, 0.22 mmol), TBTU (0,018 g, mmol), and 3-(1,2,3,6-tetrahydropyridin-4-yl)benzamidine dihydrochloride (0.022 g, 0.08 mmol) in DMF as described in EXAMPLE 5. Standard purification yields the title compound. δ 9.30 (s, 2H), 9.21 (s, 1H), 9.18 (s, 2H), 8.98 (s, 2H), 7.90-7.53 (m, 8H), 6.3 (br, 1H), 4.2 (br, 2H), 3.7 (br, 2H), 2.6 (br, 2H). Ion spray MS M$^+$+1: 384.

EXAMPLE 25

3-[1-(4-Pyridin-2-ylbenzoyl)-piperidin-4-yl]benzamidine ditrifluoroacetate

A. 3-(1,2,3,6-Tetrahydropyridin-4-yl)benzamidine ditrifluoroacetate.

4-(3-Cyanophenyl)-3,6-dihydro-2H-pyridine-1-carboxylic acid tert-butyl ester (2.2 g, mmol) is treated as described in EXAMPLE 4, Part B. Reverse phase HPLC purification (5 to 40% acetonitrile in 0.1% aqueous trifluoroacetic acid) yields the title compound as a white solid (1.4 g, 2.6 mmol). EI MS M$^+$: 201

B. 3-Piperidin-4-ylbenzamidine ditrifluoroacetate.

3-(1,2,3,6-Tetrahydropyridin-4-yl)benzamidine ditrifluoroacetate (0.44 g, 1.02 mmol) is treated as described in EXAMPLE 2, Part D to give the title compound as a white solid. (0.44 g, 1.02 mmol). $^1$H NMR (DMSO) δ 9.30 (s, 2H), 9.02 (s, 2H), 8.80 (br, 1H), 8.60 (br, 1H), 7.70-7.53 (m, 4H), 3.37 (br, 1H), 2.95 (m, 4H), 1.90 (m, 4H). Ion spray MS M$^+$+1: 204.

C. 3-[1-(4-Pyridin-2-ylbenzoyl)-piperidin-4-yl]benzamidine ditrifluoroacetate

4-Pyridin-2-yl-benzoic acid (0.012 g, 0.05 mmol) is treated in succession with TBTU (0.017 g, 0.05 mmol), DMF (0.4 ml), triethylamine (0.030 ml, 0.20 mmol) and 3-piperidin-4-ylbenzamidine ditrifluoroacetate (0.022 g, 0.05 mmol). The reaction mixture is stirred at 35° C. for 1 h and the solvent is removed with a stream of nitrogen. The residue is purified by reverse phase HPLC to give the title compound as an amorphous white solid (0.007 g, 0.011 mmol). $^1$H NMR (DMSO) δ 9.25 (s, 2H), 8.87 (s, 2H), 8.68 (d, 1H), 8.15 (d, 2H), 8.00 (d, 1H), 7.9-7.50 (m, 7H), 7.35 (m, 1H), 4.6 (br, 1H), 3.7 (br, 1H), 3.2 (br, 1H), 2.9 (m, 2H), 1.75 (m, 4H), Ion spray MS M$^+$+1: 385.

In a like manner, by the method described in EXAMPLE 25, the compounds of EXAMPLES 26 to 30 are prepared:

EXAMPLE 26

3-[1-(4-Pyridin-3-ylbenzoyl)-piperidin-4-yl]benzamidine ditrifluoroacetate

The title compound is prepared from 3-piperidin-4-ylbenzamidine ditrifluoroacetate and 4-pyridine-3-yl-benzoic acid. $^1$H NMR (DMSO) δ 9.24 (s, 2H), 8.90 (m, 3H), 8.60 (d, 1H), 8.20 (dd, 1H), 7.80-7.48 (m, 9H), 4.6 (br, 1H), 3.7 (br, 1H), 3.2 (br, 1H), 2.9 (m, 2H), 1.75 (m, 4H). Ion spray MS M$^+$+1: 385.

EXAMPLE 27

3-[1-(4-Pyridin-4-ylbenzoyl)-piperidin-4-yl]benzamidine ditrifluoroacetate

The title compound is prepared from 3-piperidin-4-ylbenzamidine ditrifluoroacetate and 4-pyridine-4-yl-benzoic acid. $^1$H NMR (DMSO) δ 9.24 (s, 2H), 8.90 (s, 2H), 8.70 (d, 2H), 7.90-7.52 (m, 10H), 4.6 (br, 1H), 3.7 (br, 1H), 3.2 (br, 1H), 2.9 (m, 2H), 1.75 (m, 4H). Ion spray MS M$^+$+1: 385.

EXAMPLE 28

3-{1-[4-(6-Methoxypyridin-3-yl)benzoyl]-piperidin-4-yl}benzamidine trifluoroacetate The title compound is prepared from 3-piperidin-4-ylbenzamidine ditrifluoroacetate and 4-(6-methoxypyridin-3-yl)benzoic acid. $^1$H NMR (DMSO) δ 9.27 (s, 2H), 9.02 (s, 2H), 8.51 (d, 1H), 8.03 (dd, 1H), 7.75-7.50 (m, 8H), 6.88 (d, 1H), 4.6 (br, 1H), 3.87 (s, 3H), 3.7 (br, 1H), 3.2 (br, 1H), 2.9 (m, 2H), 1.75 (m, 4H). Ion spray MS M$^+$+1: 415.

EXAMPLE 29

3-{1-[4-(6-Methoxypyridazin-3-yl)benzoyl]-piperidin-4-yl}benzamidine trifluoroacetate The title compound is prepared from 3-piperidin-4-ylbenzamidine ditrifluoroacetate and 4-(6-methoxypyridazin-3-yl)benzoic acid. $^1$H NMR (DMSO) δ 9.27 (s, 2H), 8.90 (s, 2H), 8.23 (d, 1H), 8.13 (d, 2H), 7.72-7.52 (m, 6H), 7.30 (d, 1H), 4.6 (br, 1H), 4.08 (s, 3H), 3.7 (br, 1H), 3.2 (br, 1), 2.9 (m, 2H), 1.75 (m,4H). Ion spray MS M$^+$+1: 416.

EXAMPLE 30

3-{1-[4-(6-Oxo-1,6-dihydropyridazin-3-yl)benzoyl]-piperidin-4-yl}benzamidine trifluoroacetate The title compound is prepared from 3-piperidin-4-ylbenzamidine ditrifluoroacetate and 4-(6-oxo-1,6-dihydropyridazin-3-yl)benzoic acid. $^1$H NMR (DMSO) δ 13.2 (s, 1H), 9.25 (s, 2H), 8.98 (s, 2H), 8.04 (d, 1H), 7.90 (d, 2H), 7.75-7.50 (m, 6H), 7.00 (d, 1H), 4.6 (br, 1H), 3.7 (br, 1H), 3.2 (br, 1H), 2.9 (m, 2H), 1.75 (m, 4H). Ion spray MS M$^+$+1: 402.

EXAMPLE 31

5-{4-[4-(1-Aminoisoquinolin-7-yl)piperidine-1-carbonyl]phenyl}-1H-pyridin-2-one trifluoroacetate A. 3-(4-Bromophenyl)acryloyl azide 4-Bromocinnamic acid (7.45 g, 32.8 mmol) dissolved in acetone (150 mL) and stirred under nitrogen at 0° C. during addition of triethylamine (5.5 ml, 39.4 mmol), followed by ethyl chloroformate (3.76 ml, 39.4 mmol). Stirred reaction mixture at 0° C. for 1 hour, before adding a solution of sodium azide (3.19 g, 49.2 mmol) in water (16 mL) dropwise. Stirred reaction mixture at 0° C. for 1 hour, then room temperature for 1 hour, before pouring into water (1 L). The white precipitate was collected and washed repeatedly with water and dried (high vacuum, $P_2O_5$) to give 3-(4-bromophenyl)acryloyl azide (7.91 g, 31.3 mmol). $^1$H NMR (CDCl$_3$) δ 7.66 (d, 1H), 7.55 (d, 2H), 7.40 (d, 2H), 6.41 (d, 1H). ESI MS (M+1)$^+$: 251, 253 (Br).

B. 7-Bromo-2H-isoquinolin-1-one

Preheated 2 separate oil baths to 240° C. A flask containing tributylamine (6.68 g, 36.1 mmol) and diphenyl ether (80 mL) was lowered into one oil bath (A), and a flask containing 3-(4-bromophenyl)acryloyl azide (7.91 g, 31.3 mmol) and diphenyl ether (80 mL) was lowered into the other oil bath (B) [vigorous gas evolution—internal temperature must quickly reach >200° C.]. After 10 minutes, the contents of flask B are poured into flask A, and the reaction left at 230-240° C. (internal temperature) for 30 minutes. Cooled reaction mixture to ~100° C., poured into hexanes (2 L), stirred to cool to room temperature and filtered off the precipitate. Washed precipitate with methylene chloride/hexanes (ratio 1/50), dried under high vacuum to give a colorless powder (4.20 g, 18.8 mmol). $^1$H NMR (DMSO) δ 11.41 (s, 1H), 8.23 (s, 1H), 7.82 (dd, 1H), 7.62 (d, 1H), 7.20 (t, 1H), 6.54 (d, 1H). ESI MS (M+1)$^+$: 224, 226 (Br).

C. 7-Bromo-1-chloroisoquinoline

7-Bromo-2H-isoquinolin-1-one (3.0 g, 13.4 mmol), phosphorus oxychloride (8.22 g, 53.6 mmol), and chloroform (25 mL) combined in a sealed tube and heated with stirring at 100° C. for 4 hours. Cooled to ~60° C., poured into ice water (100 mL), neutralized carefully with saturated aqueous sodium hydrogencarbonate, extracted into methylene chloride and dried over magnesium sulfate. Flash column chromatography on silica gel gave the product as a pale cream solid (2.01 g, 8.3 mmol). $^1$H NMR (CDCl$_3$) δ 8.51 (d, 1H), 8.30 (d, 1H), 7.82 (dd, 1H), 7.72 (d, 1H), 7.57 (dd, 1H). ESI MS (M+1)$^+$: 242, 244, 246 (Br, Cl).

D. 1-Chloroisoquinolin-7-yl boronic acid

7-Bromo-1-chloroisoquinoline (1.38 g, 5.69 mmol) in THF (15 mL) under nitrogen, at −78° C. and triisopropyl borate (2.99 g, 15.93 mmol) added, followed by dropwise addition of n-butyllithium (7.11 mL of 1.6M in hexanes, 11.38 mmol). Allowed reaction mixture to warm to −20° C. over 30 minutes and quenched with 1N HCl (30 mL). Added triethylamine to give pH 7, presorbed solution directly onto silica and flash column chromatography on silica gel to give the product as pale yellow solid (0.78 g, 3.8 mmol). $^1$H NMR (DMSO) δ 8.73 (s, 1H), 8.48 (br s, 2H), 8.35-8.28 (m, 1H), 8.25-8.13 (m, 1H), 8.06-7.92 (m, 1H), 7.91-7.82 (m, 1H). ESI MS (M+1)$^+$: 208, 210 (Cl).

E. 4-(1-Chloroisoquinolin-7-yl)-3,6-dihydro-2H-pyridine-1-carboxylic acid tert-butyl ester 1-Chloroisoquinolin-7-yl boronic acid (0.55 g, 2.67 mmol), 4-(trifluoromethanesulfonyloxy)-3,6-dihydro-2H-pyridine-1-carboxylic acid tert-butyl ester (0.68 g, 2.05 mmol), lithium chloride (0.26 g, 6.16 mmol), 2M aqueous sodium carbonate (2.9 ml, 5.8 mmol) and acetonitrile (15 mL) were combined under nitrogen, and palladium tetrakistriphenylphosphine (0.12 g, 0.103 mmol) added. The reaction mixture was refluxed for 90 minutes, cooled to room temperature, and concentrated in vacuo to give a wet solid. Ammonium hydroxide (3 mL of 30% aqueous solution) was added, and the material partitioned between methylene chloride (150 mL) and 2M aqueous sodium carbonate (25 mL). The organic phase was separated, and the aqueous extracted successively with methylene chloride. The combined organic extracts were dried over magnesium sulfate, and purified by flash column chromatography on silica gel to give the product as a white solid (0.43 g, 1.25 mmol). $^1$H NMR (CDCl$_3$) δ 8.26-8.20 (m, 2H), 7.88-7.75 (m, 2H), 7.57 (d, 1H), 6.28 (br s, 1H), 4.20-4.12 (m, 2H), 3.76-3.66 (m, 2H), 2.75-2.62 (m, 2H), 1.56 (s, 9H). ESI MS (M+1)$^+$: 259, 261 (Cl).

F. 4-(1-Aminoisoquinolin-7-yl)-3,6-dihydro-2H-pyridine-1-carboxylic acid tert-butyl ester trifluoroacetate 4-(1-Chloroisoquinolin-7-yl)-3,6-dihydro-2H-pyridine-1-carboxylic acid tert-butyl ester (0.10 g, 0.29 mmol), anhydrous ammonium acetate (0.23 g, 3 mmol), and phenol (0.36 g, 3.8 mmol) were combined into a sealed sample tube with venting capability (septa pierced several times), and heated (with stirring) at 100° C. for 28 hours. Cooled to room temperature, dissolved in acetonitrile/water (50/50, 50 mL) and concentrated the solution down to dryness (repeated addition and concentration to azeotrope off phenol). Purified the crude by preparative reverse phase HPLC, and lyophilized the product to give an amorphous white solid (84 mg, 0.26 mmol). $^1$H NMR (CDCl$_3$) δ 7.88 (s, 1H), 7.82-7.78 (m, 1H), 7.67 (d, 1H), 7.57 (d, 1H), 6.96 (d, 1H), 6.22 (br s, 1H), 4.20-4.10 (m, 2H), 3.75-3.68 (m, 2H), 2.68-2.58 (m, 2H), 1.48 (s, 9H). ESI MS (M+1)$^+$: 326.

G. 7-(1,2,3,4-Tetrahydropyridin-4-yl)isoquinolin-1-ylamine ditrifluoroacetate 4-(1-Aminoisoquinolin-7-yl)-3,6-dihydro-2H-pyridine-1-carboxylic acid tert-butyl ester trifluoroacetate (84 mg, 0.26 mmol) was dissolved in methylene chloride (7.5 mL), and cooled at 0° C. during dropwise addition of trifluoroacetic acid (2.5 mL). After 1 hour at 0° C. the reaction mixture was concentrated to dryness and placed on high vacuum overnight to give the product as a pale yellow solid (87 mg, 0.26 mmol). $^1$H NMR (DMSO) δ 9.24-9.05 (m, 2H), 9.04-8.88 (m, 2H), 8.56 (s, 1H), 8.18-8.10 (m, 1H), 7.93 (d, 1H), 7.66 (d, 1H), 7.22 (d, 1H), 6.50 (br s, 1H), 3.90-3.78 (m, 2H), 3.52-3.35 (m, 2H), 2.85-2.71 (m, 2H). ESI MS (M+1)$^+$: 226.

H. 7-Piperidin-4-ylisoquinolin-1-ylamine ditrifluoroacetate 7-(1,2,3,4-Tetrahydropyridin-4-yl)isoquinolin-1-ylamine ditrifluoroacetate (87 mg, 0.26 mmol) dissolved in methanol (20 mL), added 5% palladium on carbon (10 mg), and stirred at room temperature under an atmosphere of hydrogen (balloon) for 5 hours [NMR monitored to ensure no over-reduction]. The catalyst was filtered off, and the filtrate concentrated to give the product as a colorless solid (80 mg, 0.25 mmol). $^1$H NMR (DMSO) δ 8.90-8.71 (m, 1H), 8.60-8.42 (m, 1H), 8.38 (s, 1H), 7.96-7.84 (m, 2H), 7.66 (d, 1H), 7.20 (d, 1H), 3.48-3.33 (m, 2H), 3.17-2.93 (m, 3H), 2.13-2.02 (m, 2H), 1.95-1.77 (m, 2H). ESI MS (M+1)$^+$: 228.

I. 4-(6-Methoxypyridin-3-yl)benzoic acid

4-Carboxybenzeneboronic acid (2.87 g, 17.3 mmol), 5-bromo-2-methoxypyridine (3.25 g, 17.3 mmol), 0.4M aqueous sodium carbonate (87 ml, 34.8 mmol) and acetonitrile (86 mL) were combined under nitrogen, and palladium tetrakistriphenylphosphine (1.00 g, 0.87 mmol) added. The reaction mixture was refluxed for 3 hours, cooled to room temperature, and filtered through celite (washed celite with 50:50 acetonitrile/water). Removed acetonitrile in vacuo, diluted residue with water (100 mL) and acidified to pH 2 with 2M HCl. The precipitate which formed was collected, washed with water, and dried under high vacuum to give the product as a white powder (3.6 g, 15.7 mmol). $^1$H NMR (DMSO) δ 12.90 (br s, 1H), 8.56 (s, 1H), 8.08 (dd, 1H), 7.98 (d, 2H), 7.75 (d, 2H), 6.94 (d, 1H), 3.90 (s, 3H). ESI MS (M+1)$^+$: 230.

J. 4-(6-Oxo-1,6-dihydropyridin-3-yl)benzoic acid 4-(6-Methoxypyridin-3-yl)benzoic acid (3.34 g, 14.6 mmol), dimethylsulfoxide (6 mL), and pyridinium hydrochloride (8.43 g, 72.9 mmol) were heated together, with stirring, at 160° C. for 15 minutes. The reaction mixture was cooled to ~90° C., and water added slowly (100 mL). The solution/suspension was cooled to 0° C., the precipitate filtered off and washed with water. The wet product was dried by azeotroping off the residual water with methanol to give the product as a white solid (2.38 g, 11.1 mmol). $^1$H NMR (DMSO) δ 7.93 (d, 2H), 7.91-7.78 (m, 2H), 7.68 (d, 2H), 6.43 (d, 1H). ESI MS (M+1)$^+$: 216.

K. 5-{4-[4-(1-Aminoisoquinolin-7-yl)piperidine-1-carbonyl]phenyl}-1H-pyridin-2-one trifluoroacetate 4-(6-Oxo-1,6-dihydropyridin-3-yl)benzoic acid (25 mg, 0.11 mmol) and diisopropylethylamine (57 mg, 0.44 mmol) were dissolved/suspended in dimethylformamide (1 mL), and TBTU (35.6 mg, 0.11 mmol) added. Left solution stirring for 15 minutes before adding a solution of 7-piperidin-4-ylisoquinolin-1-ylamine ditrifluoroacetate (50.5 mg, 0.11 mmol) and diisopropylethylamine (57 mg, 0.44 mmol) in dimethylformamide (1 mL). The reaction mixture was stirred at room temperature overnight, the solvent removed, and the residue purified by preparative reverse phase HPLC. Lyophilization gave the product as an amorphous white powder (22.3 mg, 0.042 mmol). $^1$H NMR (DMSO) δ 8.43 (s, 1H), 7.98-7.80 (m, 3H), 7.79-7.75 (m, 1H), 7.70-7.56 (m, 3H), 7.46 (d, 2H), 7.21 (d, 1H), 6.42 (d, 1H), 4.85-4.50 (m, 1H), 4.10-4.00 (m, 1H), 3.33-3.10 (m, 1H), 3.09-2.94 (m, 2H), 2.10-1.58 (m, 4H). ESI MS (M+1)$^+$: 424.

EXAMPLE 32

5-[4-(1-Aminoisoquinolin-7-yl)piperidine-1-carbonyl]-1'H-[2,3']bipyridinyl-6'-one trifluoroacetate A. 6-Methoxypyridin-3-ylboronic acid hydrochloride n-Butyllithium (13.1 mL of 1.6M in hexanes, 21 mmol) was added dropwise to a stirring solution of 5-bromo-2-methoxypyridine (3.76 g, 20 mmol) in THF (100 mL) at −100° C. under nitrogen. Left at this temperature for 1 hour, before adding triisopropylborate (11.28 g, 60 mmol) and leaving the reaction to warm to room temperature overnight. Quenched with 1N HCl (40 mL), and presorbed entire solution directly onto silica and flash columned on silica gel. Gave product as a pale yellow powder (3.01 g, 16 mmol). $^1$H NMR (DMSO) δ 8.51 (d, 1H), 8.08 (dd, 1H), 6.85 (d, 1H), 5.80 (br s, 2H), 3.84 (s, 3H). ESI MS (M+1)$^+$: 154.

B. 6-Bromonicotinic acid hydrochloride n-Butyllithium (8.0 mL of 2.5M in hexanes, 20 mmol) was added dropwise to a stirring solution of 2,5-dibromopyridine (4.74 g, 20 mmol) in THF (100 mL) at −100° C. under nitrogen. Left at this temperature for 30 minutes, before bubbling anhydrous carbon dioxide gas through the reaction mixture (for 20 minutes), and leaving to warm to −20° C. Quenched with 1N HCl (20 mL) and brine (20 mL), and extracted into ethyl acetate, dried over magnesium sulfate, concentrated to dryness. Gave product as a pale yellow powder (3.8 g, 16 mmol). $^1$H NMR (CDCl$_3$+d$_4$-MeOH) δ 8.86 (d, 1H), 8.07 (dd, 1H), 7.52 (d, 1H). ESI MS (M+1)$^+$: 202, 204.

C. 6'-Methoxy[2,3']bipyridinyl-5-carboxylic acid

The title compound is prepared as described in EXAMPLE 31, Part I, but with 6-bromonicotinic acid hydrochloride and 6-methoxypyridin-3-ylboronic acid hydrochloride as starting materials, and 10 molar equivalents of 0.4M aqueous sodium carbonate. $^1$H NMR (DMSO) δ 13.40 (br s, 1H), 9.10 (d, 1H), 8.95 (d, 1H), 8.43 (dd, 1H), 8.28 (dd, 1H), 8.09 (d, 1H), 6.95 (d, 1H), 3.91 (s, 3H). ESI MS (M+1)$^+$: 231.

D. 6'-Oxo-1',6'-dihydro-[2,3']bipyridinyl-5-carboxylic acid

The title compound is prepared as described in EXAMPLE 31, Part J, but with 6'-methoxy[2,3']bipyridinyl-5-carboxylic acid as starting material. $^1$H NMR (DMSO) δ 13.00 (br s, 1H), 12.10 (br s, 1H), 8.99 (s, 1H), 8.31-8.12 (m, 3H), 7.91 (d, 1H), 6.42 (d, 1H). ESI MS (M+1)$^+$: 217.

E. 5-[4-(1-Aminoisoquinolin-7-yl)piperidine-1-carbonyl]-1'H-[2,3']bipyridinyl-6'-one trifluoroacetate The title compound is prepared as described in EXAMPLE 31, Part K, but with 6'-oxo-1',6'-dihydro-[2,3']bipyridinyl-5-carboxylic acid as starting material. $^1$H NMR (DMSO) δ 13.08 (br s, 1H), 12.00 (br s, 1H), 9.00 (br s, 2H), 8.63 (s, 1H), 8.43 (s, 1H), 8.24-8.16 (m, 2H), 7.98-7.82 (m, 4H), 7.60 (d, 1H), 7.19 (d, 1H), 6.43 (d, 1H), 4.72-4.56 (m, 1H), 3.79-3.64 (m, 1H), 3.35-3,21 (m, 1H), 3.10-2.86 (m, 2H), 2.00-1.61 (m, 4H). ESI MS (M+1)$^+$: 426.

EXAMPLE 33

[4-(1-Aminoisoquinolin-7-yl)piperidin-1-yl][2-fluoro-4-(6-methoxypyridin-3-yl)phenyl]methanone trifluoroacetate A. 2-Fluoro-4-(6-methoxypyridin-3-yl)benzoic acid The title compound is prepared as described in EXAMPLE 31, Part I, but with 4-bromo-2-fluorobenzoic acid and 6-methoxypyridin-3-ylboronic acid hydrochloride as starting materials, and 10 molar equivalents of 0.4M aqueous sodium carbonate. $^1$H NMR (DMSO) δ 13.30 (br s, 1H), 8.59 (d, 1H), 8.11 (dd, 1H), 7.90 (t, 1H), 7.68-7.57 (m, 2H), 6.91 (d, 1H), 3.88 (s, 3H). ESI MS (M+1)$^+$: 248.

B. [4-(1-Aminoisoquinolin-7-yl)piperidin-1-yl][2-fluoro-4-(6-methoxypyridin-3-yl)phenyl]methanone trifluoroacetate The title compound is prepared as described in EXAMPLE 31, Part K, but with 2-fluoro-4-(6-methoxypyridin-3-yl)benzoic acid as starting material. $^1$H NMR (DMSO) δ 9.08-8.85 (m, 2H), 8.58 (d, 1H), 8.42 (d, 1H), 8.15-8.05 (m, 1H), 7.91 (s, 2H), 7.72-7.58 (m, 3H), 7.55-7.44 (m, 1H), 7.20 (d, 1H), 6.93

(d, 1H), 4.80-4.65 (m, 1H), 3.88 (s, 3H), 3.68-3.51 (m, 1H), 3.33-3.15 (m, 1H), 3.12 (m, 2H), 2.05-1.50 (m, 4H). ESI MS (M+1)$^+$: 457.

EXAMPLE 34

[4-(1-Aminoisoquinolin-7-yl)piperidin-1-yl](2-fluoro-4-pyridin-3-ylphenyl)methanone ditrifluoroacetate

A. 2-Fluoro-4-pyridin-3-ylbenzoic acid

The title compound is prepared as described in EXAMPLE 31, Part I, but with 4-bromo-2-fluorobenzoic acid and 3-pyridinylboronic acid as starting materials. $^1$H NMR (DMSO) δ 8.97 (d, 1H), 8.66-8.58 (m, 1H), 8.22-8.12 (m, 1H), 8.00-7.91 (m, 1H), 7.81-7.62 (m, 2H), 7.55-7.45 (m, 1H). ESI MS (M+1)$^+$: 218.

B. [4-(1-Aminoisoquinolin-7-yl)piperidin-1-yl](2-fluoro-4-pyridin-3-ylphenyl)methanone ditrifluoroacetate The title compound is prepared as described in EXAMPLE 31, Part K, but with 2-fluoro-4-pyridin-3-ylbenzoic acid as starting material. $^1$H NMR (DMSO) δ 9.02 (s, 1H), 8.66 (d, 1H), 8.42 (s, 1H), 8.26 (d, 1H), 7.98-7.86 (m, 2H), 7.84-7.66 (m, 2H), 7.64-7.50 (m, 3H), 7.20 (d, 1H), 4.72 (d, 1H), 3.65-3.52 (m, 1H), 3.35-3.18 (m, 1H), 3.12-2.86 (m, 2H), 2.03-1.55 (m, 4H). ESI MS (M+1)$^+$: 427.

EXAMPLE 35

4'-[4-(1-Aminoisoquinolin-7-yl)piperidine-1-carbonyl]biphenyl-3-carboxylic acid amide trifluoroacetate

A. 3'-Carbamoylbiphenyl-4-carboxylic acid

The title compound is prepared as described in EXAMPLE 31, Part I, but with 3-bromobenzene carboxamide as starting material. $^1$H NMR (DMSO) δ 8.20 (s, 1H), 8.12 (s, 1H), 8.03 (d, 2H), 7.93-7.80 (m, 4H), 7.61-7.52 (m, 1H), 7.48-7.43 (br s, 1H). ESI MS (M+1)$^+$: 242.

B. 4'-[4-(1-Aminoisoquinolin-7-yl)piperidine-1-carbonyl]biphenyl-3-carboxylic acid amide trifluoroacetate The title compound is prepared as described in EXAMPLE 31, Part K, but with 3'-carbamoylbiphenyl-4-carboxylic acid as starting material. $^1$H NMR (DMSO) δ 8.43 (s, 1H), 8.18 (s, 1H), 7.96-7.78 (m, 6H), 7.65-7.50 (m, 4H), 7.43 (s, 1H), 7.21 (d, 1H), 4.80-4.60 (m, 1H), 3.92-3.70 (m, 1H), 3.35-3.15 (m, 1H), 3.10-2.83 (m, 2H), 2.03-1.55 (m, 4H). ESI MS (M+1)$^+$: 451.

EXAMPLE 36

[4-(1-Aminoisoquinolin-7-yl)piperidin-1-yl][5-(6-methoxypyridin-3-yl)thiophen-2-yl]]methanone trifluoroacetate

A. 5-(6-Methoxypyridin-3-yl)thiophene-2-carboxylic acid

The title compound is prepared as described in EXAMPLE 31, Part I, but with 5-bromothiophene-2-carboxylic acid and 6-methoxypyridin-3-ylboronic acid hydrochloride as starting materials, and 10 molar equivalents of 0.4M aqueous sodium carbonate. $^1$H NMR (DMSO) δ 13.10 (br s, 1H), 8.55 (d, 1H), 8.03 (dd, 1H), 7.66 (d, 1H), 7.50 (d, 1H), 6.90 (d, 1H). ESI MS (M+1)$^+$: 236.

B. [4-(1-Aminoisoquinolin-7-yl)piperidin-1-yl][5-(6-methoxypyridin-3-yl)thiophen-2-yl]]methanone trifluoroacetate The title compound is prepared as described in EXAMPLE 31, Part K, but with 5-(6-methoxypyridin-3-yl)thiophene-2-carboxylic acid as starting material. $^1$H NMR (DMSO) δ 13.30 (br s, 1H), 9.06 (br s, 2H), 8.52 (d, 1H), 8.44 (s, 1H), 8.02 (dd, 1H), 7.95-7.87 (m, 2H), 7.60 (d, 1H), 7.49-7.43 (m, 2H), 7.18 (d, 1H), 6.89 (d, 1H), 4.52-4.42 (m, 2H), 3.87 (s, 3H), 3.28-3.01 (m, 3H), 1.96-1.88 (m, 2H), 1.77-1.60 (m, 2H). ESI MS (M+1)$^+$: 445.

EXAMPLE 37

5-{4-[4-(1-Aminoisoquinolin-7-yl)piperidine-1-carbonyl]-3-fluorophenyl}-1H-pyridin-2-one trifluoroacetate

A. 2-Fluoro-4-(6-oxo-1,6-dihydropyridin-3-yl)benzoic acid

The title compound is prepared as described in EXAMPLE 31, Part J, but with 2-fluoro-4-(6-methoxypyridin-3-yl)benzoic acid as starting material. $^1$H NMR (DMSO) δ 13.25 (br s, 1H), 12.10 (br s, 1H), 7.96-7.88 (m, 2H), 7.84 (t, 1H), 7.58-7.47 (m, 2H), 6.42 (d, 1H), ESI MS (M+1)$^+$: 234.

B. 5-{4-[4-(1-Aminoisoquinolin-7-yl)piperidine-1-carbonyl]-3-fluorophenyl}-1H-pyridin-2-one trifluoroacetate The title compound is prepared as described in EXAMPLE 31, Part K, but with 2-fluoro-4-(6-oxo-1,6-dihydropyridin-3-yl)benzoic acid as starting material. $^1$H NMR (DMSO) δ 13.12 (br s, 1H), 11.96 (br s, 1H), 9.02 (br s, 2H), 8.41 (s, 1H), 7.95-7.82 (m, 4H), 7.63-7.40 (m, 4H), 7.19 (d, 1H), 6.42 (d, 1H), 4.74-4.66 (m, 1H), 3.60-3.51 (m, 1H), 3.32-3.20 (m, 1H), 3.08-2.87 (m, 2H), 2.02-1.55 (m, 4H). ESI MS (M+1)$^+$: 443.

EXAMPLE 38

5-{5-[4-(1-Aminoisoquinolin-7-yl)piperidine-1-carbonyl]thiophen-2-yl}-1H-pyridin-2-one trifluoroacetate

A. 5-(6-Oxo-1,6-dihydropyridin-3-yl)thiophene-2-carboxylic acid

The title compound is prepared as described in EXAMPLE 31, Part J, but with 5-(6-methoxypyridin-3-yl)thiophene-2-carboxylic acid as starting material. $^1$H NMR (DMSO) δ 13.00 (br s, 1H), 12.10 (br s, 1H), 7.84 (d, 1H), 7.78 (dd, 1H), 7.63 (d, 1H), 7.36 (d, 1H), 6.41 (d, 1H). ESI MS (M+1)$^+$: 222.

B. 5-{5-[4-(1-Aminoisoquinolin-7-yl)piperidine-1-carbonyl]thiophen-2-yl}-1H-pyridin-2-one trifluoroacetate The title compound is prepared as described in EXAMPLE 31, Part K, but with 5-(6-oxo-1,6-dihydropyridin-3-yl)

thiophene-2-carboxylic acid as starting material. $^1$H NMR (DMSO) δ 13.11 (br s, 1H), 11.96 (br s, 1H), 8.98 (br s, 1H), 8.43 (s, 1H), 7.95-7.87 (m, 2H), 7.80-7.74 (m, 2H), 7.61 (d, 1H), 7.39 (d, 1H), 7.31 (d, 1H), 7.19 (d, 1H), 6.41 (d, 1H), 4.52-4.42 (m, 2H), 3.26-3.00 (m, 3H), 1.98-1.88 (m, 2H), 1.82-1.67 (m, 2H). ESI MS (M+1)$^+$: 431.

EXAMPLE 39

5-{4-[4-(1-Aminoisoquinolin-7-yl)-3,6-dihydro-2H-pyridine-1-carbonyl]phenyl}-1H-pyridin-2-one trifluoroacetate The title compound is prepared as described in EXAMPLE 31, Part K, but with 7-(1,2,3,4-tetrahydropyridin-4-yl)isoquinolin-1-ylamine ditrifluoroacetate as starting material. $^1$H NMR (DMSO) δ 8.52 (s, 1H), 8.18-8.05 (m, 1H), 7.98-7.83 (m, 3H), 7.80 (d, 1H), 7.71-7.63 (m, 3H), 7.47 (d, 2H), 7.22 (d, 1H), 6.65-6.35 (m, 2H), 4.41-4.15 (m, 2H), 3.95-3.55 (m, 2H), 2.85-2.73 (m, 2H). ESI MS (M+1)$^+$: 423.

EXAMPLE 40

[4-(1-Aminoisoquinolin-7-yl)-3,6-dihydro-2H-pyridin-1-yl](4-pyridin-4-ylphenyl)methanone ditrifluoroacetate The title compound is prepared as described in EXAMPLE 31, Part K, but with 7-(1,2,3,4-tetrahydropyridin-4-yl)isoquinolin-1-ylamine ditrifluoroacetate and 4-pyridin-4-ylbenzoic acid as starting materials. $^1$H NMR (DMSO) δ 8.82-8.70 (m, 1H), 8.53 (s, 1H), 8.18-8.05 (m, 1H), 8.03-7.83 (m, 6H), 7.65 (d, 2H), 7.22 (d, 1H), 6.64-6.31 (m, 1H), 4.42-4.38 (m, 2H), 4.36-4.10 (m, 2H), 2.78-2.63 (m, 2H). ESI MS (M+1)$^+$: 407.

EXAMPLE 41

[4-(1-Aminoisoquinolin-7-yl)piperidin-1-yl][4-(6-methoxypyridin-3-yl)phenyl]methanone trifluoroacetate The title compound is prepared as described in EXAMPLE 31, Part K, but with 4-(6-methoxypyridin-3-yl)benzoic acid as starting material. $^1$H NMR (DMSO) δ 8.53 (d, 1H), 8.43 (s, 1H), 8.08-8.02 (m, 1H), 7.98-7.87 (m, 2H), 7.76 (d, 2H), 7.63 (d, 1H), 7.53 (d, 2H), 7.21 (d, 1H), 6.92 (d, 1H), 4.68 (br s, 1H), 3.87 (s, 3H), 3.35-3.13 (m, 1H), 3.11-2.85 (m, 2H), 2.03-1.60 (m, 4H). ESI MS (M+1)$^+$: 439.

EXAMPLE 42

[4-(1-Aminoisoquinolin-7-yl)piperidin-1-yl](4-pyridin-3-ylphenyl)methanone ditrifluoroacetate The title compound is prepared as described in EXAMPLE 31, Part K, but with 4-pyridin-3-ylbenzoic acid as starting material. $^1$H NMR (DMSO) δ 8.83 (s, 1H), 8.62 (d, 1H), 8.45 (s, 1H), 8.18 (d, 1H), 7.98-7.87 (m, 4H), 7.66-7.50 (m, 4H), 7.22 (d, 1H), 4.80-4.61 (m, 1H), 3.88-3.70 (m, 1H), 3.32-3.15 (m, 1H), 3.10-2.85 (m, 2H), 2.04-1.60 (m, 4H). ESI MS (M+1)$^+$: 409.

EXAMPLE 43

[4-(1-Aminoisoquinolin-7-yl)piperidin-1-yl](6'-methoxy-[2,3']bipyridin-5-yl)methanone ditrifluoroacetate The title compound is prepared as described in EXAMPLE 31, Part K, but with 6'-methoxy[2,3']bipyridinyl-5-carboxylic acid as starting material. $^1$H NMR (DMSO) δ 8.91 (d, 1H), 8.73 (d, 1H), 8.48-8.38 (m, 2H), 8.07 (d, 1H), 8.00-7.87 (m, 3H), 7.60 (d, 1H), 7.22 (d, 1H), 6.96 (d, 1H), 4.80-4.60 (m, 1H), 3.91 (s, 3H), 3.80-3.71 (m, 1H), 3.35-3.20 (m, 1H), 3.13-2.85 (m, 2H), 2.01-1.65 (m, 4H). ESI MS (M+1)$^+$: 440.

EXAMPLE 44

5-{4-[4-(4-Amino-1H-pyrrolo[3,2-c]pyridin-2-yl)piperidine-1-carbonyl]phenyl}-1H-pyridin-2-one trifluoroacetate A. (2-Chloropyridin-4-yl)carbamic acid tert-butyl ester Sodium bis(trimethylsilyl)amide (90 mL of 1M in THF, 90 mmol) was added slowly to a stirring solution of 4-amino-2-chloropyridine (5.79 g, 45 mmol) in THF (100 mL) at room temperature under nitrogen. Left at room temperature for 15 minutes before adding dropwise a solution of di-tert-butyl dicarbonate (8.95 g, 41 mmol) in THF (50 mL). After 2 hours the solvent was removed in vacuo, and 0.1N HCl (100 mL) added to the residue, and extracted with ethyl acetate. Washed ethyl acetate with 0.1N HCl, dried organics over magnesium sulfate, and concentrated to dryness. The slightly crude yellow solid was washed with cold diethyl ether (3×20 mL) to give the pure product as a cream solid (6.43 g, 28 mmol). $^1$H NMR (CDCl$_3$) δ 8.17 (d, 1H), 7.49 (d, 1H), 7.15 (dd, 1H), 6.95 (br s, 1H), 1.51 (s, 9H). ESI MS (M+1)$^+$: 229, 331 (Cl).

B. (2-Chloro-3-methylpyridin-4-yl)carbamic acid tert-butyl ester tert-Butyllithium (29 mL of 1.7M in pentane, 50 mmol) was added dropwise to a vigorously stirring solution of (2-chloropyridin-4-yl)carbamic acid tert-butyl ester (4.57 g, 20 mmol) in THF (150 mL) at −78° C. under nitrogen. The reaction mixture was kept at this temperature for 4 hours before adding a solution of methyl iodide (3.41 g, 24 mmol) in THF (20 mL). Warmed the reaction mixture to 0° C. over 2 hours, and quenched the reaction with saturated aqueous ammonium chloride solution (100 mL). Extracted into ethyl acetate, washed with brine, dried over magnesium sulfate, and concentrated to dryness. Flash column chromatography on silica gel gave the product as a white solid (2.93 g, 12 mmol). $^1$H NMR (CDCl$_3$) δ 8.11 (d, 1H), 7.98 (d, 1H), 6.58 (br s, 1H), 2.30 (s, 3H), 1.52 (s, 9H). ESI MS (M+1)$^+$: 243, 245 (Cl).

C. 4-(Methoxymethylcarbamoyl)piperidine-1-carboxylic acid tert-butyl ester

1-[3-(dimethylamino)propyl]-3-ethylcarbodiimide hydrochloride (9.20 g, 48 mmol) was added to a stirring solution of 1-tert-butoxycarbonylisonipecotic acid (10.0 g, 43.6 mmol) in methylene chloride (200 mL) at 0° C., under nitrogen. After 5 minutes at this temperature N, O-dimethylhydroxylamine hydrochloride was added, followed by the dropwise addition of pyridine (11.39 g, 144 mmol). Warmed the reaction mixture to room temperature, and stirred for 3 hours before quenching with 1N HCl (100 mL). The organic phase was separated and washed with 1N HCl (2×100 mL), followed by saturated aqueous sodium hydrogencarbonate (2×100 mL). The organics were dried over magnesium sulfate and concentrated to dryness, to give the product as a colorless oil (8.61 g, 31.6 mmol). $^1$H NMR (CDCl$_3$) δ 4.15-4.04 (m, 2H), 3.68 (s, 3H), 3.15 (s, 3H), 2.82-2.56 (m, 3H), 1.73-1.58 (m, 4H), 1.42 (s, 9H). ESI MS (M+1)$^+$: 273.

D. 4-Chloro-2-piperidin-4-yl-1H-pyrrolo[3,2-c]pyridine n-Butyllithium (3.36 mL of 2.5M in hexanes, 8.4 mmol) was added dropwise to a stirring solution of (2-chloro-3-methylpyridin-4-yl)carbamic acid tert-butyl ester (0.971 g, 4 mmol) in THF (50 mL) at −78° C., under nitrogen. Warmed the reaction mixture to −20° C. for 15 minutes, before cooling back to −78° C. and adding a solution of 4-(methoxymethylcarbamoyl)piperidine-1-carboxylic acid tert-butyl ester (1.089 g, 4 mmol) in THF (10 mL). Warmed the reaction slowly to room temperature over 2 hours, and quenched with 1N HCl (50 mL). Extracted into ethyl acetate, washed with saturated aqueous sodium hydrogencarbonate, and dried over magnesium sulfate. Flash column chromatography gave a 1:1 mixture, by NMR, of the ring open and ring closed tautomers of the required intermediate {4-[(tert-butoxycarbonylamino-2-chloropyridin-3-yl)acetyl]piperidine-1-carboxylic acid tert-butyl ester and 2-(1-tert-butoxycarbonylpiperidin-4-yl)-4-chloro-2-hydroxy-2,3-dihydropyrrolo[3,2-c]pyridine-1-carboxylic acid tert-butyl ester}. This material (845 mg, 1.88 mmol) was dissolved in methylene chloride (40 mL) and stirred vigorously at room temperature during the dropwise addition of trifluoroacetic acid (4 mL). After 2 hours the reaction mixture was concentrated to dryness, and flash column chromatographed on silica gel with ammonium hydroxide/methylene chloride/methanol to give the pure free base product as a white powder (420 mg, 1.76 mmol). $^1$H NMR (d$_4$-MeOH) δ 7.87 (d, 1H), 7.31 (d, 1H), 6.39 (s, 1H), 3.52-3.45 (m, 2H), 3.20-3.09 (m, 3H), 2.36-2.25 (m, 2H), 2.04-1.88 (m, 2H). ESI MS (M+1)$^+$: 236, 238 (Cl).

E. 5-{4-[4-(4-Chloro-1H-pyrrolo[3,2-c]pyridin-2-yl)piperidine-1-carbonyl]phenyl}-1H-pyridin-2-one The title compound is prepared as described in EXAMPLE 31, Part K, but with 4-chloro-2-piperidin-4-yl-1H-pyrrolo[3,2-c]pyridine and 4-(6-oxo-1,6-dihydropyridin-3-yl)benzoic acid as starting materials. Purification was by flash column chromatography on silica gel. $^1$H NMR (d$_4$-MeOH) δ 7.99 (dd, 1H), 7.87 (d, 1H), 7.77 (d, 1H), 7.66-7.63 (m, 2H), 7.54-7.50 (m, 2H), 7.30 (dd, 1H), 6.65 (d, 1H), 6.41 (s, 1H), 3.96-3.84 (m, 1H), 3.45-3.05 (m, 4H), 2.22-2.01 (m, 2H), 1.92-1.71 (m, 2H). ESI MS (M+1)$^+$: 433, 435 (Cl).

F. 5-{4-[4-(4-Amino-1H-pyrrolo[3,2-c]pyridin-2-yl)piperidine-1-carbonyl]phenyl}-1H-pyridin-2-one trifluoroacetate The title compound is prepared as described in EXAMPLE 31, Part F, but with 5-{4-[4-(4-chloro-1H-pyrrolo[3,2-c]pyridin-2-yl)piperidine-1-carbonyl]phenyl}-1H-pyridin-2-one as the starting material. Heated (with stirring) at 110° C. for 4 days to obtain complete conversion. $^1$H NMR (d$_4$-MeOH) δ 7.98 (dd, 1H), 7.78 (d, 1H), 7.67-7.61 (m, 2H), 7.54-7.49 (m, 2H), 7.40 (d, 1H), 6.93 (d, 1H), 6.70-6.48 (m, 2H), 4.83-4.70 (m, 1H), 3.99-3.84 (m, 1H), 3.40-3.01 (m, 3H), 2.24-1.95 (m, 2H), 1.90-1.65 (m, 2H). ESI MS (M+1)$^+$: 414.

EXAMPLE 45

5-[4-(4-Amino-1H-pyrrolo[3,2-c]pyridin-2-yl)piperidine-1-carbonyl]-1'H-[2,3']bipyridin-6'-one trifluoroacetate The title compound is prepared as described in EXAMPLE 44, parts A and B, but with 6'-oxo-1',6'-dihydro-[2,3']bipyridinyl-5-carboxylic acid, and 5-[4-(4-chloro-1H-pyrrolo[3,2-c]pyridin-2-yl)piperidine-1-carbonyl]-1'H-[2,3']bipyridinyl-6'-one trifluoroacetate as starting materials, respectively. $^1$H NMR (d$_4$-MeOH) δ 8.67-8.65 (m, 1H), 8.32 (dd, 1H), 8.25 (d, 1H), 7.92 (dd, 1H), 7.85 (dd, 1H), 7.40 (d, 1H), 6.94 (d, 1H), 6.68-6.63 (m, 2H), 4.85-4.70 (m, 1H), 3.99-3.82 (m, 1H), 3.42-3.03 (m, 3H), 2.24-2.06 (m, 2H), 1.88-1.68 (m, 2H). ESI MS (M+1)$^+$: 415.

EXAMPLE 46

3-[1-(5-Phenylethynyl-pyridine-3-carbonyl)-piperidin-4-yl]-benzamidine hydrochloride A. 3-(Piperidin-4-yl)-benzonitrile A solution of lithium diisopropylamide (54 mmol) in anhydrous tetrahydrofuran (50 ml) at −78° C. is treated dropwise with a solution of benzyl 4-oxo-1-piperidinecarboxylate (11.4 g, 49 mmol) in anhydrous tetrahydrofuran (50 ml). The reaction mixture is then stirred a further 20 min. at −78° C. and treated with a solution of N-phenyltrifluoromethanesulfonimide (19.26 g, 54 mmol) in anhydrous tetrahydrofuran (55 ml). The resultant orange suspension is warmed to 0° C. and stirred for 2 hours before being concentrated under vacuum. The residue is chromatographed on silica gel (CH$_2$Cl$_2$) to yield benzyl 1,2,3,6-tetrahydro-4-(trifluoromethylsulphonyloxy)-pyridine-1-carboxylate as a yellow oil (11.34 g). A portion of this material (3.65 g, 10 mmol) is dissolved in anhydrous 1,2-dimethoxyethane (30 ml) and treated with 3-cyanophenyl boronic acid (1.47 g, 10 mmol), lithium chloride (1.27 g, 30 mmol), 2.0 M aqueous sodium carbonate (10 ml) and palladium tetrakistriphenylphosphine (0.73 g, 0.6 mmol). The reaction mixture is heated at reflux for 2.5 hours, cooled and concentrated under vacuum. The residue is partitioned between dichloromethane (2×100 ml) and 2.0M aqueous sodium carbonate (100 ml) containing conc ammonium hydroxide (6 ml). The combined organic extracts are dried (magnesium sulfate), concentrated under vacuum and the resultant oil is chromatographed on silica gel (ethyl acetate/pentane 2:5) to yield a yellow oil (2.31 g). This material is dissolved in ethanol (70 ml), treated with 10% palladium on carbon (1.0 g) and stirred at ambient temperature under an atmosphere of hydrogen for 5 hours. The reaction mixture is filtered through a short pad of hyflo and concentrated under vacuum to give the title compound as a colourless oil (1.26 g). $^1$H NMR (CDCl$_3$, 500 MHz) δ9.78 (br m, 1H), 7.50 (m, 4H), 4.49 (br m, 1H), 3.65 (br m, 1H), 3.00 (m, 2H), 2.82 (m, 1H), 2.21-1.75 (m, 4H). EI MS M$^+$+H: 187.

B. 3-[1-(5-Phenylethynyl-pyridine-3-carbonyl)-piperidin-4-yl]-benzonitrile

A solution of 5-phenylethynyl-pyridine-3-carboxylic acid (0.75 g, 3.3 mmol) in anhydrous dimethylformamide (9 ml) is treated with HATU (1.27 g, 3.3 mmol) and diisopropylethylamine (1.1 ml, 6.1 mmol). The reaction mixture is stirred 15 mins. at ambient temperature before being treated with a solution of 3-(piperidin-4-yl)-benzonitrile (0.6 g, 3 mmol) in dimethylformamide (6 ml). The reaction mixture is stirred at ambient temperature 2 hours, concentrated under vacuum and the residue partitioned between ethyl acetate (200 ml) and saturated aqueous sodium bicarbonate ((45 ml). The organic layer is dried (magnesium sulfate), concentrated under vacuum and the residue chromatographed on silica gel (dichloromethane/methanol 39:1) to give the title compound as a yellow oil (0.53 g). $^1$H NMR (CDCl$_3$, 500 MHz) δ8.80 (s, 1H), 8.63 (s, 1H), 8.00 (s, 1H), 7.50 (m, 9H), 4.90 (br m, 1H), 3.85 (br m, 1H), 3.28 (m, 1H), 2.90 (m, 2H), 1.91 (m, 1H), 1.75 (m, 3H). EI MS M$^+$+H: 392.

C. 3-[1-(5-Phenylethynyl-pyridine-3-carbonyl)-piperidin-4-yl]-benzamidine hydrochloride A solution of 3-[1-(5-phenylethynyl-pyridine-3-carbonyl)-piperidin-4-yl]-benzonitrile (0.51 g, 1.3 mmol) in methanol (20 ml) is cooled to 0° C. and saturated with hydrogen chloride gas. The reaction vessel is sealed and allowed to stand at 0° C. for 18 hours. The reaction mixture is concentrated to dryness under vacuum, redissolved in methanol (20 ml) and cooled to 0° C. The solution is saturated with ammonia gas and the vessel sealed before being allowed to stand at 0° C. for 48 hours. The reaction mixture is concentrated to dryness under vacuum and the residue chromatographed on silica gel (dichloromethane/methanol 9:1) to give the title compound as a light yellow amorphous solid (0.42 g). $^1$H NMR (DMSO, 500 MHz) δ8.85 (s, 1H), 8.67 (s, 1H), 8.08 (s, 1H), 7.75 (s, 1H), 7.67 (m, 2H), 7.62 (m, 2H), 7.56 (m, 1H), 7.48 (m, 2H), 7.47 (m, 1H), 4.67 (br m, 1H), 3.65 (br m, 1H), 2.94 (m, 3H), 1.96 (m, 1H), 1.68 (m, 3H). EI MS M$^+$+H: 409.

EXAMPLE 47

3-[1-(5-Phenylethynyl-pyridine-3-carbonyl)-1,2,3,6-tetrahydropyridin-4-yl]-benzamidine hydrochloride A solution of 5-phenylethynyl-pyridine-3-carboxylic acid (0.46 g, 2.1 mmol) in anhydrous dimethylformamide (7 ml) is treated with HATU (0.78 g, 2.1 mmol) and diisopropylethylamine (0.98 ml, 5.6 mmol). The reaction mixture is stirred 15 mins. at ambient temperature before being treated with a solution of 3-(1,2,3,6-tetrahydropyridin-4-yl)-benzonitrile (1.9 mmol) in dimethylformamide (6 ml). The reaction mixture is stirred at ambient temperature 3 hours, concentrated under vacuum and the residue partitioned between ethyl acetate (200 ml) and saturated aqueous sodium bicarbonate ((45 ml). The organic layer is dried (magnesium sulfate), concentrated under vacuum and the residue chromatographed on silica gel (dichloromethane/methanol 39:1) to give 3-[1-(5-phenylethynyl-pyridine-3-carbonyl)-1,2,3,6-tetrahydropyridin-4-yl]-benzonitrile as a yellow oil (0.23 g). This material is dissolved in methanol (15 ml), cooled to 0° C. and saturated with hydrogen chloride gas. The reaction vessel is sealed and allowed to stand at 0° C. for 18 hours. The reaction mixture is concentrated to dryness under vacuum, redissolved in methanol (15 ml) and cooled to 0° C. The solution is saturated with ammonia gas and the vessel sealed before being allowed to stand at 0° C. for 48 hours. The reaction mixture is concentrated to dryness under vacuum and the residue chromatographed on silica gel (dichloromethane/methanol 9:1) to give the title compound as a yellow amorphous solid (0.2 g). $^1$H NMR (DMSO, 500 MHz) δ8.85 (s, 1H), 8.67 (s, 1H), 8.10 (s, 1H), 7.85 (s, 1H), 7.80 (m, 1H), 7.75 (m, 1H), 7.60 (m, 3H), 7.48 (m, 3H), 6.38 (m, 1H), 4.38 (br m, 1H), 4.19 (br m, 1H), 3.90 (br m, 1H), 3.60 (br m, 1H), 2.63 (br m, 2H). EI MS M$^+$+H: 407.

EXAMPLE 48

3-[1-(5-Phenylethyl-pyridine-3-carbonyl)-piperidin-4-yl]-benzamidine hydrochloride A solution of 3-[1-(5-phenylethynyl-pyridine-3-carbonyl)-piperidin-4-yl]-benzamidine hydrochloride (Example 46) (150 mg) in ethanol (5 ml), treated with 10% palladium on carbon (15 mg) and stirred at ambient temperature under an atmosphere of hydrogen for 5 hours. The reaction mixture is filtered through a short pad of hyflo and concentrated under vacuum to give the title compound as a colourless oil (150 mg). $^1$H NMR (DMSO, 500 MHz) δ8.48 (m, 2H), 7.78 (s, 1H), 7.65 (m, 3H), 7.59 (m, 1H), 7.20 (m, 5H), 4.63 (br m, 1H), 3.57 (br m, 1H), 3.18 (br m, 1H), 2.90 (m, 6H), 1.70-1.90 (br m, 4H). EI MS M$^+$+H: 413.

EXAMPLE 49

3-[4-(5-Phenylethyl-pyridine-3-carbonyl)-piperazin-1-yl]-benzamidine di-hydrochloride A. 1-(3-Cyanophenyl)piperazine A mixture of 3-fluorobenzonitrile (3.0 g, 25 mmol), piperazine (11.8 g, 137 mmol) and dimethylsulphoxide (20 ml) is heated at 100° C. for 48 hours under an atmosphere of nitrogen. The reaction mixture is then cooled, poured into water (200 ml) and the resultant precipitate collected. This solid is chromatographed on silica gel (dichloromethane) to give the title compound as a white solid (6.7 g). $^1$H NMR (DMSO, 500 MHz) δ7.15-7.40 (m, 4H), 3.28 (m, 3H), 3.12 (m, 1H), 2.80 (m, 1H), 2.59 (m, 3H).

B. 3-[4-(5-Phenylethyl-pyridine-3-carbonyl)-piperazin-1-yl]-benzonitrile

A solution of 5-phenylethynyl-pyridine-3-carboxylic acid (0.4 g, 1.8 mmol) in anhydrous dimethylformamide (3 ml) is treated with HATU (0.7 g, 1.8 mmol) and diisopropylethylamine (0.6 ml, 3.3 mmol). The reaction mixture is stirred 10 mins. at ambient temperature before being treated with a solution of 1-(3-cyanophenyl)piperazine (0.3 g, 1.6 mmol) in dimethylformamide (5 ml). The reaction mixture is stirred at ambient temperature for 18 hours, concentrated under vacuum and the residue partitioned between dichloromethane (2×40 ml) and saturated aqueous sodium bicarbonate (40 ml). The organic layer is dried (magnesium sulfate), concentrated under vacuum and the residue chromatographed on silica gel (ethyl acetate) to give the title compound as a yellow oil (0.33 g). $^1$H NMR (CDCl$_3$, 500 MHz) δ8.82 (s, 1H), 8.61 (s, 1H), 7.90 (s, 1H), 7.58 (m, 2H), 7.39 (m, 4H), 7.16 (m, 3H), 3.95 (br m, 2H), 3.63 (br m, 2H), 3.30 (br m, 4H), EI MS M$^+$+H: 393.

C. 3-[4-(5-Phenylethyl-pyridine-3-carbonyl)-piperazin-1-yl]-benzamidine hydrochloride A solution of 3-[1-(5-phenylethynyl-pyridine-3-carbonyl)-piperidin-4-yl]-benzonitrile (0.32 g, 0.8 mmol) in methanol (20 ml) is cooled to 0° C. and saturated with hydrogen chloride gas. The reaction vessel is sealed and allowed to stand at 0° C. for 18 hours. The reaction mixture is concentrated to dryness under vacuum, redissolved in methanol (20 ml) and cooled to 0° C. The solution is saturated with ammonia gas and the vessel sealed before being allowed to stand at 0° C. for 48 hours. The reaction mixture was concentrated to dryness under vacuum and the residue chromatographed on silica gel (dichloromethane/methanol 4:1) to give the title compound as a yellow amorphous solid (45 mg). $^1$H NMR (DMSO, 500 MHz) δ9.25 (br s, 1H), 8,92 (br s 1H), 8.85 (s, 1H), 8.65 (s, 1H), 8.10 (s, 1H), 7.60 (m, 2H), 7.45 (m, 4H), 7.32 (m, 2H), 7.20 (m, 1H), 3.80 (br m, 2H), 3.52 (br m, 2H), 3.30-3.40 (br m, 4H). EI MS M$^+$+H: 410.

By methods described above, the following compounds are made:

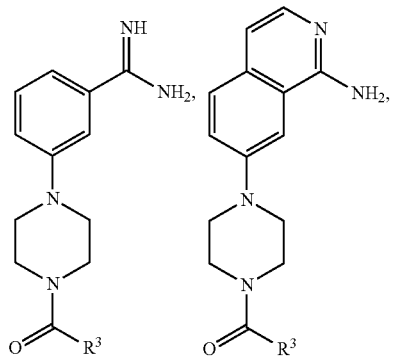

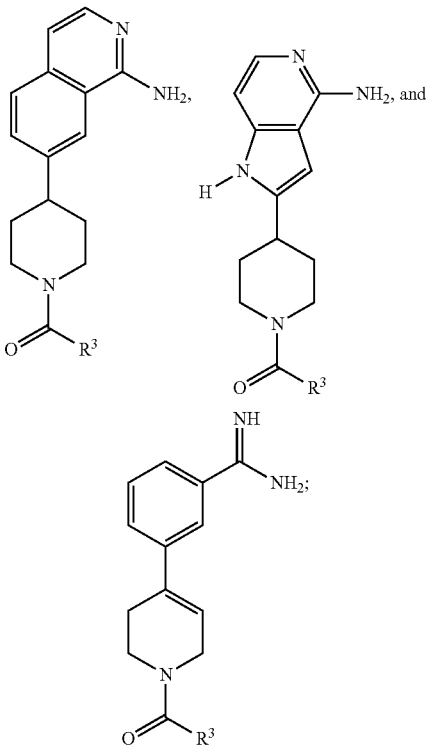

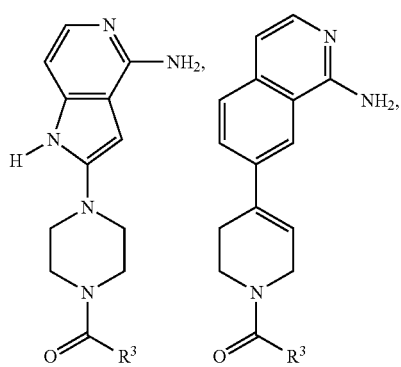

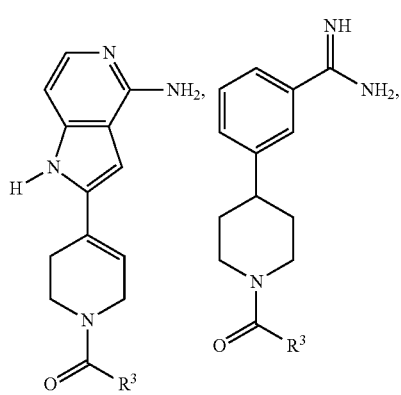

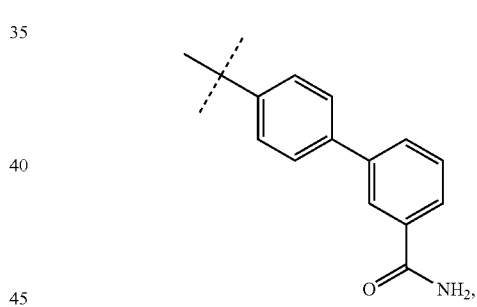

wherein R$^3$ is selected from the group consisting of

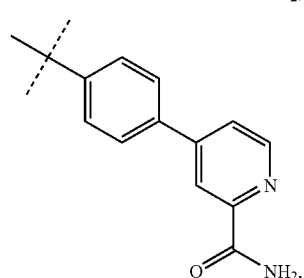

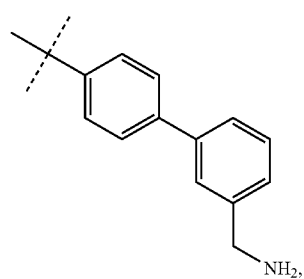

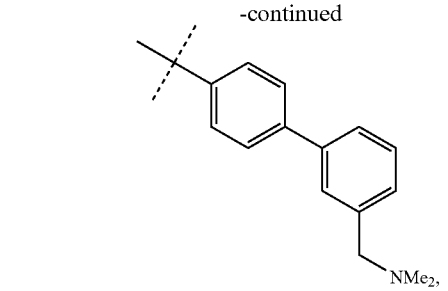
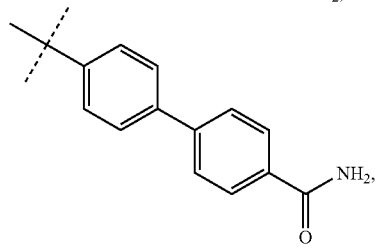
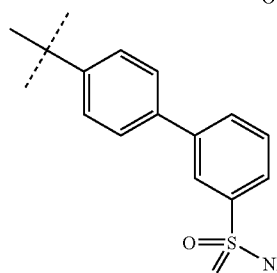
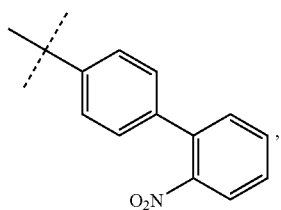
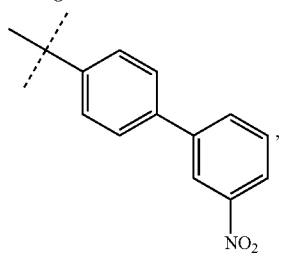
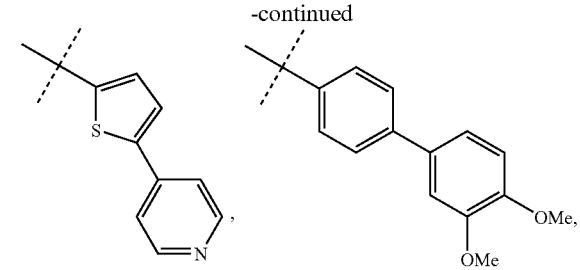
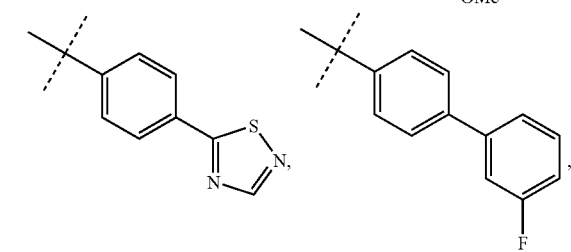
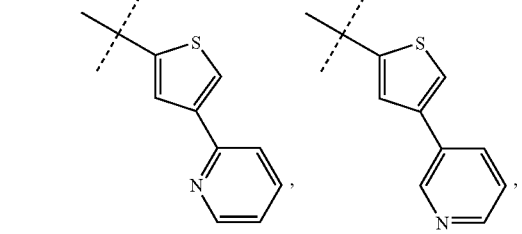
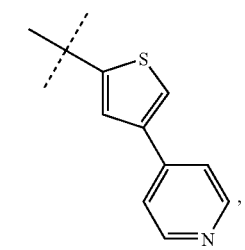
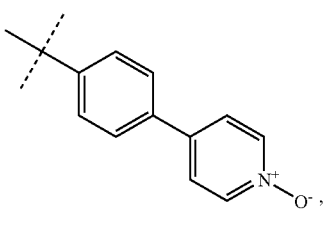

53
-continued
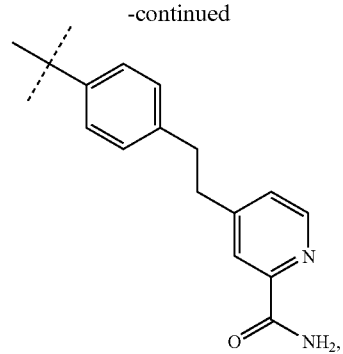
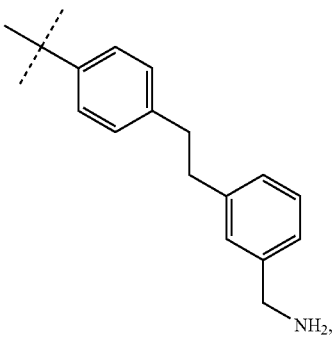
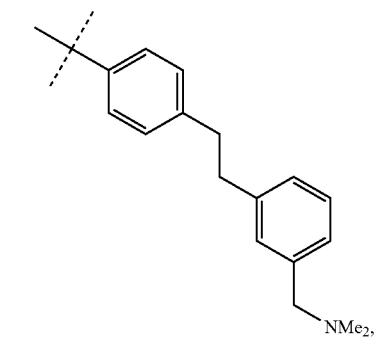
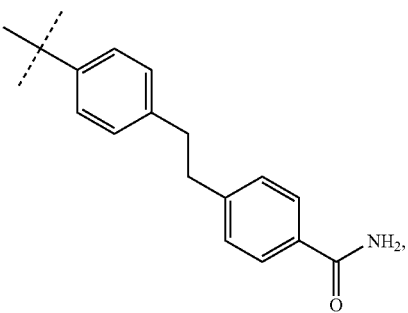
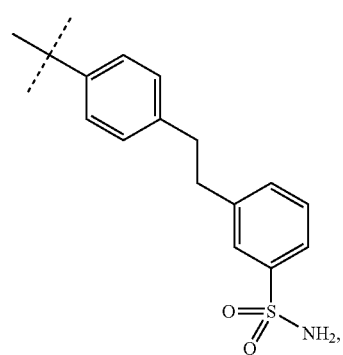
54
-continued
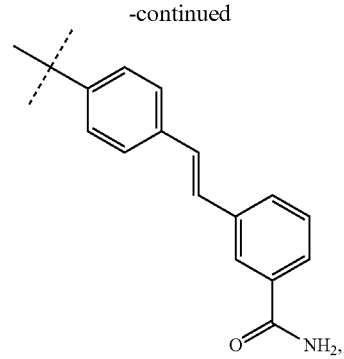
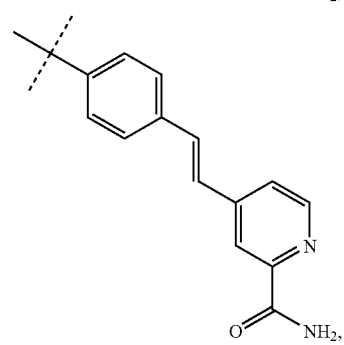
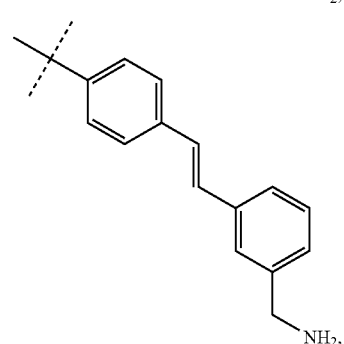
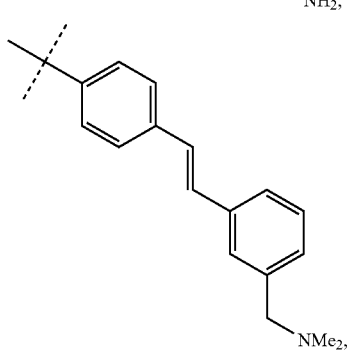
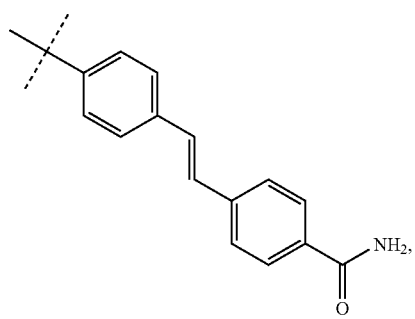

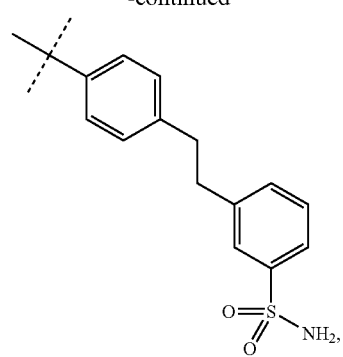
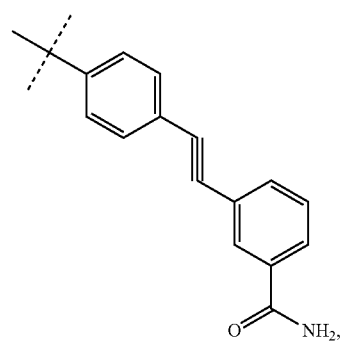
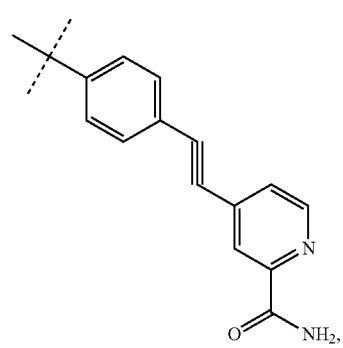
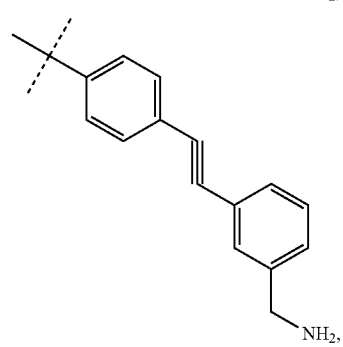
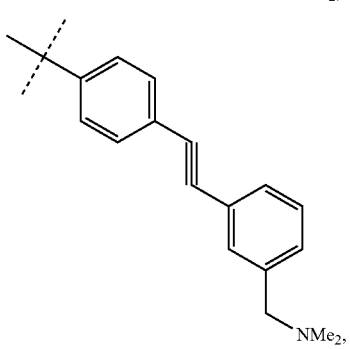
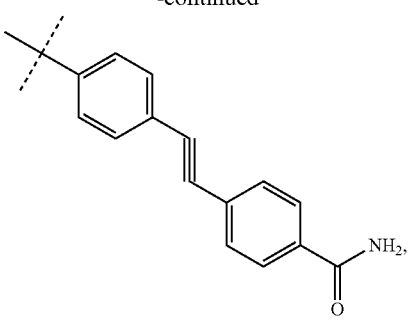
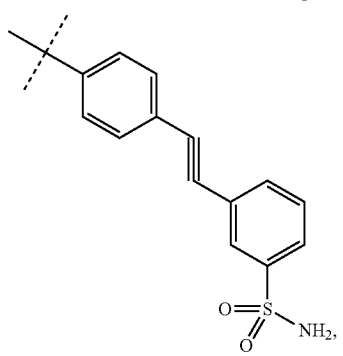
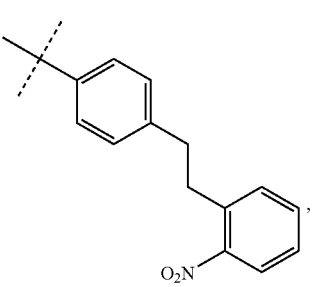
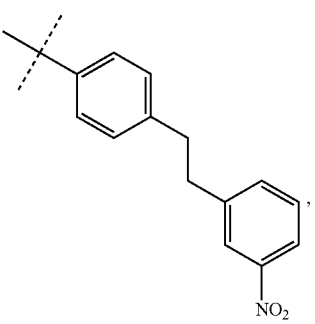
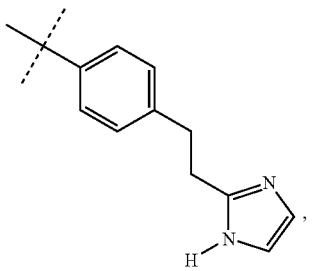

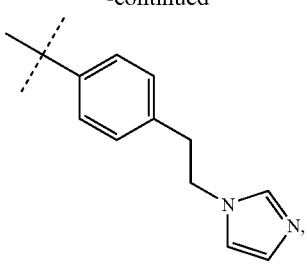
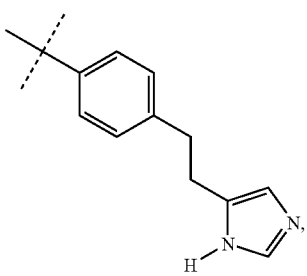
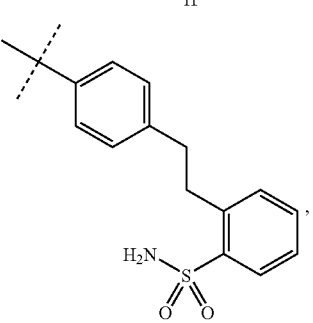
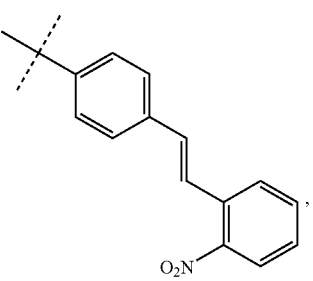
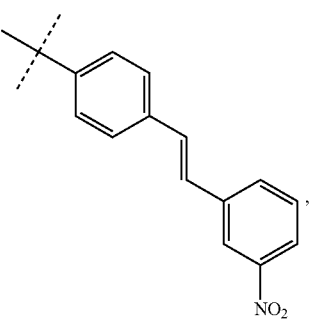
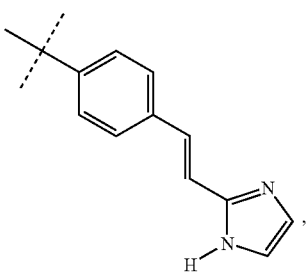
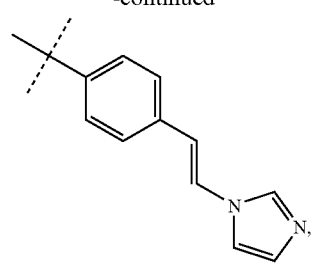
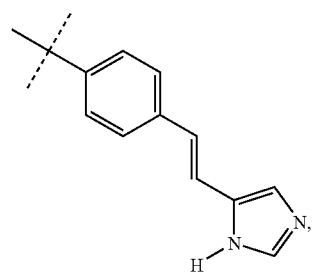
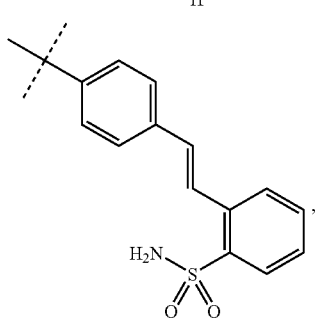
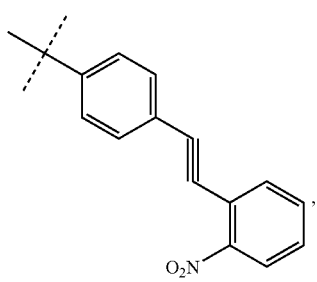
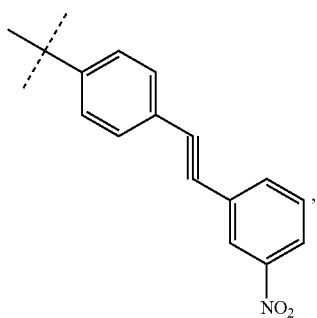
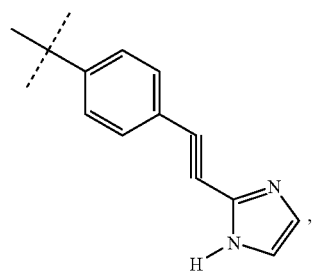

-continued
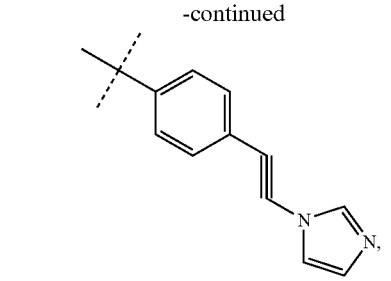
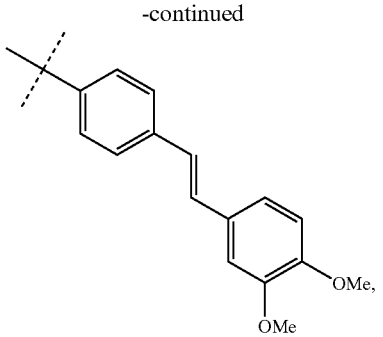
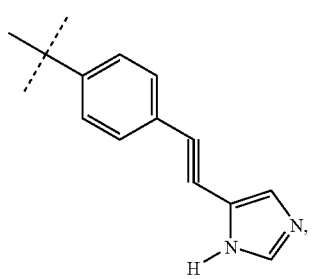
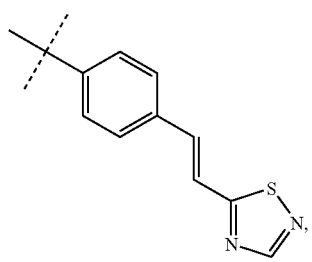
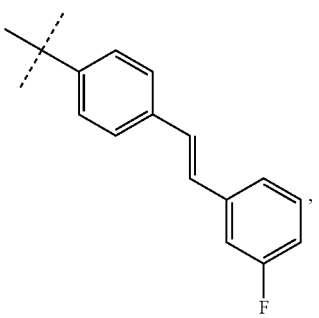
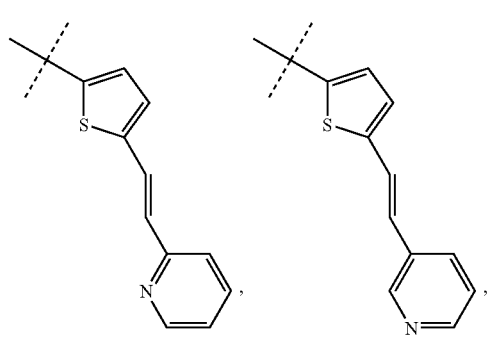
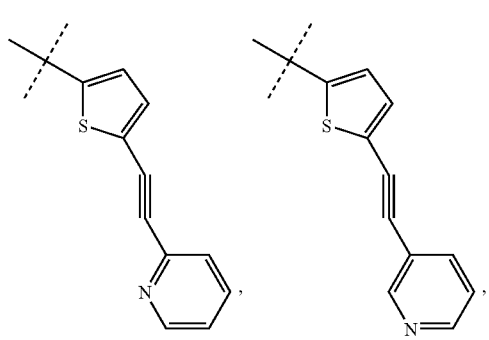
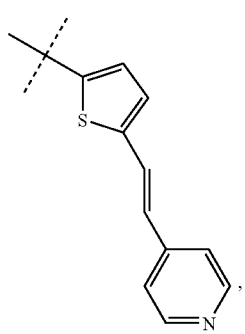

61
-continued
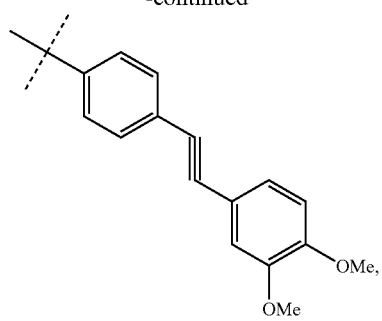
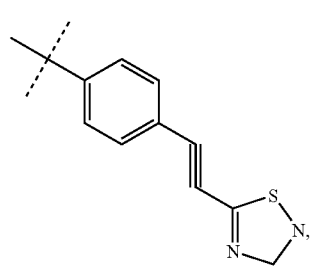
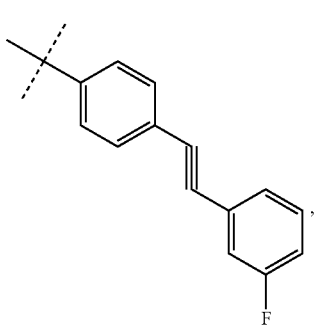
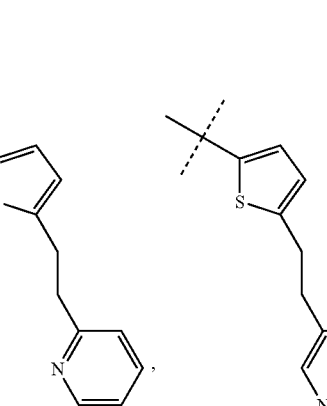
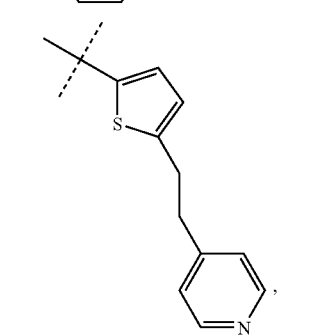
62
-continued
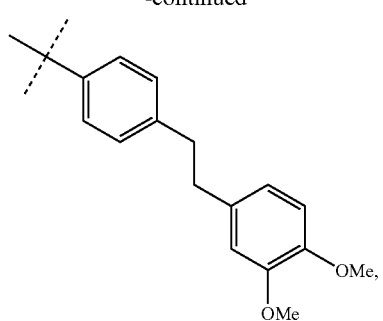
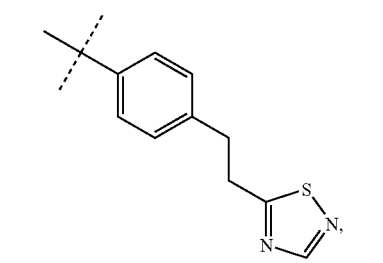
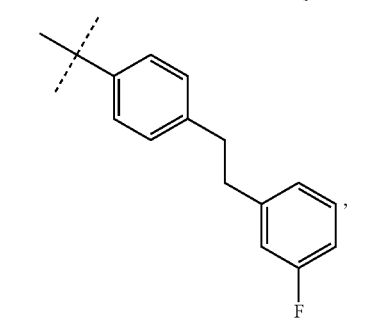
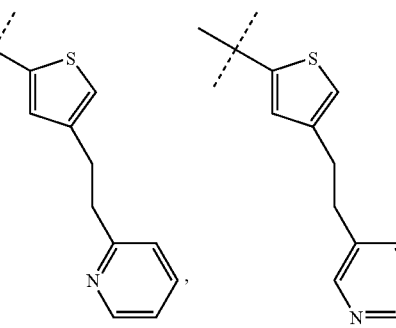

63
-continued
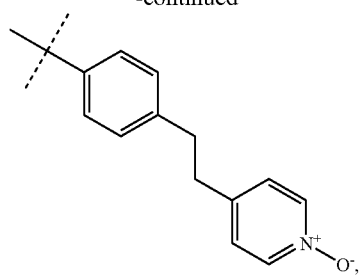
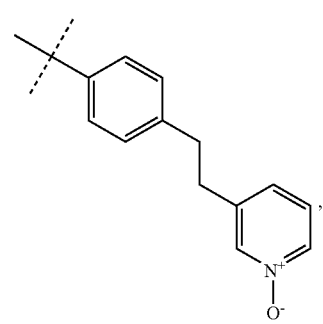
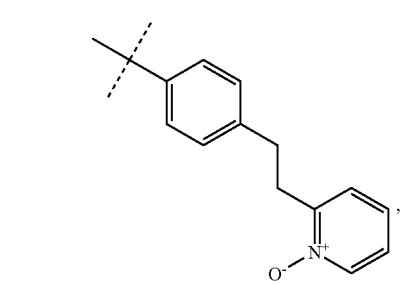
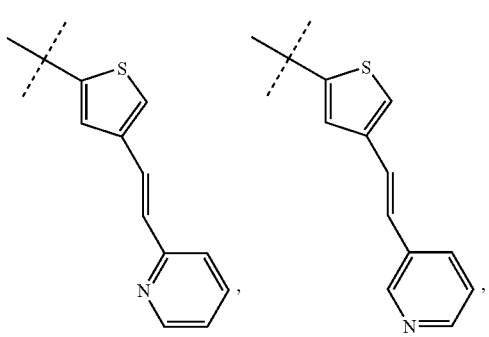
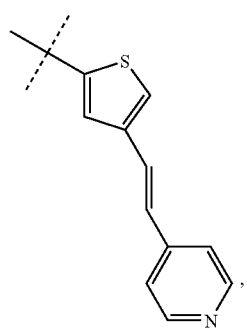
64
-continued
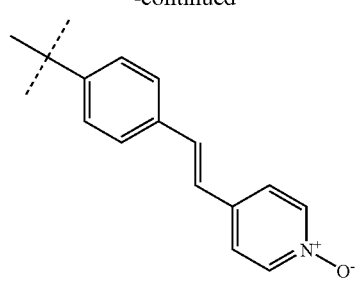
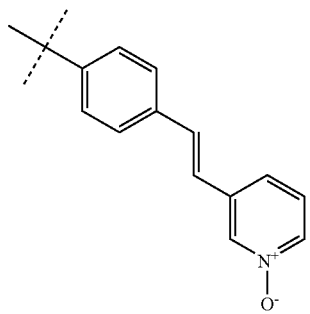
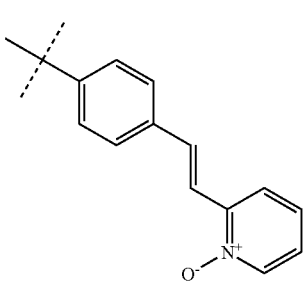
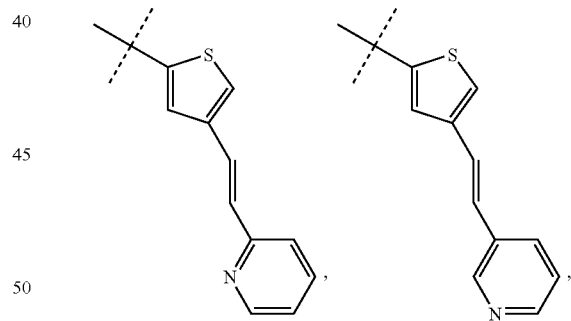
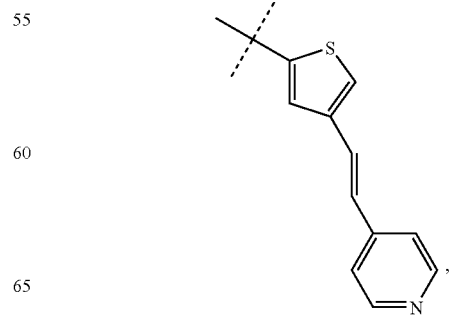

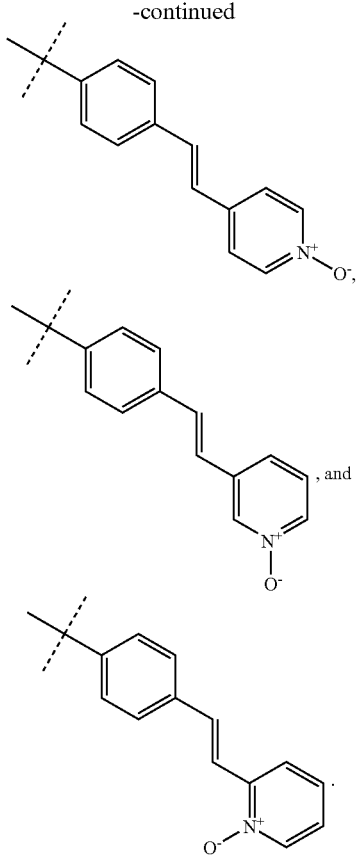

The molecules described herein inhibit blood coagulation by virtue of their ability to inhibit the penultimate enzyme in the coagulation cascade, factor Xa, rather than thrombin. Both free factor Xa and factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective factor Xa inhibition is achieved by administering the compounds either by oral administration, continuous intravenous infusion, bolus intravenous administration or any other parenteral route such that it achieves the desired effect of preventing the factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

The compounds described herein may be administered to treat thrombotic complications in a variety of animals such as primates including humans, sheep, horses, cattle, pigs, dogs, rats and mice. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any factor Xa inhibitor can be added to or contacted with any medium containing or suspected of containing factor Xa and in which it is desired that blood coagulation be inhibited.

In addition to their use in anticoagulant therapy, factor Xa inhibitors may find utility in the treatment or prevention of other diseases in which the generation of thrombin has been implicated as playing a pathologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor. Inhibition of factor Xa will effectively block thrombin generation and therefore neutralize any pathologic effects of thrombin on various cell types.

Accordingly, the invention provides a method of inhibiting factor Xa comprising contacting a factor Xa inhibitory amount of a compound of formula I with a composition containing Factor Xa.

According to a further feature of the invention there is provided a method of inhibiting the formation of thrombin comprising contacting Factor Xa inhibitory amount of a compound of formula I with a composition containing Factor Xa.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of an effective amount of compound of formula I or a composition containing a compound of formula I.

The compounds of formula I may be used alone or in combination with other diagnostic, cardioprotective agents, direct thrombin inhibitors, anticoagulants, antiplatelet or fibrinolytic agents, selected from: anti-coagulants such as warfarin, heparin or low molecular weight heparin; synthetic pentasaccharides; anti-platelet agents such as aspirin, piroxicam or ticlopidine; direct thrombin inhibitors (e.g. boroarginine derivatives, hirudin or argatroban (Novastan®); fibrinogen receptor antagonists; statins/fibrates; or fibrinolytic agents (thrombolytic agents) such as tissue plasminogen activator, anistreplase (Eminase®), urokinase or streptokinase, Factor Xa inhibitors or Factor VIIa inhibitors; or combinations thereof. Often patients are concurrently treated prior, during and after interventional procedures with agents of these classes either in order to safely perform the interventional procedure or to prevent deleterious effects of thrombus formation.

The term "cardioprotective agents" as used herein, denotes agents that act to protect myocardium during ischemia. These cardioprotective agents include, but are nor limited to, adenosine agonists, β-blockers and Na/H exchange inhibitors. Adendosine agonists include those compounds disclosed in Spada et al., U.S. Pat. No. 5,364,862 and Spada et al., U.S. Pat. No. 5,736,554, the disclosures of which are hereby incorporated herein by reference. An example of an adenosine agonists is AMP 579 (Rhone-Poulenc Rorer). An example of a Na/H exchange inhibitor is Cariporide (HOE 642).

The term "anti-coagulant agents" as used herein, denotes agents that inhibit blood coagulation. Such agents include warfarin (Coumadin®) and heparin.

The term "anti-platelet agents" as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam (Feldane®), including pharmaceutically acceptable salts or prodrugs thereof. Other suitable anti-platelet agents include ticlopidine (Ticlid), thromboxane-A2-receptor antagonists and thromboxane-A2-synthetase inhibitors, as well as pharmaceutically acceptable salts or prodrugs thereof.

The term "direct thrombin inhibitors" (i.e. Factor IIa inhibitors), as used herein, denotes inhibitors of the serine protease thrombin. By inhibiting thrombin directly, the inhibition of the cleavage of fibrinogen to fibrin, activation of Factor XIIIa, activation of platelets, and feedback of thrombin to the coagulation cascade to generate more thrombin, occurs. Such direct inhibitors include boroarginine derivatives and boropeptides, hirudin and argatroban (Novastan®), including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "fibrinolytic agents" (or thrombolytics or fibrinolytics), as used herein, denotes agents that lyse blood clots. Such agents include tissue plasminogen activator, anistreplase (Eminase®), urokinase or streptokinase, including pharmaceutically acceptable salts or prodrugs thereof. Tissue plasminogen activator (tPA) is commercially available from Genentech Inc., South San Francisco, Calif. The term urokinase, as used herein, is intended to denote both dual and single chain urokinase, the latter also being referred to herein as prourokinase.

The compounds of the present invention may be used in combination with any antihypertensive agent or cholesterol or lipid regulating agent, or concurrently in the treatment of restenosis, atherosclerosis or high blood pressure. Some examples of agents that are useful in combination with a compound according to the invention in the treatment of high blood pressure include compounds of the following classes; beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCoA reductase inhibitors, compounds of the fibrate class.

Other pharmaceutically active agents can be employed in combination with the compounds of the invention depending upon the disease being treated. For example, β-adrenergic agonist compound such as albuterol, terbutaline, formoterol, fenoterol, or prenaline; an anti-inflammatory corticosteroid compound such as beclomethasone, triamcinolone, flurisolide, or dexamethasone; an anticholinergics compound such as ipratropium bromide; and an anti-inflammatory compound such as sodium cromoglycate or nedocromil sodium.

It is understood that the present invention includes combinations of compounds of the present invention with one or more of the aforementioned therapeutic class agents.

It is a further object of the invention to provide kits having a plurality of active ingredients (with or without carrier) which, together, may be effectively utilized for carrying out the novel combination therapies of the invention.

It is another object of the invention to provide novel pharmaceutical compositions which is effective, in and of itself, for utilization in a beneficial combination therapy because it includes a plurality of active ingredients which may be utilized in accordance with the invention.

In another aspect, the present invention provides a method for treating a disease associated with factor Xa or tryptase activity in a patient in need of such treatment, said method including the steps of administering a therapeutically effective amount of the compound of formula I and administering a therapeutically effective amount of one of the aforementioned therapeutic class agents.

The invention also provides kits or single packages combining two or more active ingredients useful in treating a disease associated with factor Xa or tryptase activity. A kit may provide (alone or in combination with a pharmaceutically acceptable diluent or carrier), the compound of formula I and one of the aforementioned therapeutic class agents (alone or in combination with diluent or carrier).

The present invention also includes within its scope pharmaceutical formulations which comprise at least one of the compounds of Formula I in association with a pharmaceutically acceptable carrier or coating.

In practice, compounds of the present invention may generally be administered parenterally, intravenously, subcutaneously intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The compounds of the present invention may also be formulated for use in conjunction with other therapeutic agents such as agents or in connection with the application of therapeutic techniques to address pharmacological conditions which may be ameliorated through the application of a compound of formula I, as described herein.

Compounds within the scope of the present invention exhibit marked pharmacological activities according to tests described in the literature and below which tests results are believed to correlate to pharmacological activity in humans and other mammals.

Enzyme Assays:

The ability of the compounds in the present invention to act as inhibitors of factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50=Ki[1+[S]/Km]) assuming competitive inhibition kinetics. Ki values for particular examples of compounds of the present invention with respect to Factor Xa, as well as Ki values for particular examples of compounds of the present invention with respect to tryptase, are set forth in the table below:

| EXAMPLE # | NAME | Factor Xa Ki (nM) |
| --- | --- | --- |
| 8 | 3-[1-(4-Pyridin-3-yl-benzoyl)-1,2,3,6-tetrahydropyridin-4-yl]benzamidine ditrifluoroacetate. | 5.0 |
| 10 | 3-{1-[4-(5-Bromofuran-2-yl)-benzoyl]-1,2,3,6-tetrahydropyridin-4-yl}benzamidine trifluoroacetate. | 34 |
| 11 | 3-{1-[4-(5-Chlorothiophen-2-yl)-benzoyl]-1,2,3,6-tetrahydropyridin-4-yl}benzamidine trifluoroacetate. | 688 |
| 16 | 3[1-(4-Pyrimidin-2-ylbenzoyl)-1,2,3,6-tetrahydropyridin-4-yl]-benzamidine ditrifluoroacetate. | 63 |
| 25 | 3-[1-(4-Pyridin-2-ylbenzoyl)-piperidin-4-yl]benzamidine ditrifluoroacetate | 9.0 |

-continued

| | | Tryptase Ki (nM) |
|---|---|---|
| 35 | 4'-[4-(1-Aminoisoquinolin-7-yl)piperidine-1-carbonyl]biphenyl-3-carboxylic acid amide trifluoroacetate | 570 |
| 39 | 5-{4-[4-(1-Aminoisoquinolin-7-yl)-3,6-dihydro-2H-pyridine-1-carbonyl]phenyl}-1H-pyridin-2-one trifluoroacetate | 140 |
| 44 | 5-{4-[4-(4-Amino-1H-pyrrolo[3,2-c]pyridin-2-yl)piperidine-1-carbonyl]phenyl}-1H-pyridin-2-one trifluoroacetate | 990 |
| EXAMPLE # | NAME | Tryptase Ki (nM) |
| 47 | 3-[1-(5-Phenylethynyl-pyridine-3-carbonyl)-1,2,3,6-tetrahydropyridin-4-yl]-benzamidine hydrochloride | 183 |
| 49 | 3-[4-(5-Phenylethyl-pyridine-3-carbonyl)-piperazin-1-yl]-benzamidine di-hydrochloride | 1,070 |

An additional in vitro assay may be used to evaluate the potency of compounds according to the invention in normal human plasma. The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay:

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model:

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Holst, B. Lindblad, D. Bergqvist, O. Nordfang, P. B. Ostergaard, J. G. L. Petersen, G. Nielsen and U. Hedner. *Thrombosis and Haemostasis*, 71, 214-219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5-2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2-3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18 G needle just below the distal most clamp. This creates a region of reduced flow and partial stasis at the injury site. The isolated segment is gently rinsed with saline 2-3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2-3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 mL ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model:

The antithrombotic efficacy of factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. *Journal of Cardiovascular Pharmacology*, 22, 526-533 (1993); Rat Model of Arterial Thrombosis Induced by Ferric Chloride, K.

D. Kurtz, B. W. Main, and G. E. Sandusky. *Thrombosis Research*, 60, 269-280 (1990); The Effect of Thrombin Inhibition in a Rat Arterial Thrombosis Model, R. J. Broersma, L. W. Kutcher and E. F. Heminger. *Thrombosis Research* 64, 405-412 (1991). This model is widely used to evaluate the antithrombotic potential of a variety of agents including heparin and the direct acting thrombin inhibitors.

Sprague Dawley rats weighing 375-450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95-1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after intragastric dosing, the animal is anesthetized and instrumented as described previously. Experiments are then performed according to the protocol described above. By way of example, Compound 184 shows $K_i$ values of 27.0 nM, 1.72 µM, and 2.71 µM, in the Factor Xa, trypsin, and thrombin assays, respectively. Compound 45 shows $K_i$ values of 94.0 nM, 129 nM, and 477 nM, in the Factor Xa, trypsin, and thrombin assays, respectively. Compound 167 shows $K_i$ values of 19.0 nM, 46 nM, and 1.228 µM, in the Factor Xa, trypsin, and thrombin assays, respectively.

Tryptase Inhibition Activity:

Tryptase inhibition activity is confirmed using either isolated human lung tryptase or recombinant human β tryptase expressed in yeast cells. Essentially equivalent results are obtained using isolated native enzyme or the expressed enzyme. The assay procedure employs a 96 well microplate (Costar 3590) using L-pyroglutamyl-L-prolyl-L-arginine-para-nitroanilide (S2366: Quadratech) as substrate (essentially as described by McEuen et. al. Biochem Pharm, 52, pp 331-340, 1996). Assays are performed at room temperature using 0.5 mM substrate ($2 \times K_m$) and the microplate is read on a microplate reader (Beckman Biomek Plate reader) at 405 nm wavelength. To determine the compound concentration that inhibites half of the enzyme activity ($IC_{50}$), the fraction of control activity (FCA) is plotted as a function of the inhibitor concentration (I).

The present invention may be embodied in other specific forms without departing from the spirit or essential attributes thereof.

What is claimed is:

1. A compound of compound of formula I:

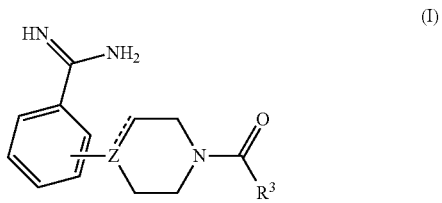

(I)

wherein,

Z is CH or N;

══════ is a single or double bond, provided that when Z is nitrogen atom, then ══════is a single bond;

$R^3$ is phenyl that is optionally substituted with one or two ring system substituents which may be the same or different, or pyridyl or thienyl that is optionally substituted by one or two ring system substituents which may be the same or different, and wherein, the pyridyl nitrogen atom is optionally oxidized to the corresponding N-oxide; and ring system substituents are selected from the group consisting of,

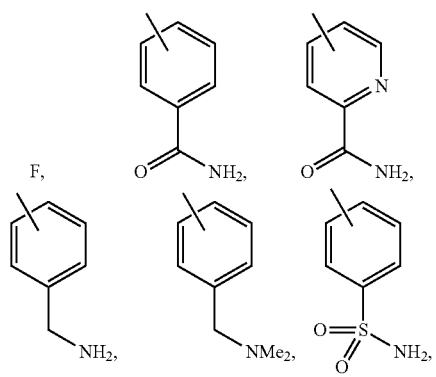

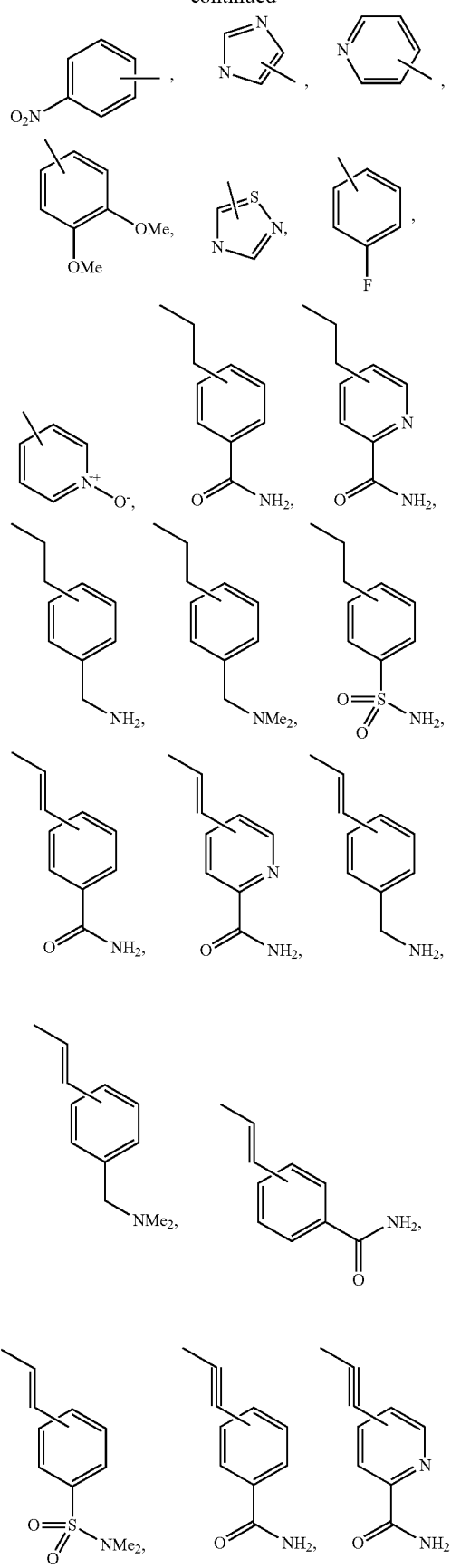
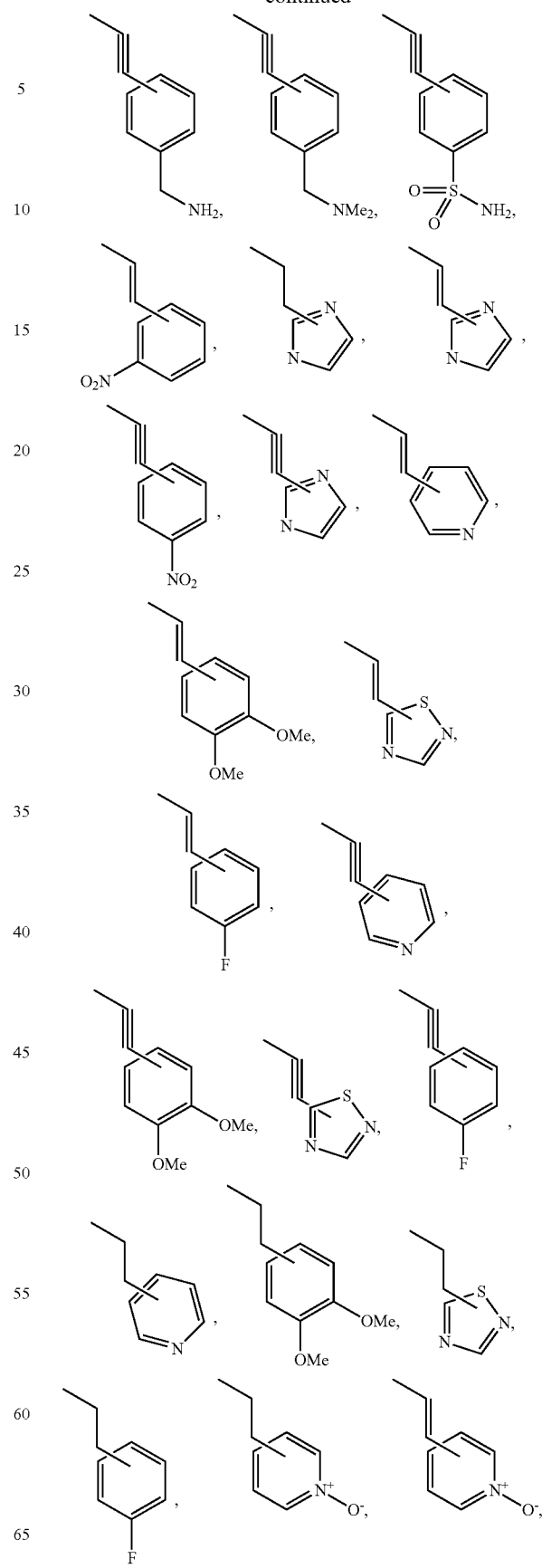

-continued

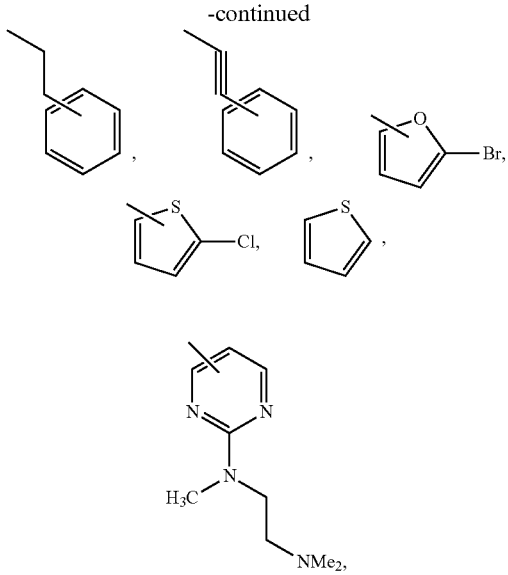

a pharmaceutically acceptable salt thereof, or an N-oxide thereof.

2. The compound according to claim 1 wherein Z is CH.
3. The compound according to claim 1 wherein Z is N.
4. The compound according to claim 2 wherein Z is CH.
5. The compound according to claim 4 wherein ==== is a double bond.
6. The compound according to claim 4 wherein ==== is a single bond.
7. The compound according to claim 3 wherein Z is N.

8. The compound according to claim 1, which is selected from the group consisting of:

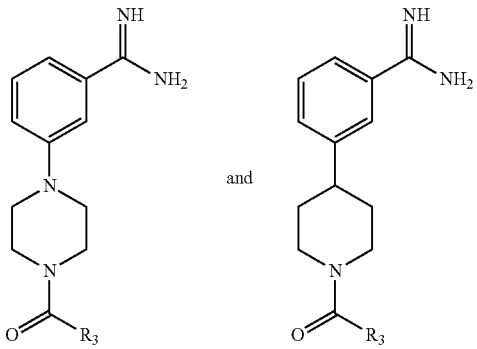

and wherein $R^3$ is selected from the group consisting of,

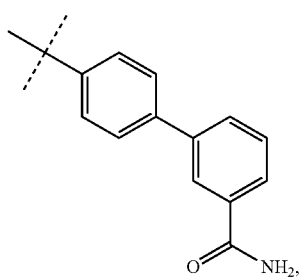

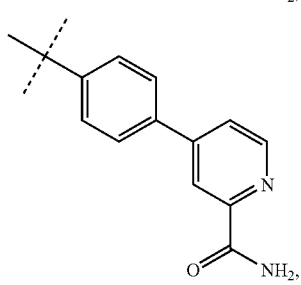

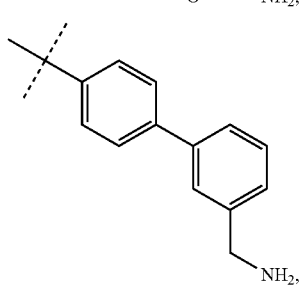

79
-continued
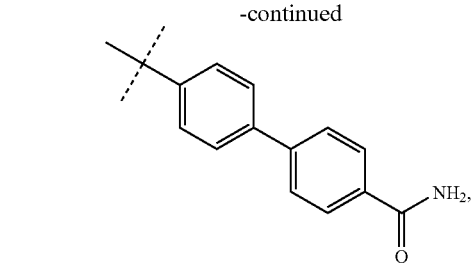
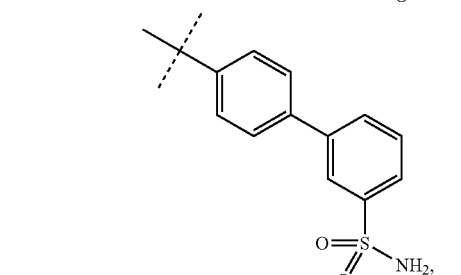
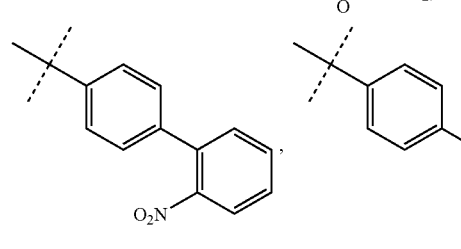
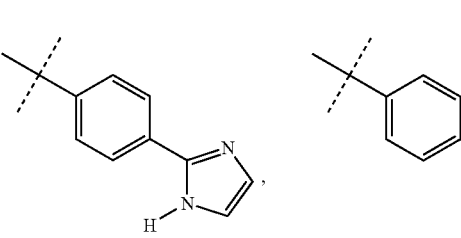
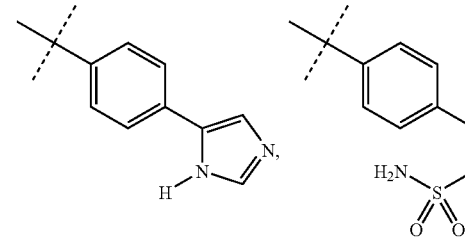
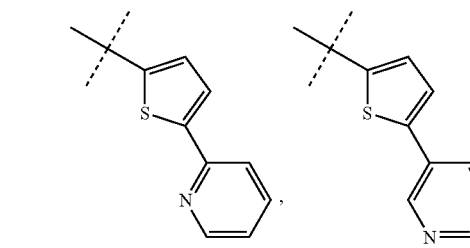
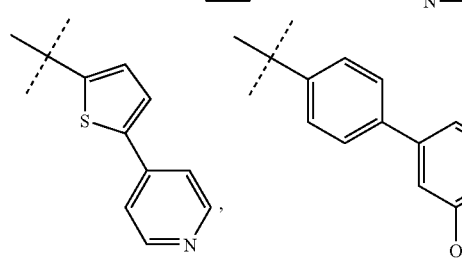
80
-continued
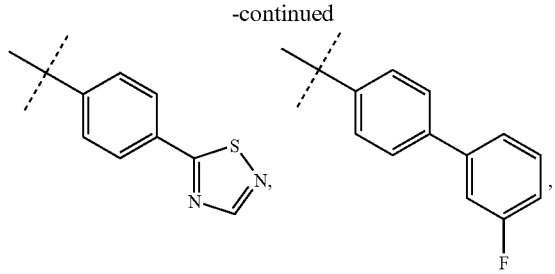
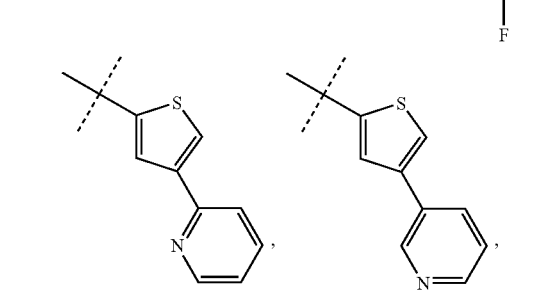
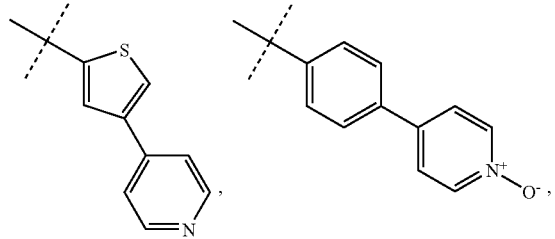
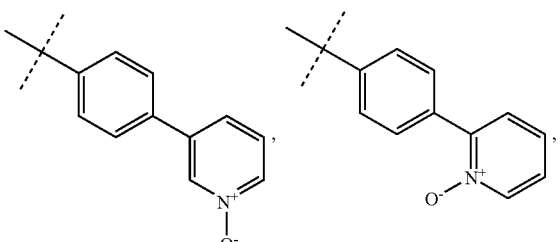
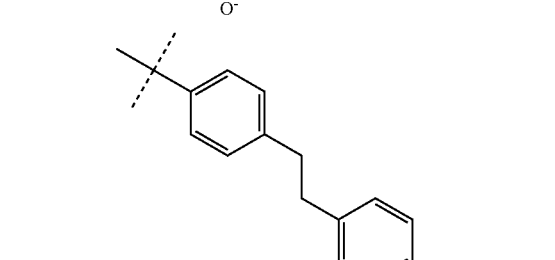
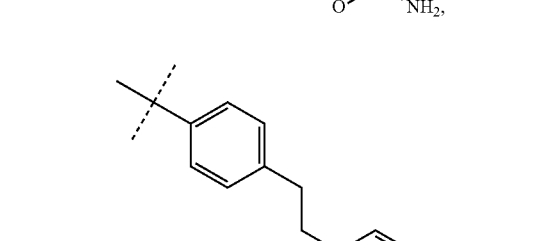
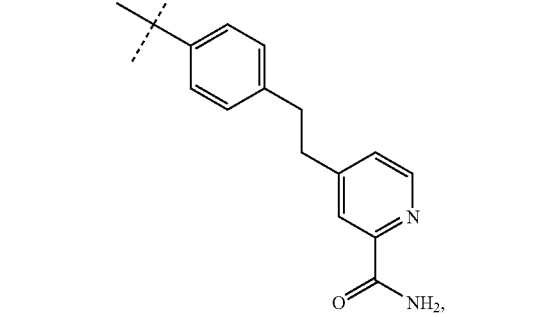

81
-continued
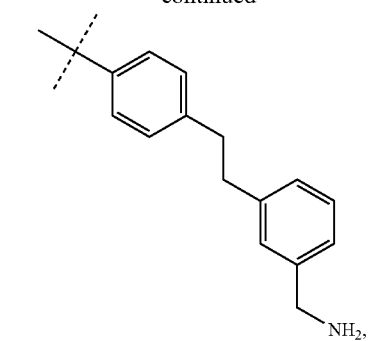
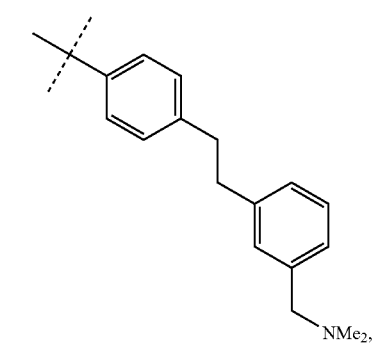
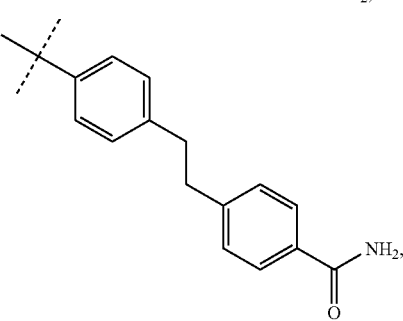
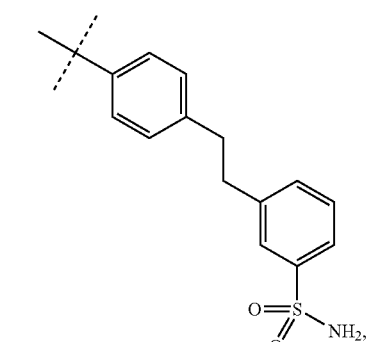
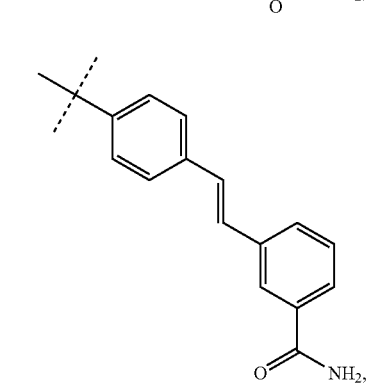
82
-continued
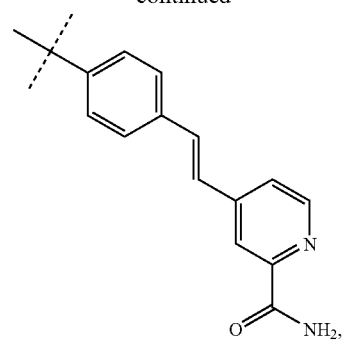
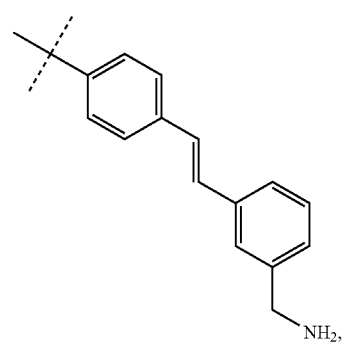
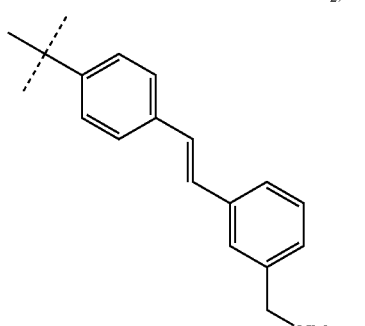
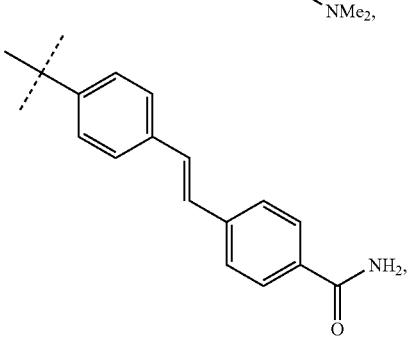
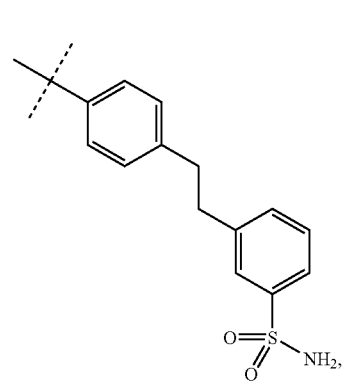

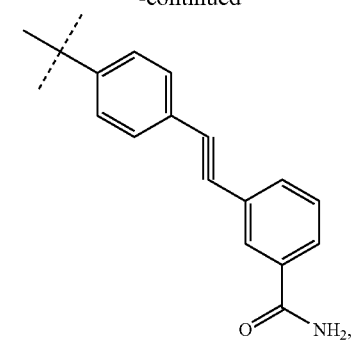
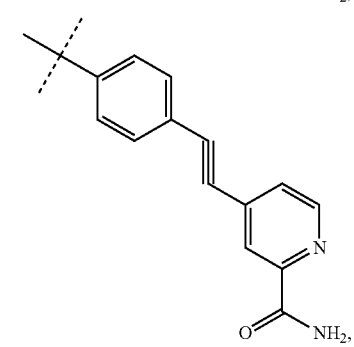
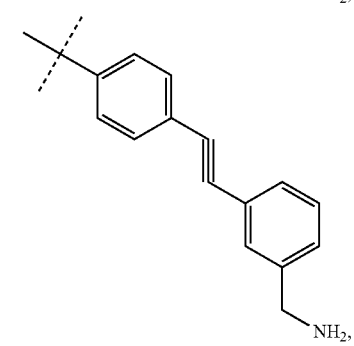
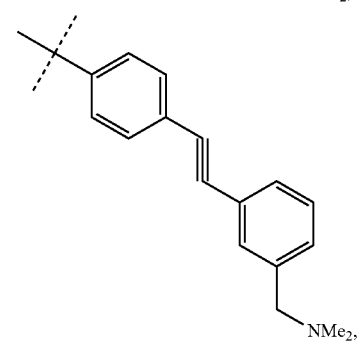
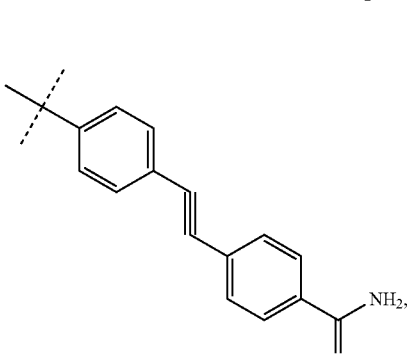
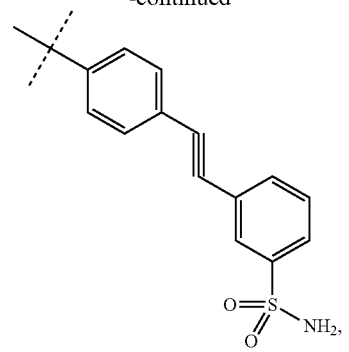
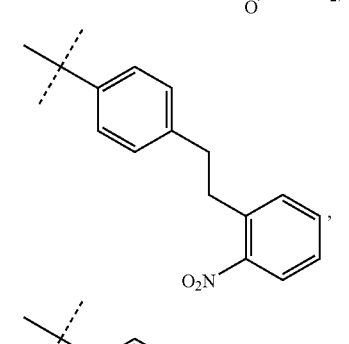
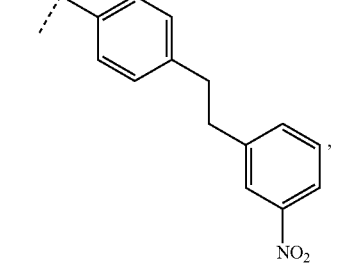
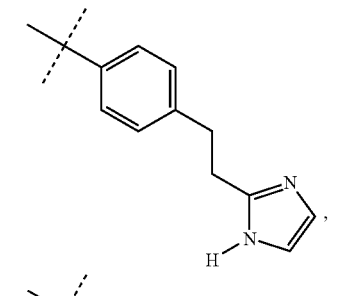
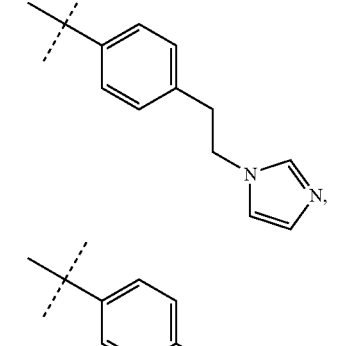
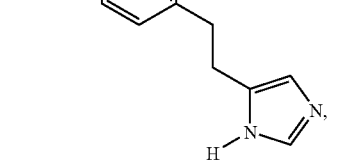

85
-continued
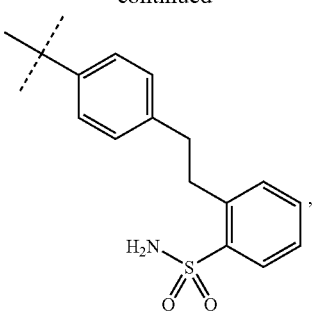
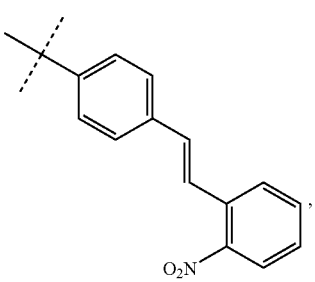
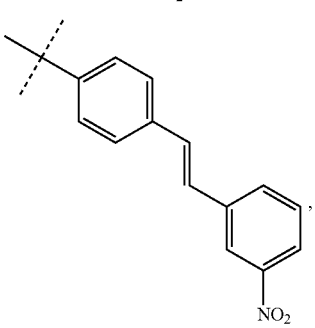
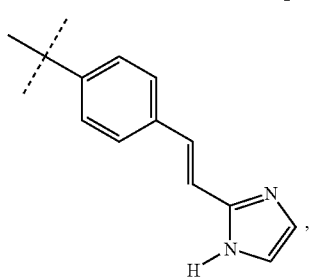
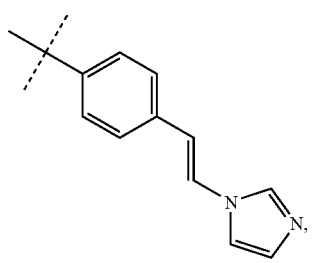
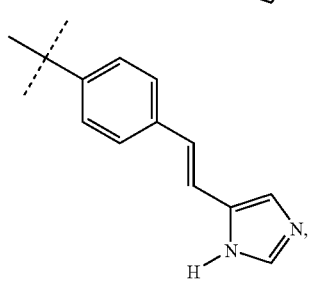
86
-continued
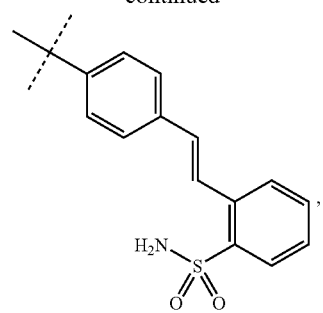
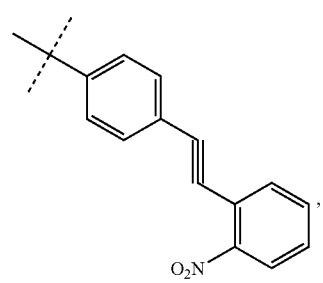
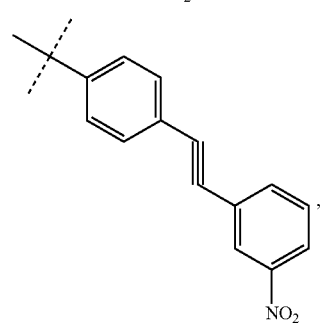
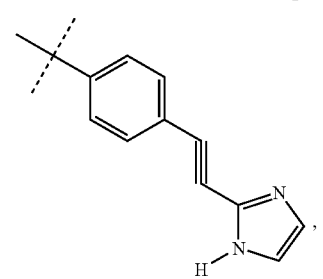
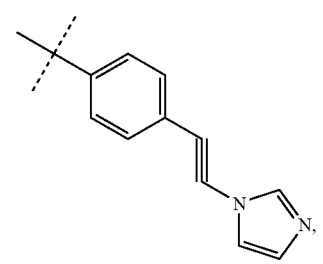
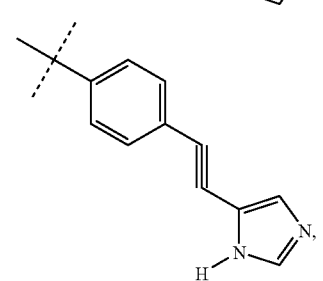

87
-continued
88
-continued
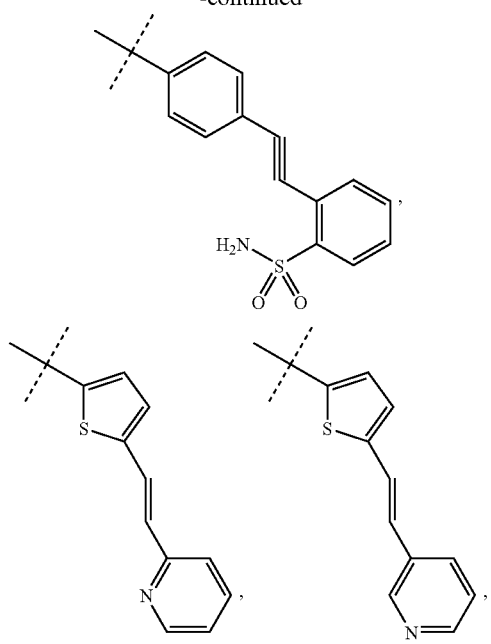
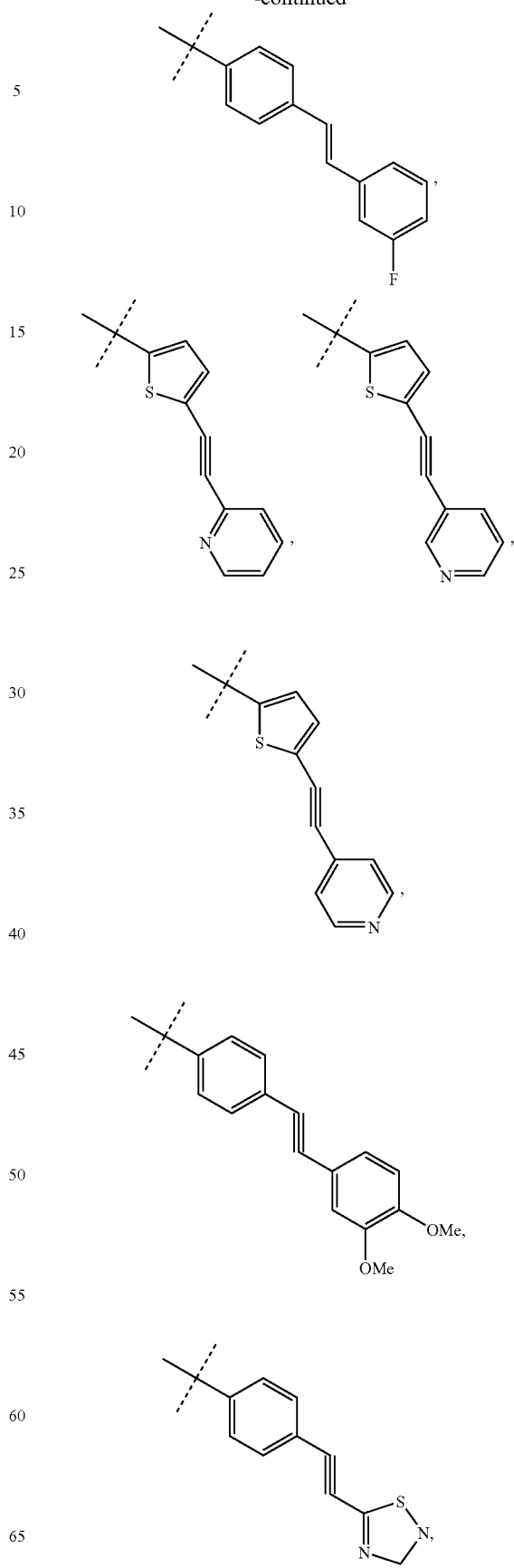

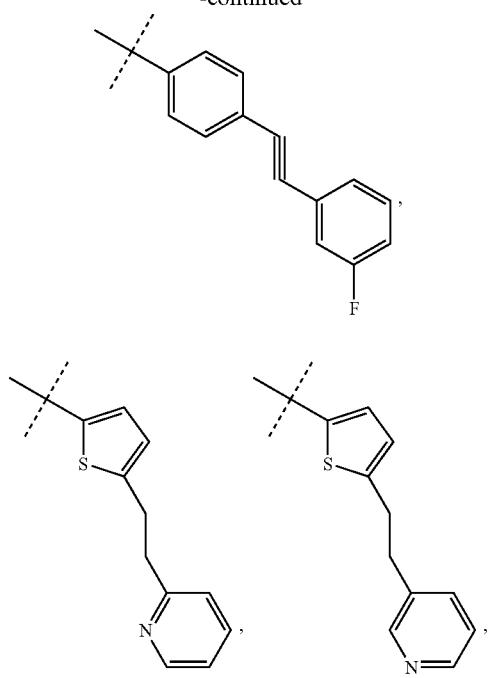
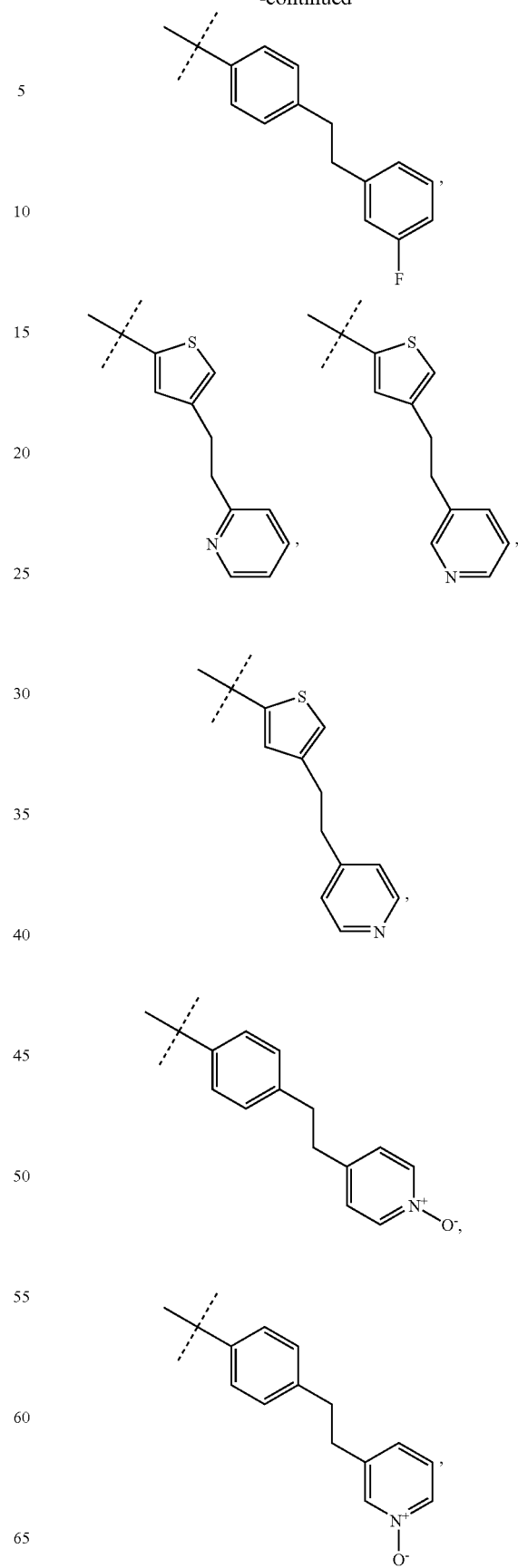

91
-continued
92
-continued
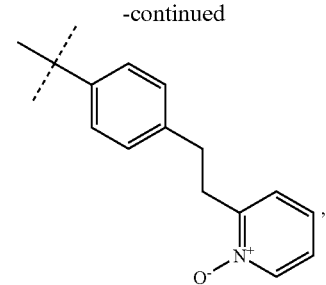
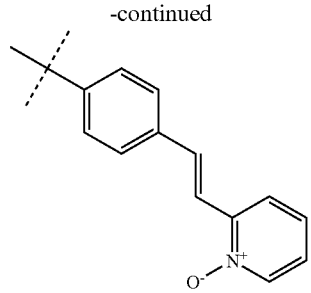

93
-continued
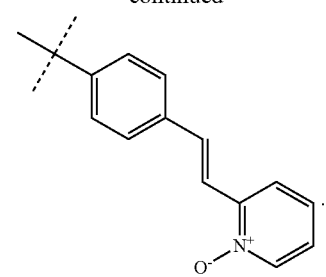
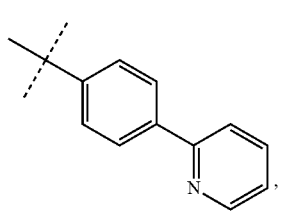
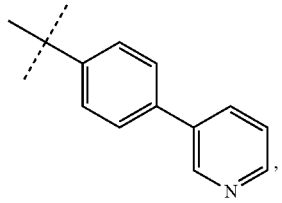
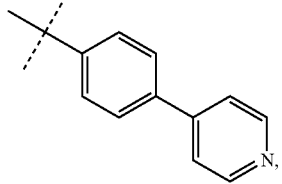
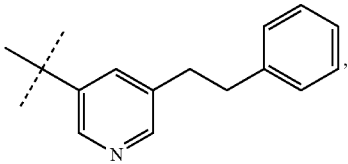
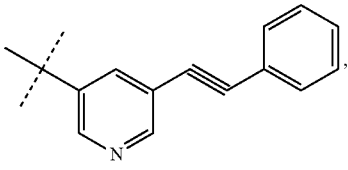
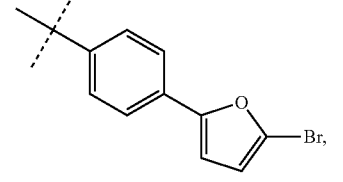
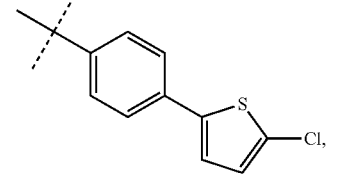
94
-continued
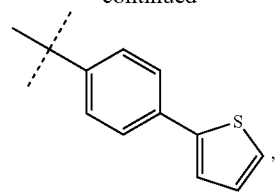
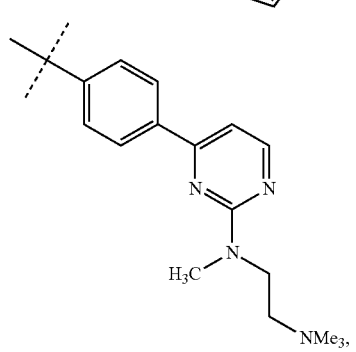
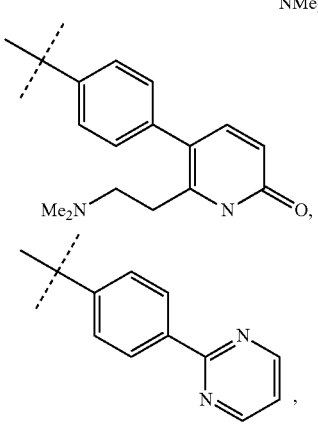
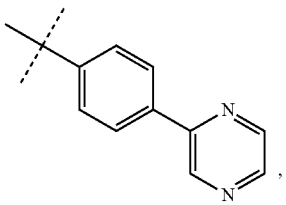
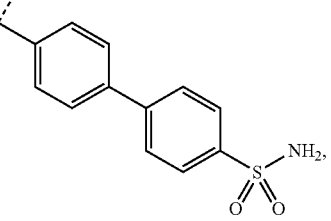
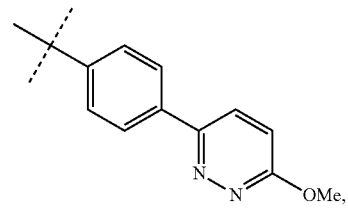

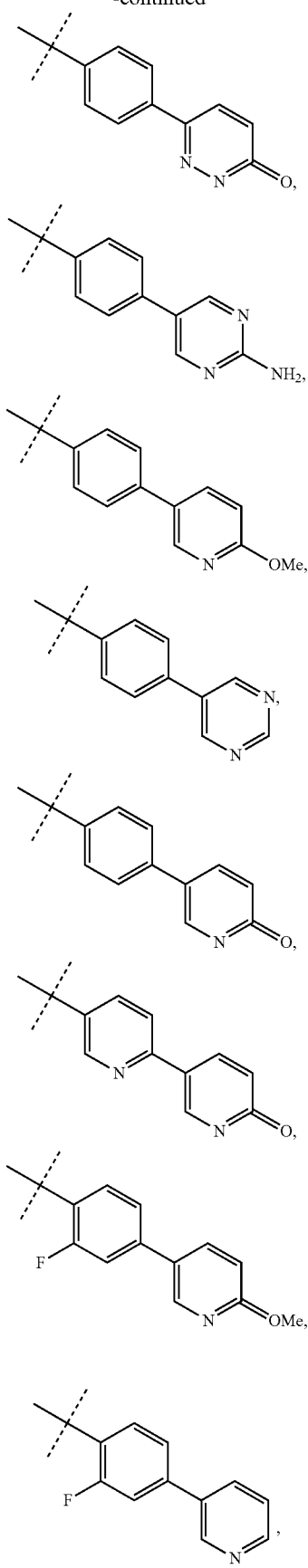
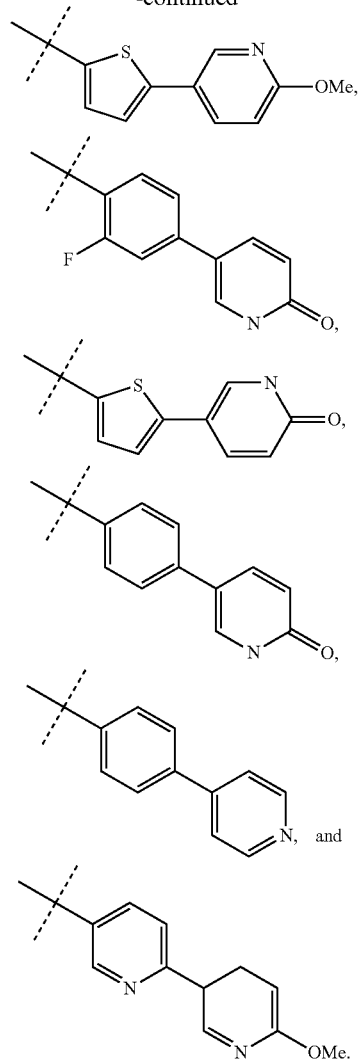

9. The compound according to claim 1 selected from the group consisting of
3-{1-[4-(6-Oxo-1,6-dihydropyridine-3-yl)-benzoyl]-1,2,3,6-tetrahydropyridin-4yl}benzamidine;
3-{1-[4-(1-Oxypyridin-2-yl)-benzoyl]-1,2,3,6-tetrahydropyridin-4 yl}benzamidine;
3-{1-[4-(1-Oxypyridin-4-yl)-benzoyl]-1,2,3,6-tetrahydropyridin-4-yl}benzamidine;
3-{1-[4-(6-Oxo-1,6-dihydropyridine-3-yl)-benzoyl]-piperidin-4-yl}benzamidine;
3-{1-[4-(1-Oxypyridin-4-yl)-benzoyl]-piperidin-4-yl}benzamidine;
3-{1-[4-(1-Oxypyridin-2-yl)-benzoyl]-piperidin-4-yl}benzamidine;
3-[1-(4-Pyridine-2-yl-benzoyl)-1,2,3,6-tetrahydropyridin-4-yl]benzamidine;
3-[1-(4-Pyridin-3-yl-benzoyl)-1,2,3,6-tetrahydropyridin-4-yl]benzamidine;
3-[1-(4-Pyridin-4-yl-benzoyl)-1,2,3,6-tetrahydropyridin-4-yl]benzamidine;
3-{1-[4-(5-Bromofuran-2-yl)-benzoyl]-1,2,3,6-tetrahydropyridin-4-yl}benzamidine;
3-{1-[4-(5-Chlorothiophen-2-yl)-benzoyl]-1,2,3,6-tetrahydropyridin-4-yl}benzamidine;

3-{1-(4-Thiophen-2-yl-benzoyl)-1,2,3,6-tetrahydropyridin-4-yl}benzamidine;
3-{1-[3-(5-Chlorothiophen-2-yl)-acryloyl]-1,2,3,6-tetrahydropyridin-4-yl}benzamidine;
3-[1-(4-{2-[(2-Dimethylaminoethyl)methylamino]pyrimidin-4-yl}benzoyl)-1,2,3,6-tetrahydropyridin-4-yl}benzamidine;
3-(1-{4-[2-(2-Dimethylaminoethyl)-6-oxo-1,6-dihydropyridin-3-yl]benzoyl}-1,2,3,6-tetrahydropyridin-4-yl)benzamidine;
3-[1-(4-Pyrimidin-2-ylbenzoyl)-1,2,3,6-tetrahydropyridin-4-yl]-benzamidine;
3-[1-(4-Pyrazin-2-ylbenzoyl)-1,2,3,6-tetrahydropyridin-4-yl]-benzamidine;
3-[1-(4'-Sulfamoylbiphenyl-4-carbonyl)-1,2,3,6-tetrahydropyridin-4-yl]-benzamidine;
3-[1-(3'-Sulfamoylbiphenyl-4-carbonyl)-1,2,3,6-tetrahydropyridin-4-yl]-benzamidine;
3-{1-[4-(6-Methoxypyridazin-3-yl)benzoyl]-1,2,3,6-tetrahydropyridin-4-yl]-benzamidine;
3-{1-[4-(6-Oxo-1,6dihydropyridazin-3-yl)benzoyl]-1,2,3,6-tetrahydropyridin-4-yl]-benzamidine;
3-{1-[4-(2-Aminopyrimidin-5-yl)benzoyl]-1,2,3,6-tetrahydropyridin-4-yl]-benzamidine;
3-{1-[4-(6-Methoxypyridin-3-yl)benzoyl]-1,2,3,6-tetrahydropyridin-4-yl]-benzamidine;
3-[1-(4-(Pyrimidin-5-ylbenzoyl)-1,2,3,6-tetrahydropyridin-4-yl]-benzamidine;
3-[1-(4-Pyridin-2-ylbenzoyl)-piperidin-4-yl]benzamidine;
3-[1-(4-Pyridin-3-ylbenzoyl)-piperidin-4-yl]benzamidine;
3-[1-(4-Pyridin-4-ylbenzoyl)-piperidin-4-yl]benzamidine;
3-{1-[4-(6-Methoxypyridin-3-yl)benzoyl]-piperidin-4-yl}benzamidine;
3-{1-[4-(6-Methoxypyridazin-3-yl)benzoyl]-piperidin-4-yl}benzamidine;
3-{1-[4-(6-Oxo-1,6-dihydropyridazin-3-yl)benzoyl]-piperidin-4-yl}benzamidine;
3-[1-(5-Phenylethyl-pyridine-3-carbonyl)-piperidin-4-yl]-benzamidine;
3-[1-(5-Phenylethynyl-pyridine-3-carbonyl)-1,2,3,6-tetrahydropyridin-4-yl]-benzamidine;
3-[1-(5-Phenylethynyl-pyridine-3-carbonyl)-piperidin-4-yl]-benzamidine; and
3-[4-(5-Phenylethyl-pyridine-3-carbonyl)-piperazin-1-yl]-benzamidine.

10. The compound according to claim 1 selected from the group consisting of
3-[1-(5-Phenylethyl-pyridine-3-carbonyl)-piperidin-4-yl]-benzamidine;
3-[1-(5-Phenylethynyl-pyridine-3-carbonyl)-1,2,3,6-tetrahydropyridin-4-yl]-benzamidine;
3-[1-(5-Phenylethynyl-pyridine-3-carbonyl)-piperidin-4-yl]-benzamidine;
3-{1-[4-(6-Methoxypyridin-3-yl)benzoyl]-1,2,3,6-tetrahydropyridin-4-yl]-benzamidine;
3-[1-(4-(Pyrimidin-5-ylbenzoyl)-1,2,3,6-tetrahydropyridin-4-yl]-benzamidine;
3-{1-[4-(6-Methoxypyridazin-3-yl)benzoyl]-piperidin-4-yl}benzamidine;
3-{1-[4-(1-Oxypyridin-2-yl)-benzoyl]-piperidin-4-yl}benzamidine;
3-[1-(4-Pyridine-2-yl-benzoyl)-1,2,3,6-tetrahydropyridin-4-yl]benzamidine;
3-[1-(4-Pyridin-3-yl-benzoyl)-1,2,3,6-tetrahydropyridin-4-yl]benzamidine;
3-[1-(4-{2-[(2-Dimethylaminoethyl)methylamino]pyrimidin-4-yl}benzoyl)-1,2,3,6-tetrahydropyridin-4-yl}benzamidine; and
3-[4-(5-Phenylethyl-pyridine-3-carbonyl)-piperazin-1-yl]-benzamidine.

11. The compound according to claim 1 selected from the group consisting of
3-{1-[4-(1-Oxypyridin-4-yl)-benzoyl]-1,2,3,6-tetrahydropyridin-4-yl}benzamidine;
3-{1-[4-(6-Oxo-1,6-dihydropyridine-3-yl)-benzoyl]-piperidin-4-yl}benzamidine;
3-{1-[4-(1-Oxypyridin-4-yl)-benzoyl]-piperidin-4-yl}benzamidine;
3-{1-[4-(6-Oxo-1,6dihydropyridazin-3-yl)benzoyl]-1,2,3,6-tetrahydropyridin-4-yl}-benzamidine;
3-{1-[4-(6-Oxo-1,6dihydropyridazin-3-yl)benzoyl]-1,2,3,6-tetrahydropyridin-4yl]-benzamidine; and
3-{1-[4-(6-Oxo-1,6dihydropyridazin-3-yl)benzoyl]-piperidin-4-yl}benzamidine.

12. A pharmaceutical composition comprising a pharmaceutically acceptable amount of the compound according to claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 7,947,684 B2 | Page 1 of 4 |
| APPLICATION NO. | : 10/616141 | |
| DATED | : May 24, 2011 | |
| INVENTOR(S) | : Heinz Pauls et al. | |

It is certified that error appears in the above-identified patent and that said Letters Patent is hereby corrected as shown below:

On the Title page, in field (30), in column 1, under "Foreign Application Priority Data", line 1, delete "Jul. 27, 2000" and insert -- Jul. 26, 2000 --, therefor.

In column 10, line 66, delete "$y^2$" and insert -- $Y^2$ --, therefor.

In column 16, line 32, delete "—$CH_2OR^-$" and insert -- —$CH_2OR^{13}$ --, therefor.

In column 30, line 56, delete "(DMS)" and insert -- (DMSO) --, therefor.

In column 31, line 5-6, delete "benzoyl}" and insert -- benzoyl] --, therefor.

In column 32, line 23, delete "(m, 1H)," and insert -- (m, 11H), --, therefor.

In column 32, line 34, after "4.2 (br, 2H)," insert -- 3.7 (br, 2H), --.

In column 33, line 45, delete "3.6 (br, 2H)." and insert -- 2.6 (br, 2H). --, therefor.

Signed and Sealed this
Fifteenth Day of May, 2012

David J. Kappos
*Director of the United States Patent and Trademark Office*

CERTIFICATE OF CORRECTION (continued)
U.S. Pat. No. 7,947,684 B2

In column 55, line 5-15, delete " 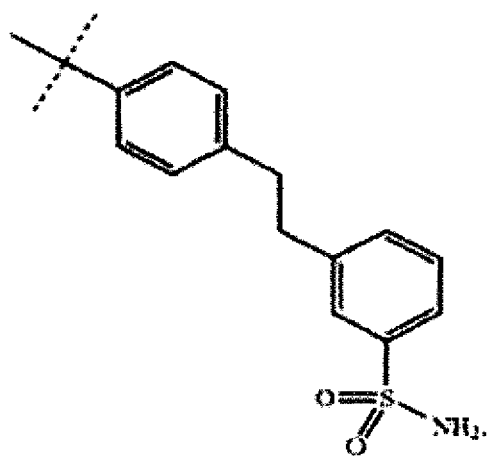 " and insert

-- 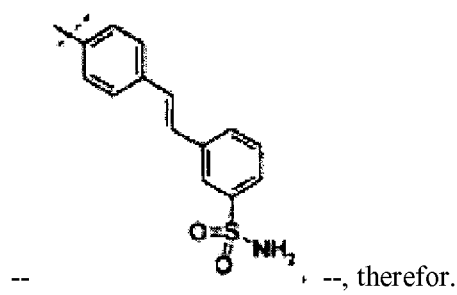 , --, therefor.

In column 75, line 10, in claim 1, delete "  " and insert -- -- , therefor.

In column 82, line 55-65, in claim 8, delete " 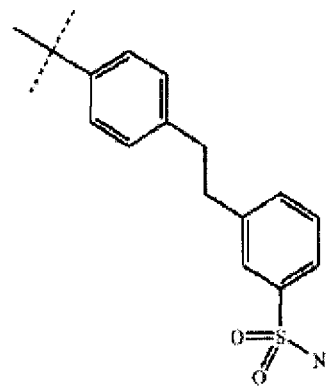 " and

CERTIFICATE OF CORRECTION (continued)
U.S. Pat. No. 7,947,684 B2 insert -- 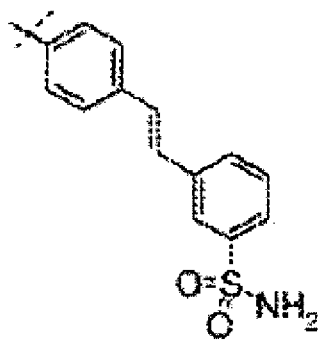 --, therefor.

In column 88, line 55-65, in claim 8, delete " 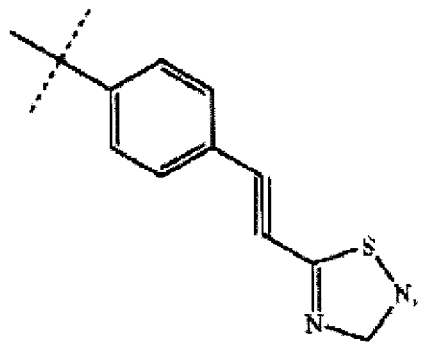 " and insert -- 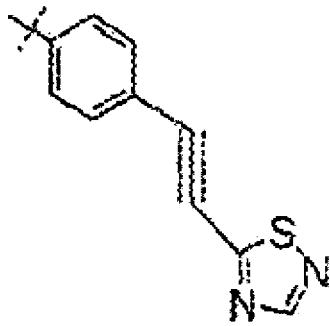 --, therefor.

CERTIFICATE OF CORRECTION (continued)
U.S. Pat. No. 7,947,684 B2

In column 94, line 10-20, in claim 8, delete " 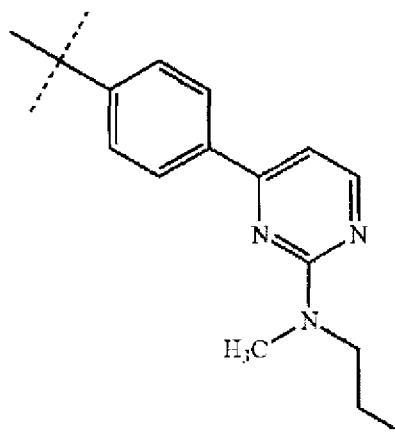 " and insert -- 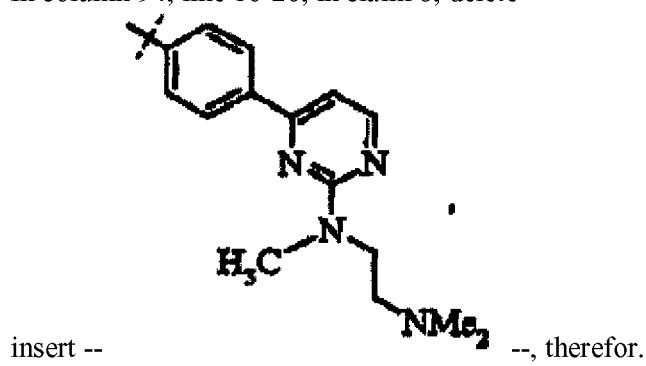 --, therefor.

In column 98, line 21, in claim 10, delete "-3-yl" and insert -- -4-yl --, therefor.